US012239948B2

(12) United States Patent
Tran

(10) Patent No.: US 12,239,948 B2
(45) Date of Patent: Mar. 4, 2025

(54) MATERIALS BASED ON NATURAL POLLEN GRAINS AND USES THEREOF

(71) Applicant: Marquette University, Milwaukee, WI (US)

(72) Inventor: Chieu D. Tran, Fox Point, WI (US)

(73) Assignee: Marquette University, Milwaukee, WI (US)

(*) Notice: Subject to any disclaimer, the term of this patent is extended or adjusted under 35 U.S.C. 154(b) by 371 days.

(21) Appl. No.: 17/620,364

(22) PCT Filed: Jun. 17, 2020

(86) PCT No.: PCT/US2020/038184
§ 371 (c)(1),
(2) Date: Dec. 17, 2021

(87) PCT Pub. No.: WO2020/257316
PCT Pub. Date: Dec. 24, 2020

(65) Prior Publication Data
US 2022/0250026 A1    Aug. 11, 2022

Related U.S. Application Data

(60) Provisional application No. 62/862,270, filed on Jun. 17, 2019.

(51) Int. Cl.
*B01J 13/20* (2006.01)
*A23P 10/30* (2016.01)
(Continued)

(52) U.S. Cl.
CPC ............ *B01J 13/203* (2013.01); *A23P 10/30* (2016.08); *C04B 20/0036* (2013.01); *C08L 1/02* (2013.01);
(Continued)

(58) Field of Classification Search
None
See application file for complete search history.

(56) References Cited

U.S. PATENT DOCUMENTS 5,374,710 A    12/1994  Tsien et al.
7,122,529 B2   10/2006  Ruane et al.
(Continued)

FOREIGN PATENT DOCUMENTS

CN    102168323 A    8/2011
CN    103012811 A    4/2013
(Continued)

OTHER PUBLICATIONS

Becherini et al. "Natural Sporopollenin Microcapsules Facilitated Encapsulation of Phase Change Material into Cellulose Composites for Smart and Biocompatible Materials" (Year: 2018).*
(Continued)

*Primary Examiner* — Ronak C Patel
(74) *Attorney, Agent, or Firm* — Quarles & Brady LLP

(57) ABSTRACT

Disclosed herein are methods for preparing sporopollenin exine capsules (SECs) and methods for preparing composite materials that comprise SECs that utilize ionic liquid compositions. The composite materials typically include structural polymers and the SECs, and the SECs optionally may encapsulate useful materials, such as flame retardant materials, phase change materials, and therapeutic materials, such as probiotics and prebiotics. The composite materials may be prepared from ionic liquid compositions comprising the structural polymers and the SECs which optionally may encapsulate the useful materials, where the ionic liquid is removed from the ionic liquid compositions to obtain the composite materials comprising the SECs.

24 Claims, 24 Drawing Sheets

(51) Int. Cl.
| | |
|---|---|
| C04B 20/00 | (2006.01) |
| C08L 1/02 | (2006.01) |
| C08L 5/00 | (2006.01) |
| C08L 89/06 | (2006.01) |
| D06M 23/12 | (2006.01) |
| C04B 111/28 | (2006.01) |
| D06M 101/06 | (2006.01) |

(52) U.S. Cl.
CPC .................. *C08L 5/00* (2013.01); *C08L 89/06* (2013.01); *D06M 23/12* (2013.01); *C04B 2111/28* (2013.01); *D06M 2101/06* (2013.01)

(56) References Cited

U.S. PATENT DOCUMENTS

| | | |
|---|---|---|
| 7,888,412 B2 | 2/2011 | Holbrey et al. |
| 8,609,843 B2 | 12/2013 | Mascharak |
| 2005/0232963 A1 | 10/2005 | Peplow et al. |
| 2005/0288484 A1 | 12/2005 | Holbrey |
| 2009/0149579 A1 | 6/2009 | Ito et al. |
| 2010/0239673 A1 | 9/2010 | Linhardt et al. |
| 2010/0297200 A1 | 11/2010 | Schoenfisch et al. |
| 2012/0040901 A1 | 2/2012 | Szente et al. |
| 2012/0184014 A1 | 7/2012 | Mascharak |
| 2014/0027938 A1 | 1/2014 | Swatloski et al. |
| 2016/0096931 A1 | 4/2016 | Tran |
| 2016/0145455 A1 | 5/2016 | Otake |
| 2016/0296655 A1 | 10/2016 | Suschek |
| 2018/0092852 A1 | 4/2018 | Gill et al. |
| 2019/0142001 A1 | 5/2019 | Tran |
| 2019/0240372 A1 | 8/2019 | Tran |

FOREIGN PATENT DOCUMENTS

| | | | |
|---|---|---|---|
| JP | 2007092024 A | 4/2007 | |
| KR | 20090092548 A | 9/2009 | |
| WO | 9616643 A1 | 6/1996 | |
| WO | 0132308 A1 | 5/2001 | |
| WO | 0209782 A1 | 2/2002 | |
| WO | 2004084627 A2 | 10/2004 | |
| WO | 2005000280 A2 | 1/2005 | |
| WO | 2005062896 A2 | 7/2005 | |
| WO | 2006116126 A2 | 11/2006 | |
| WO | 2007012856 A1 | 2/2007 | |
| WO | 2007067866 A2 | 6/2007 | |
| WO | 2008043837 A1 | 4/2008 | |
| WO | 2009038735 A1 | 3/2009 | |
| WO | 2009060438 A2 | 5/2009 | |
| WO | 2009077749 A1 | 6/2009 | |
| WO | 2009131989 A2 | 10/2009 | |
| WO | 2011056545 A2 | 5/2011 | |
| WO | 2011056924 A2 | 5/2011 | |
| WO | 2011153409 A1 | 12/2011 | |
| WO | 2014172703 A1 | 10/2014 | |
| WO | 2014186702 A1 | 11/2014 | |
| WO | WO-2017156256 A1 * | 9/2017 | ............ A01N 37/18 |
| WO | 2018075614 A1 | 4/2018 | |

OTHER PUBLICATIONS

Miller, Chemical Principles of Near-Infrared Technology, Near-Infrared Technology in the Agricultural and Food Industries, 2001, Chapter 2, pp. 19-37.

Mironava et al., Gold Nanoparticles Cellular Toxicity and Recovery: Effect of Size, Concentration and Exposure Time, Nanotoxicology, 2010, 4(1):120-137.

Mitragotri et al., Accelerating the Translation of Nanomaterials in Biomedicine, ACS Nano, 2015, 9(7):6644-6654.

Mohd et al., Dissolution of Cellulose in Ionic Liquid: A Review, AIP Conference Proceedings, 2017, 1809(1):020035, pp. 1-13.

Monk et al., Potent Bactericidal Efficacy of Copper Oxide Impregnated Non-Porous Solid Surfaces, BMC Microbiology, 2014, 14(1):57, pp. 1-14.

Mora-Pale et al., Room Temperature Ionic Liquids as Emerging Solvents for the Pretreatment of Lignocellulosic Biomass, Biotechnology and Bioengineering, 2011, 108(6):1229-1245.

Mori et al., Exploring the Confirmational Space of Amorphous Cellulose Using NMR Chemical Shifts, Carbohydrate Polymers, 2012, 90(3):1197-1203.

Morris et al., The Adsorption of Microcystin-LR by Natural Clay Particles, Toxicon, 2000, 38(2):303-308.

Mundargi et al., Eco-Friendly Streamlined Process for Sporopollenin Exine Capsule Extraction, Scientific Reports, 2016, 6:19960(1), pp. 1-14.

Mundargi et al., Lycopodium Spores: A Naturally Manufactured, Superrobust Biomaterial for Drug Delivery, Advanced Functional Materials, 2016, 26(4):487-497.

Murugesan et al., Ionic Liquids in Carbohydrate Chemistry—Current Trends and Future Directions, Current Organic Synthesis, 2005, 2(4):437-451.

Mututuvari et al., Facile Synthesis, Characterization and Antimicrobial Activity of Cellulose-Chistosan-Hydroxyapatite Composite Material, A Potential Material for Bone Tissue Engineering, Journal of Biomedical Materials Research, Part A, 2013, 101(11):3266-3277.

Mututuvari et al., Supramolecular Biopolymeric Composite Materials: Green Synthesis, Characterization, and Applications, Dissertation, Marquette University, 2014, 315 pages.

Mututuvari et al., Synergistic Adsorption of Heavy Metal Ions and Organic Pollutants by Polysaccharide Supramolecular Composite Materials from Cellulose, Chitosan and Crown Ether, Journal of Hazardous Materials, 2014, 264:449-459.

Naficy et al., Modulated Release of Dexamethasone from Chitosan-Carbon Nanotube Films, Sensors and Actuators A: Physical, 2009, 155(1):120-124.

Naqvi et al., Combined Efficacy of Biologically Synthesized Silver Nanoparticles and Different Antibiotics Against Multidrug-Resistant Bacteria, International Journal of Nanomedicine, 2013, 8:3187-3195.

Narasimha et al., Antiviral Properties of Silver Nanoparticles Synthesized by Aspergillus SPS, Der Pharmacia Lettre, 2012, 4(2):649-651.

Navea et al., Application of the Local Regression Method Interval Partial Least-Squares to the Elucidation of Protein Secondary Structure, Analytical Biochemistry, 2005, 336(2):231-242.

Neidrauer et al., Near Infrared Wound Monitor Helps Clinical Assessment of Diabetic Foot Ulcers, Journal of Diabetes Science and Technology, 2010, 4(4):792-798.

Newcombe et al., Water Treatment Options for Dissolved Cyanotoxins, Journal of Water Supply: Research and Technology—Aqua, 2004, 53(4):227-239.

Ngah et al., Comparison Study of Copper Ion Adsorption on Chitosan, Dowex A-1, and Zerolit 225, Journal of Applied Polymer Science, 1998, 67(6)1067-1070.

Niekraszewicz, Chitosan Medical Dressings, Fibres & Textiles in Eastern Europe, 2005, 13(6):54, pp. 16-18.

Nobile et al., Candida Albicans Biofilms and Human Disease, Annual Review of Microbiology, 2015, 69:71-92.

Noh et al., Antibacterial Activity and Increased Freeze-Drying Stability of Sialyllactose-Reduced Silver Nanoparticles using Sucrose and Trehalose, Journal of Nanoscience and Nanotechnology, 2012, 12:1-12.

O'Toole et al., Initiation of Biofilm Formation in Pseudomonas Fluorescens WCS365 Proceeds via Multiple, Convergent Signaling Pathways: A Genetic Analysis, Molecular Microbiology, 1998, 28(3):449-461.

Oda et al., Reconstituted High Density Lipoprotein Enriched with the Polyene Antibiotic, Amphotericin B, Journal of Lipid Research, 2006, 47(2):260-267.

Odewunmi et al., L-Citrulline: An Active Corrosion Inhibitor Component of Watermelon Rind Extract for Mild Steel in HCl Medium, Journal of the Taiwan Institute of Chemical Engineers, 2015, 51:177-185.

Odewunmi et al., Utilization of Watermelon Rind Extract as a Green Corrosion Inhibitor for Mild steel in Acidic Media, Journal of Industrial and Engineering Chemistry, 2015, 21:239-247.

(56) References Cited

OTHER PUBLICATIONS

Ohno et al., Task Specific Ionic Liquids for Cellulose Technology, Chemistry Letters, 2009, 38(1):2-7.
Ohno et al., Reaction Behavior of Cellulose in an Ionic Liquid, 1-ethyl-3-methylimidazolium Chloride, Journal of Wood Science, 2013, 59(3):221-228.
Oldfield, Chemical Shifts and Three-Dimensional Protein Structures, Journal of Biomolecular NMR, 1995, 5:217-225.
Oliver et al., Homogeneous Nucleation of n-Alkanes Measured by Differential Scanning Calorimetry, Journal of Crystal Growth, 1975, 30(3):343-351.
Othman et al., Watermelon Rind: A Potential Adsorbent for Zinc Removal, Applied Mechanics and Materials, 2014, 680:146-149.
Ozturk et al., Burn Wound Cooling with Tap Water: Is it Safe in Developing Countries or Not?, International Wound Journal, 2016, 13(5):1803.
Palazzo et al., Chiral Ionic Liquids Supported on Natural Sporopollenin Microcapsules, RSC Advances, 2018, 8(38):21174-21183.
Pan et al., Removal of Harmful Cyanobacterial Blooms in Taihu Lake Using Local Soils, III, Factors Affecting the Removal Efficiency and an In Situ Field Experiment Using Chitosan-Modified Local Soils, Enviornmental Pollution, 2006, 141(2):206-212.
Pan et al., Size-Dependent Cytotoxicity of Gold Nanoparticles, Small, 2007, 3(11):1941-1949.
Papazoglou et al., Noninvasive Assessment of Diabetic Foot Ulcers with Diffuse Photon Density Wave Methodology: Pilot Human Study, Journal of Biomedical Optics, 2009, 14(6):064032, pp. 1-10.
Papp et al., Inhibition of Influenza Virus Infection by Multivalent Sialic-Acid-Functionalized Gold Nanoparticles, Small, 2010, 6(24):2900-2906.
Park et al., Cellulose Composites Prepared Using Ionic Liquids (ILs)—Blood Compatibility to Batteries, Journal of American Chemical Society, 2009, Chapter 7, 1017:133-152.
Paul et al., Delivery of Antiviral Small Interfering RNA with Gold Nanoparticles Inhibits Dengue Virus Infection in Vitro, The Journal of General Virology, 2014, 95(8):1712-1722.
Pearson et al., On the Chemistry, Toxicology, and Genetics of the Cyanobacterial Toxins, Microcystin, Nodularin, Saxitoxin, and Cylindrospermopsin, Marine Drugs, 2010, 8(5):1650-1680.
Pelaz et al., The State of Nanoparticle-Based Nanoscience and Biotechnology: Progress, Promises, and Challenges, ACS Nano, 2012, 6(10):8468-8483.
Peng et al., Nanoporous Magnetic Cellulose-Chitosan Composite Microspheres: Preparation, Characterization, and Application for Cu (II) Adsorption, Industrial & Engineering Chemistry Research, 2014, 53(6):2106-2113.
Peng et al., n Alkanes Phase Change Materials and Their Microencapsulation for Thermal Energy Storage: A Critical Review, Energy & Fuels, 2018, 32(7):7262-7293 [in three parts due to file size].
Peppas et al., A Simple Equation for the Description of Solute Release III: Coupling of Diffusion and Relaxation, International Journal of Pharmaceuticals, 1989, 57(2):169-172.
Percival et al., Biofilms and Wounds: An Overview of the Evidence, Advances in Wound Care, 2015, 4(7):373-381.
Percot et al., Characterization of Shrimp Shell Deproteinization, Biomacromolecules, 2003, 4(5):1380-1385.
Pernodet et al., Adverse Effects of Citrate/Gold Nanoparticles on Human Dermal Fibroblasts, Small, 2006, 2(6):766-773.
Persson et al., Correlation of in Vitro Dissolution Rate and Apparent Solubility in Buffered Media Using a Miniaturized Rotating Disk Equipment: Part 1, Comparison with a Traditional USP Rotating Disk Apparatus, Drug Discoveries & Therapeutics, 2009, 3(3):104-113.
Finkenstadt et al., Crystal structure of Valonia Cellulose Iβ, Macromolecules, 1998, 31(22):7776-7783.
Fischer et al., Evidence for Kinetic Inhomogeneity in the Curing of Epoxy using the Near-Infrared Multispectral Imaging Technique, Analytical Chemistry, 1999, 71(5):953-959.
Fischer et al., Investigation of Solid Phase Peptide Synthesis by the Near Infrared Multispectral Imaging Technique: A Detection Method for Combinatorial Chemistry, Analytical Chemistry, 1999, 71(13):2255-2261.
Franko et al., Thermal Lens Spectroscopy, Electronic Absorption and Luminescence Spectroscopy, Encyclopedia of Analytical Chemistry, 2010, pp. 1-32.
Frez et al., Determination of Thermal Diffusivities, Thermal Conductivities, and Sound Speeds of Room-Temperature Ionic Liquids by the Transient Grating Technique, Journal of Chemical & Engineering Data, 2006, 51(4):1250-1255.
Fujimori et al., Novel Antiviral Characteristics of Nanosized Copper (I) Iodide Particles Showing Inactivation Activity Against 2009 Pandemic H1N1 Influenza Virus, Applied and Environmental Microbiology, 2012, 78(4):951-955.
Fukaya et al., Cellulose Dissolution with Polar Ionic Liquids under Mild Conditions: Required Factors for Anions, Green Chemistry, 2008, 10(1):44-46.
Gangadharan et al., Polymeric Microspheres Containing Silver Nanoparticles as Bactericidal Agent for Water Disinfection, Water Research, 2010, 44(18):5481-5487.
General Electric Company, Water & Process Technologies: Analytical Instruments, Sievers, Nitric Oxide Analyzer (NOA 280i), Retrieved from http://geinstruments.com/GetLibraryDoc.aspx?id=7655eda5-5862-4b93-8b3e-e57a87a8fb5c, Copyright 2008 General Electric Company, 4 pages.
Giannuzzi et al., An Acute Case of Intoxication with Cyanobacteria and Cyanotoxins in Recreational Water in Salto Grande Dam, Argentina, Marine Drugs, 2011, 9(11):2164-2175.
Gonil et al., Novel Quaternized Chitosan Containing β-Cyclodextrin Moiety: Synthesis, Characterization and Antimicrobial Activity, Carbohydrate Polymers, 2011, 83(2):905-913.
Gonzalez-Cruz et al., A Chemical Treatment Method for Obtaining Clean and Intact Pollen Shells of Different Species, ACS Biomaterials Science & Engineering, 2018, 4(7):2319-2329.
Gopu et al., Petunidin as a Competitive Inhibitor of Acylated Homoserine Lactones in Klebsiella Pneumoniae, RSC Advances, 2016, 6(4):2592-2601.
Greve et al., Penetration Mechanism of Dimethyl Sulfoxide in Human and Pig Ear Skin: An ATR-FTIR and Near-FT Raman Spectroscopic In Vivo and In Vitro Study, Spectroscopy, 2008, 22(5):405-417.
Gu et al., Adsorption of Avermectins on Activated Carbon: Equilibrium, Kinetics, and UV-Shielding, Transactions of Nonferrous Metals Society of China, 2009, 19:s845-s850.
Gunapala et al., 15-μm 128×128 GaAs/A1xGa1-xAs Quantum Well Infrared Photodetector Focal Plane Array Camera, IEEE Transactions on Electron Devices, 1997, 44(1):45-50.
Guzman et al., Synthesis and Antibacterial Activity of Silver Nanoparticles against Gram-Positive and Gram-Negative Bacteria, Nanomedicine: Nanotechnology, Biology, and Medicine, 2012, 8(1):37-45.
Hale et al., Optical Constants of Water in the 200-nm to 200-μm Wavelength Region, Applied Optics, 1973, 12(3):555-563.
Hamad et al., Sporopollenin Microcapsules for Microencapsulation of Living Cells, Materials Research Society Symposium Proceedings, 2013, 1499, 6 pages.
Han et al., Ionic Liquids in Separations, Accounts of Chemical Research, 2007, 40(11):1079-1086.
Han et al., Effective Encapsulation of Paraffin Wax in Carbon Nanotube Agglomerates for New Shape-Stabilized Phase Change Material with Enhanced Thermal Storage Capacity and Stability, Industrial & Engineering Chemistry Research, 2018, 57(39):13026-13035.
Hargreaves et al., Spectroscopic Studies of Amphotericin B Solubilized in Nanoscale Bilayer Membranes, Biochimica et Biophysica Acta (BBA)—Biomembranes, 2006, 1758(1):38-44.
Harkins et al., Chitosan-Cellulose Composite for Wound Dressing Material, Part 2, Antimicrobial Activity, Blood Absorption Ability, and Biocompatibility, Journal of Biomedical Materials Research, Part B: Applied Biomaterials, 2014, 102(6):1199-1206.
Härtig et al., Kinetics of nirS Expression (Cytochrome cd1 Nitrite Reductase) in Pseudomonas Stutzeri during the Transition from

(56) References Cited

OTHER PUBLICATIONS

Aerobic Respiration to Denitrification: Evidence for a Denitrification-Specific Nitrate- and Nitrite-Responsive Regulatory System, Journal of Bacteriology, 1999, 181(1):161-166.

Hassan et al., Removal of Boron from Industrial Wastewater by Chitosan via Chemical Precipitation, Journal of Chemical and Natural Resources Engineering, 2009, 4(1):1-11.

He et al., Phase-Change Characteristics and Thermal Performance of Form-Stable N-Alkanes/Silica Composite Phase Change Materials Fabricated by Sodium Silicate Precursor, Renewable Energy, 2015, 74:689-698.

Hideno, Comparison of the Thermal Degradation Properties of Crystalline and Amorphous Cellulose, as well as Treated Lignocellulosic Biomass, BioResources, 2016, 11(3):6309-6319.

Higuchi, Mechanism of Sustained-Action Medication, Theoretical Analysis of Rate of Release of Solid Drugs Dispersed in Solid Matrices, Journal of Pharmaceutical Sciences, 1963, 52(12):1145-1149.

Hill et al., Some Properties of Keratin Biomaterials: Kerateines, Biomaterials, 2010, 31(4):585-593.

Hinze, Organized Surfactant Assemblies in Separation Science, ACS Symposium Series, American Chemical Society, 1987, Chapter 1, pp. 1-82.

Hitomi et al., Electronic Tuning of Nitric Oxide Release from Manganese Nitrosyl Complexes by Visible Light Irradiation: Enhancement of Nitric Oxide Release Efficiency by the Nitro-Substituted Quinoline Ligand, Dalton Transactions, 2014, 43(5):2161-2167.

Huang et al., Cleansing of Wounds by Tap Water? An Evidenced Based Systemic Analysis, International Wound Journal, 2015, 12(4):493-494.

Ibrahim et al., Comparative Isotherms Studies on Adsorptive Removal of Congo Red from Wastewater by Watermelon Rinds and Neem-Tree Leaves, Open Journal of Physical Chemistry, 2014, 4:139-146.

International Centre for Diffraction Data, Powder Diffraction FileTM (PDF®) Search, Copyright 1997-2023 JCPDS International Centre for Diffraction Data, 1 page.

International Standard, Biological Evaluation of Medical Devices—Part 5: Tests for in Vitro Cytotoxicity, ISO 10993-5:2009(E), 2009, 42 pages.

Iqbal et al., In Situ Development of Self-Defensive Antibacterial Biomaterials: Phenol-g-keratin-EC Based Bio-Composites with Characteristics for Biomedical Applications, Green Chemistry, 2015, 17(7):3858-3869.

Iwamoto et al., Uncaging a Catalytic Hydrogen Peroxide Generator Through the Photo-Induced Release of Nitric Oxide From a {MnNO}6 Complex, Chemical Communications, 2015, 51(46):9539-9542.

Jain et al., Comparison of Ciprofloxacin Hydrochloride-Loaded Protein, Lipid, and Chitosan Nanoparticles for Drug Delivery, Journal of Biomedical Materials Research, Part B: Applied Biomaterials, 2008, 86(1):105-112.

Jain et al., Raman Spectroscopy Enables Noninvasive Biochemical Characterization and Identification of the Stage of Healing of a Wound, Analytical Chemistry, 2014, 86(8):3764-3772.

Jayakumar et al., Biomaterials based on Chitin and Chitosan in Wound Dressing Applications, Biotechnology Advances, 2011, 29(3):322-337.

Jeon et al., Structures of Ionic Liquids with Different Anions Studied by Infrared Vibration Spectroscopy, The Journal of Physical Chemistry B, 2008, 112(15):4735-4740.

Ji et al., Extraction of Keratin with Ionic Liquids from Poultry Feather, Separation and Purification Technology, 2014, 132:577-583.

Jia et al., Preparation of Copper Nanoparticles Coated Cellulose Films with Antibacterial Properties through One-Step Reduction, ACS Applied Materials & Interfaces, 2012, 4(6):2897-2902.

Jiang et al., Design and Synthesis of Magnetic Microcapsules based on n-Eicosane Core and Fe3O4/SiO2 Hybrid Shell for Dual-Functional Phase Change Materials, Applied Energy, 2014, 134:456-468.

Johnston et al., Nanogold and Nanosilver Composites with Lignin-Containing Cellulose Fibres, Journal of Materials Science, 2012, 47:1103-1112.

Joint Trauma System Clinical Practice Guideline (JTS CPG), Burn Wound Management Under Prolonged Field Care (CPG ID:57), 2017, 20 pages.

Jorgensen et al., Antimicrobial Susceptibility Testing: A Review of General Principles and Contemporary Practices, Clinical Infectious Diseases, 2009, 49(11):1749-1755.

Kabsch et al., Dictionary of Protein Secondary Structure: Pattern Recognition of Hydrogen-Bonded and Geometrical Features, Biopolymers: Original Research on Biomolecules, 1983, 22(12):2577-2637.

Kaiser et al., Noninvasive Assessment of Burn Wound Severity Using Optical Technology: A Review of Current and Future Modalities, Burns, 2011, 37(3):377-386.

Karaman et al., Comparison of Sparse and Jack-Knife Partial Least Squares Regression Methods for Variable Selection, Chemometrics and Intelligent Laboratory Systems, 2013, 122:65-77.

Adjepong et al., The Role of Antioxidant Micronutrients in the Rate of Recovery of Burn Patients: A Systematic Review, Burns & Trauma, 2016, 4(18):1-7.

Ahn et al., Anti-Diabetic Effect of Watermelon (*Citrullus vulgaris schrad*) on Streptozotocin-Induced Diabetic Mice, Food Science and Biotechnology, 2011, 20(1):251-254.

Alam et al., Study on the Physico-Mechanical Properties of Photo-Cured Chitosan Films with Oligomer and Acrylate Monomer, Journal of Polymers and the Environment, 2008, 16:213-219.

Alexander et al., Near-Infrared Multispectral Imaging Technique for Visualizing Sequences of Di-and Tripeptides Synthesized by Solid Phase Combinatorial Method, Applied Spectroscopy, 2001, 55(7):939-945.

Alexander et al., Near-Infrared Spectrometric Determination of Di-and Tripeptides Synthesized by a Combinatorial Solid-Phase Method, Analytical Chemistry, 2001, 73(5):1062-1067.

Alsarra, Chitosan Topical Gel Formulation in the Management of Burn Wounds, International Journal of Biological Macromolecules, 2009, 45(1):16-21.

Alshehri et al., Delivery of Ibuprofen by Natural Macroporous Sporopollenin Exine Capsules Extracted from *Phoenix dactylifera* L, European Journal of Pharmaceutical Sciences, 2016, 88:158-165.

Altiok et al., Physical, Antibacterial and Antioxidant Properties of Chitosan Films Incorporated with Thyme Oil for Potential Wound Healing Applications, Journal of Materials Science: Materials in Medicine, 2010, 21:2227-2236.

Aluigi et al., Structure and Properties of Keratin/PEO Blend Nanofibers, European Polymer Journal, 2008, 44(8):2465-2475.

American Burn Association, Support Funding for the Military Burn Research Program in FY19, 2018, 7 pages.

Ammann et al., Detection and Differentiation of Bacterial Spores in a Mineral Matrix by Fourier Transform Infrared Spectroscopy (FTIR) and Chemometrical Data Treatment, BMC Biophysics, 2011, 4:14, pp. 1-7.

Aoki et al., Preparation of Insoluble Chitosan Beads Functionalized by Carboxymethylated Beta-Cyclodextrin, Transactions of the Materials Research Society of Japan, 2005, 30(4):1143-1146.

Aoki et al., Removal of Phenolic Compounds from Aqueous Solutions using Ionic Interaction Between Cyclodextrin Derivatives and Chitosan, Transactions of the Materials Research Society of Japan, 2010, 35(4):809-812.

Appelbaum, Microbiology of Antibiotic Resistance in *Staphylococcus aureus*, Clinical Infectious Diseases, 2007, 45 (Supplement_3):S165-S170.

Arrondo et al., Quantitative Studies of the Structure of Proteins in Solution by Fourier-Transform Infrared Spectroscopy, Progress in Biophysics and Molecular Biology, 1993, 59(1):23-56.

Artes-Hernandez et al., Low UV-C Illumination for Keeping Overall Quality of Fresh-Cut Watermelon, Postharvest Biology and Technology, 2010, 55(2):114-120.

Asahi et al., Simple Observation of *Streptococcus* Mutans Biofilm by Scanning Electron Microscopy using Ionic Liquids, AMB Express, 2015, 5(6):1-9.

(56) References Cited

OTHER PUBLICATIONS

Atrian et al., An Evolutionary and Structure-Based Docking Model for Glucocerebrosidase-Saposin C and Glucocerebrosidase-Substrate Interactions—Relevance for Gaucher Disease, Proteins: Structure, Function, and Bioinformatics, 2008, 70(3):882-891.

Baptista et al., Near-Infrared Detection of Flow Injection Analysis by Acoustooptic Tunable Filter Based Spectrophotometry, Analytical Chemistry, 1996, 68(6):971-976.

Barone et al., Extrusion of Feather Keratin, Journal of Applied Polymer Science, 2006, 100(2):1432-1442.

Barrier et al., Viability of Plant Spore Exine Capsules from Microencapsulation, Journal of Materials Chemistry, 2011, 21(4):975-981.

Baxter et al., Improved Method for I.R. Determination of the Degree of N-Acetylation of Chitosan, International Journal of Biological Macromolecules, 1992, 14(3):166-169.

Becherini et al., Natural Sporopollenin Microcapsules Facilitated Encapsulation of Phase Change Material into Cellulose Composites for Smart and Biocompatible Materials, ACS Applied Materials & Interfaces, 2019, 11(47):44708-44721.

Belusko et al., Direcy Contact Phase Change Material Thermal Energy Stroage, High-Temperature Thermal Storage Systems using Phase Change Materials, 2018, Chapter 2, pp. 7-37, in Cabeza, editor, High-Temperature Thermal Storage Systems using Phase Change Materials, Academic Press.

Benhabiles et al., Antibacterial Activity of Chitin, Chitosan and its Oligomers Prepared from Shrimp Shell Waste, Food Hydrocolloids, 2012, 29(1):48-56.

Berth et al., The Degree of Acetylation of Chitosans and its Effect on the Chain Conformation in Aqueous Solution, Carbohydrate Polymers, 2002, 47(1):39-51.

Bettinetti et al., Polymorphism, Pseudopolymorphism, and Amorphism of Peracetylated α-, β-, and γ-Cyclodextrins, Journal of Pharmaceutical and Biomedical Analysis, 2006, 41(4):1205-1211.

Boh et al., Microencapsulation Technology and its Applications in Building Construction Materials, RMZ—Materials and Geoenvironment, 2008, 55(3):329-344.

Bojana et al., Microencapsulation Technology and Applications in Added-Value Functional Textiles, Physical Sciences Reviews, 2016, 1(1):20150003, pp. 1-27.

Bordenave et al., Hydrophobization and Antimicrobial Activity of Chitosan and Paper-Based Packaging Material, Biomacromolecules, 2010, 11(1):88-96.

Borkow, Using Copper to Improve the Well-Being of the Skin, Current Chemical Biology, 2014, 8(2):89-102.

Boroumand et al., Novel Method for Synthesis of Silver Nanoparticles and their Application on Wool, Applied Surface Science, 2015, 346:477-483.

Bowler, The 10(5) Bacterial Growth Guideline: Reassessing its Clinical Relevance in Wound Healing, Ostomy Wound Management, 2003, 49(1):44-53.

Brumshtein et al., Characterization of Gene-Activated Human Acid-Beta-Glucosidase: Crystal Structure, Glycan Composition, and Internalization into Macrophages, Glycobiology, 2010, 20(1):24-32.

Brust et al., Synthesis of Thiol-Derivatised Gold Nanoparticles in a Two-Phase Liquid-Liquid System, Journal of the Chemical Society, Chemical Communications, 1994, 7:801-802.

Burkatovskaya et al., Use of Chitosan Bandage to Prevent Fatal Infections Developing from Highly Contaminated Wounds in Mice, Biomaterials, 2006, 27(22):4157-4164.

Cai et al., Dilute Solution Properties of Cellulose in LiOH/Urea Aqueous System, Journal of Polymer Science Part B: Polymer Physics, 2006, 44(21):3093-3101.

Cai et al., Fabrication of Chitosan/Silk Fibroin Composite Nanofibers for Wound Dressing Applications, International Journal of Molecular Sciences, 2010, 11(9):3529-3539.

Cardinal Health, Cardinal Health™ Curity™ AMD Antimicrobial Woven Sponges, Copyright 2023 Cardinal Health, Retrieved from https://www.cardinalhealth.com/en/product-solutions/medical/skin-and-wound-management/traditional-wound-care/woven-dressings/curity-amd-sponges.html, 4 pages.

Chakraborty et al., Adsorption of Crystal Violet from Aqueous Solution onto NaOH-Modified Rice Husk, Carbohydrate Polymers, 2001, 86(4):1533-1541.

Chalmers et al., FT-IR Imaging of Polymers: An Industrial Appraisal, Vibrational Spectroscopy, 2002, 30(1):43-52.

Chan et al., A Year for Nanoscience, ACS Nano, 2014, 8(12):11901-11903.

Chang et al., Wool Powder: An Efficient Additive to Improve Mechanical and Thermal Properties of Poly(Propylene Carbonate), Composites Science and Technology, 2017, 153:119-127.

Chen et al., Complexation of Microcystins and Nodularin by Cyclodextrins in Aqueous Solution, A Potential Removal Strategy, Environmental Science & Technology, 2011, 45(6):2293-2300.

Chen et al., What Happens during Natural Protein Fibre Dissolution in Ionic Liquids, Materials, 2014, 7(9):6158-6168.

Cheng et al., Interplay Between Candida Albicans and the Mammalian Innate Host Defense, Infection and Immunity, 2012, 80(4):1304-1313.

Cheng et al., Synthesis and Antibacterial Effects of Aqueous Colloidal Solutions of Silver Nanoparticles using Aminocellulose as a Combined Reducing and Capping Reagent, Green Chemistry, 2013, 15(4):989-998.

Chiappe, Product as Reaction Solvent: An Unconventional Approach for Ionic Liquid Synthesis, Organic Process Research & Development, 2016, 20(12):2080-2084.

Chiappe et al., From Pollen Grains to Functionalized Microcapsules: A Facile Chemical Route Using Ionic Liquids, Green Chemistry, 2017, 19(4):1028-1033.

Chiodo et al., Glycosystems in Nanotechnology: Gold Glyconanoparticles as Carrier for Anti-HIV Prodrugs, Beilstein Journal of Organic Chemistry, 2014, 10(1):1339-1346.

Kelly et al., Colored and Functional Silver Nanoparticle-Wool Fiber Composites, ACS Applied Materials & Interfaces, 2011, 3(4):1083-1092.

Kennedy et al., Burns, Biofilm and a New Appraisal of Burn Wound Sepsis, Burn, 2010, 36(1):49-56.

Keong et al., In Vitro Models in Biocompatibility Assessment for Biomedical-Grade Chitosan Derivatives in Wound Management, International Journal of Molecular Sciences, 2009, 10(3):1300-1313.

Kesarkar et al., Gold Nanoparticles: Effective as Both Entry Inhibitors and Virus Neutralizing Agents Against HIV, Journal of Microbiology and Biotechnology, 2012, 2(2):276-283.

Khait et al., Time-Resolved Multispectral Imaging Spectrometer, Applied Spectroscopy, 2000, 54(12):1734-1742.

Khait et al., Multispectral Imaging Microscope with Millisecond Time Resolution, Analytical Chemistry, 2001, 73:732-739.

Khan et al., Modification and Characterization of Chitosan Films Using 3-Trimethoxysilylpropyl Methacrylate, Journal of Macromolecular Science, Part A: Pure and Applied Chemistry, 2009, 46(8):751-758.

Khosa et al., Sustainable Role of Keratin Biopolymer in Green Chemistry: A Review, Journal of Food Processing & Beverages, 2013, 1(1):4, pp. 1-8.

Kim et al., Interplay of Tumor Vascular Oxygenation and Tumor pO2 Observed Using Near-Infrared Spectroscopy, an Oxygen Needle Electrode, and 19F Mr pO2 Mapping, Journal of Biomedical Optics, 2003, 8(1):53-62.

Kim et al., A Platform for Nitric Oxide Delivery, Journal of Materials Chemistry B, 2014, 2(4):341-356.

Kitaoka et al., Adsorption of Bisphenol A by Cross-Linked β-Cyclodextrin Polymer, Journal of Inclusion Phenomena and Macrocyclic Chemistry, 2002, 44:429-431.

Koebke et al., Does the Oxidation of Nitric Oxide by OxyMyoglobin Share an Intermediate with the MetMyoglobin-Catalyzed Isomerization of Peroxynitrite?, Inorganic Chemistry, 2013, 52(13):7623-7632.

Koebke et al., Direct Monitoring of the Reaction between Photochemically Generated Nitric Oxide and Mycobacterium Tubercu-

(56) References Cited

OTHER PUBLICATIONS losis Truncated Hemoglobin N Wild Type and Variant Forms: An Assessment of Computational Mechanistic Predictions, Biochemistry, 2016, 55(4):686-696.
Konop et al., Certain Aspects of Silver and Silver Nanoparticles in Wound Care: A Minireview, Journal of Nanomaterials, 2016, 2016:1-10.
Konuklu et al., Nanoencapsulation of N-Alkanes with Poly(Styrene-Co-Ethylacrylate) Shells for Thermal Energy Storage, Applied Energy, 2015, 150:335-340.
Korsmeyer et al., Mechanism of Solute Release from Porous Hydrophilic Polymers, International Journal of Pharmaceuticals, 1983, 15(1):25-35.
Korte et al., Thermal Lens Spectrometric Determination of Colloidal and Ionic Silver in Water, International Journal of Thermophysics, 2011, 32:818-827.
Kumar et al., Investigation into the Interaction Between Surface-Bound Alkylamines and Gold Nanoparticles, Langmuir, 2003, 19(15):6277-6282.
Kundu et al., Arsenic Adsorption onto Iron Oxide-Coated Cement (IOCC): Regression Analysis of Equilibrium Data with Several Isotherm Models and their Optimization, Chemical Engineering Journal, 2006, 122(1-2):93-106.
Lakshmipathy et al., A Fixed Bed Column Study for the Removal of Pb2+ Ions by Watermelon Rind, Environmental Science: Water Research & Technology, 2015, 1(2):244-250.
Lakshmipathy et al., Watermelon Rind-Mediated Green Synthesis of Noble Palladium Nanoparticles: Catalytic Application, Applied Neuroscience, 2015, 5:223-228.
Lamprecht et al., The Thermal Decomposition of Copper (II) Oxalate Revisited, Thermochimica Acta, 2006, 446(1-2):91-100.
Langford et al., Scherrer After Sixty Years: A Survey and Some New Results in the Determination of Crystallite Size, Journal of Applied Crystallography, 1978, 11(2):102-113.
Langmuir, The Constitution and Fundamental Properties of Solids and Liquids, Part 1, Solids, Journal of the American Chemical Society, 1916, 38(11):2221-2295 [in two parts due to file size].
Lazary et al., Reduction of Healthcare-Associated Infections in a Long-Term Care Brain Injury Ward by Replacing Regular Linens with Biocidal Copper Oxide Impregnated Linens, International Journal of Infectious Diseases, 2014, 24:23-29.
Li et al., Purification of Chitosan by Using Sol-Gel Immobilized Pepsin Deproteinization, Carbohydrate Polymers, 2012, 88(1):206-212.
Li et al., Preparation of Regenerated Wool Keratin Films from Wool Keratin-Ionic Liquid Solutions, Journal of Applied Polymer Science, 2013, 127(4):2648-2653.
Li et al., Fabrication of Multifunctional Microcapsules Containing n-Eicosane Core and Zinc Oxide Shell for Low Temperature Energy Storage, Photocatalysis, and Antibiosis, Energy Conversion and Management, 2015, 106:873-885.
Li et al., The Molecular Structure of Plant Sporopollenin, Nature Plants, 2018, bioRxiv preprint doi: https://doi.org/10.1101/415612, 150 pages [in three parts due to file size].
Liang et al., Preparation of Single or Double-Network Chitosan/Poly(Vinyl Alcohol) Gel Films Through Selectively Cross-Linking Method, Carbohydrate Polymers, 2009, 77(4):718-724.
Liebert et al., Cellulose Solvents: For Analysis, Shaping and Chemical Modification, ACS Symposium Series: American Chemical Society, 2010, 1033, 299-317.
Lipman et al., Odor Absorbing Hydrocolloid Dressings for Direct Wound Contact, Wounds, 2007, 19(5):138-146.
Liu et al., Biocompatible Magnetic Cellulose-Chitosan Hybrid Gel Microspheres Reconstituted from Ionic Liquids for Enzyme Immobilization, Journal of Materials Chemistry, 2012, 22(30):15085-15091.
Liu et al., Magnetic Cellulose-Chitosan Hydrogels Prepared from Ionic Liquids as Reusable Adsorbents for Removal of Heavy Metal Ions, Chemical Communications, 2012, 48(59):7350-7352.
Lokshyn et al., Nanoparticles in Antivirus Therapy, Advanced Materials Research, 2014, 854:149-155.
Mackenzie et al., Pollen and Spore Shells—Nature's Microcapsules, Microencapsulation in the Food Industry, 2014, Chapter 24, pp. 283-297.
Mallakpour et al., A Facile, Efficient, and Green Fabrication of Nanocomposites based on L-Leucine Containing Poly(amide-imide) and PVA-Modified Ag Nanoparticles by Ultrasonic Irradiation, Colloid and Polymer Science, 2015, 293:1827-1833.
Marques et al., The Use of Near Infrared Spectroscopy and Multivariate Techniques to Differentiate *Escherichia coli* and *Salmonella enteritidis* Inoculated into Pulp Juice, Journal of Microbiological Methods, 2013, 93(2):90-94.
Mateo et al., Comparative Cytotoxicity Evaluation of Different Size Gold Nanoparticles in Human Dermal Fibroblasts, Journal of Experimental Nanoscience, 2015, 10(18):1401-1417.
McDougald et al., Should we Stay or Should we go: Mechanisms and Ecological Consequences for Biofilm Dispersal, Nature Reviews Microbiology, 2012, 10(1):39-50.
McIntosh et al., Spectroscopic Analysis of Bacterial Biological Warfare Stimulants and the Effects of Environmental Conditioning on a Bacterial Spectrum, Analytical and Bioanalytical Chemistry, 2012, 404:2307-2315.
McKittrick et al., The Structure, Functions, and Mechanical Properties of Keratin, JOM, 2012, 64(4):449-468.
Medline, SilvaSorb Silver Antimicrobial Wound Gel, Copyright 2023 Medline Industries, LP, Retrieved from https://punchout.medline.com/product/SilvaSorb-Silver-Antimicrobial-Wound-Gel/Antimicrobial-Gel/Z05-PF00181, 1 page.
Mejac et al., Visualizing the Size, Shape, Morphology, and Localized Surface Plasmon Resonance of Individual Gold Nanoshells by Near-Infrared Multispectral Imaging Microscopy, Analytical Chemistry, 2009, 81:6687-6694.
Mejac et al., Visualizing the Lower Critical Solution Temperature Phase Transition of Individual Poly(Nipam)-Based Hydrogel Particles using Near-Infrared Multispectral Imaging Microscopy, Analytical Chemistry, 2010, 82(5):1698-1704.
Mejac, Development and Applications of Ionic Liquids and Near-Infrared Multispectral Imaging Techniques, Dissertation, Marquette University, 2011, 206 pages.
Mejac et al., Visualizing the Effect of Gold Nanocages on Absorption, Imaging, and Lower Critical Solution Temperature Phase Transition of Individual Poly(NiPAM)-Based Hydrogel Particles by Near Infrared Multispectral Imaging Microscopy, Analytical Chemistry, 2011, 83(9):3520-3527.
Metcalf et al., Biofilm Delays Wound Healing: A Review of the Evidence, Burns & Trauma, 2013, 1(1):5-12.
Miao et al., Adsorption of Doxorubicin on Poly(Methyl Methacrylate)-Chitosan-Heparin-Coated Activated Carbon Beads, Langmuir, 2012, 28(9):4396-4403.
Mikhaylova et al., Preclinical Evaluation of Antimicrobial Efficacy and Biocompatibility of a Novel Bacterial Barrier Dressing, Wounds, 2011, 23(2):24-31.
Takagai et al., One-Pot Synthesis with in Situ Preconcentration of Spherical Monodispersed Gold Nanoparticles using Thermoresponsive 3-(Alkyldimethylammonio)-Propyl Sulfate Zwitterionic Surfactants, Chemical Communications, 2016, 5 pages.
Tamargo et al., The Role of Saposin C in Gaucher Disease, Molecular Genetics and Metabolism, 2012, 106(3):257-263.
Tamm et al., Infrared Spectroscopy of Proteins and Peptides in Lipid Bilayers, Quarterly Reviews of Biophysics, 1997, 30(4):365-429.
Tanabe et al., Preparation and Characterization of Keratin-Chitosan Composite Film, Biomaterials, 2002, 23(3):817-825.
The Free Dictionary by Farlex, Macrocycle, Retrieved from https://web.archive.org/web/20130722182508/https://www.thefreedictionary.com/macrocycle>, Accessed on Feb. 14, 2019, 2 pages.
Tirgar et al., Removal of Airborne Hexavalent Chromium Mist using Chitosan Gel Beads as a New Control Approach, International Journal of Environmental Science & Technology, 2006, 3(3):305-313.
Traber et al., Burn and Smoke Inhalation Injury in Sheep Depletes Vitamin E: Kinetic Studies using Deuterated Tocopherols, Free Radical Biology & Medicine, 2007, 42(9):1421-1429.

(56) References Cited

OTHER PUBLICATIONS

Traber et al., α-Tocopherol Adipose Tissue Stores are Depleted after Burn Injury in Pediatric Patients, The American Journal of Clinical Nutrition, 2010, 92(6):1378-1384.

Tran et al., Principles and Analytical Applications of Acousto-Optic Tunable Filters, An Overview, Talanta, 1997, 45(2):237-248.

Tran et al., Simultaneous Multispectral Imaging in the Visible and Near-Infrared Region: Applications in Document Authentication and Determination of Chemical Inhomogeneity of Copolymers, Analytical Chemistry, 1998, 70(22):4701-4708.

Tran et al., Visualizing Chemical Composition and Reaction Kinetics by the Near Infrared Multispectral Imaging Technique, Journal of Near Infrared Spectroscopy, 2000, 8(2):89-102.

Tran et al., Development and Analytical Applications of Multispectral Imaging Techniques: An Overview, Fresenius' Journal of Analytical Chemistry, 2001, 369:313-319.

Tran et al., Determination of Binding Constants of Cyclodextrins in Room-Temperature Ionic Liquids by Near-Infrared Spectrometry, Analytical Chemistry, 2002, 74(20):5337-5341.

Tran et al., Visualizing Chemical Compositions and Kinetics of Sol-Gel by Near-Infrared Multispectral Imaging Technique, Analytical Chemistry, 2002, 74(7):1604-1610.

Tran et al., Absorption of Water by Room-Temperature Ionic Liquids: Effect of Anions on Concentration and State of Water, Applied Spectroscopy, 2003, 57(2):152-157.

Tran, Infrared Multispectral Imaging: Principles and Instrumentation, Applied Spectroscopy Reviews, 2003, 38(2):133-153.

Tran et al., Chiral Ionic Liquid that Functions as Both Solvent and Chiral Selector for the Determination of Enantiomeric Compositions of Pharmaceutical Products, Analytical Chemistry, 2006, 78(4):1349-1356.

Tran, Ionic Liquids for and by Analytical Spectroscopy, Analytical Letters, 2007, 40(13):2447-2464.

Tran et al., Molecular State and Distribution of Fullerenes Entrapped in Sol-Gel Samples, The Journal of Physical Chemistry B, 2008, 112(46):14548-14559.

Tran et al., Development of a Universal Method Based on Ionic Liquids for Determination of Enantiomeric Compositions of Pharmaceutical Product, Ionic Liquid Applications: Pharmaceuticals, Therapeutics, and Biotechnology, American Chemical Society, 2010, Chapter 4, pp. 35-54.

Tran et al., Chitosan-Cellulose Composite Materials: Preparation, Characterization and Application for Removal of Microcystin, Journal of Hazardous Materials, 2013, 252:355-366.

Tran et al., Recyclable Synthesis, Characterization and Antimicrobial Activity of Chitosan-Based Polysaccharide Composite Materials, Journal of Biomedical Materials Research, Part A, 2013, 101(8):2248-2257.

Tran et al., Cellulose, Chitosan and Keratin Composite Materials, Controlled Drug Release, Langmuir, 2015, 31(4):1516-1526.

Tran et al., Cellulose, Chitosan and Keratin Composite Materials, Facile and Recyclable Synthesis, Conformation and Properties, ACS Sustainable Chemistry & Engineering, 2016, 4(3):1850-1861.

Tran et al., One-Pot Synthesis of Biocompatible Silver Nanoparticle Composites from Cellulose and Keratin: Characterization and Antimicrobial Activity, ACS Applied Materials & Interfaces, 2016, 8(50):34791-34801.

Tran et al., Synthesis, Structure and Antimicrobial Property of Green Composites from Cellulose, Wool, Hair and Chicken Feather, Carbohydrate Polymers, 2016, 151:1269-1276.

Tran et al., Biocompatible Copper Oxide Nanoparticle Composites from Cellulose and Chitosan: Facile Synthesis, Unique Structure, and Antimicrobial Activity, ACS Applied Materials & Interfaces, 2017, 9(49):42503-42515.

Tran et al., Facile Synthesis, Structure, Biocompatibility and Antimicrobial Property of Gold Nanoparticle Composites from Cellulose and Keratin, Journal of Colloid and Interface Science, 2018, 510:237-245.

Tran et al., Preliminary Results on Inhibition of Biofilm Formation, Retrived from https://www.marquette.edu/chemistry/directory/documents/tran-pub81.pdf, Jun. 17, 2019, 2 pages.

Uddin et al., Physical and Biochemical Characterization of Chemically-Treated Pollen Shells for Potential Use in Oral Delivery of Therapeutics, Journal of Pharmaceutical Sciences, 2018, 107(12):3047-3059.

Varshosaz et al., Designing of a Thermosensitive Chitosan/Poloxamer in Situ Gel for Ocular Delivery of Ciprofloxacin, The Open Drug Delivery Journal, 2008, 2(1):61-70.

Vasconcelos et al., The Use of Keratin in Biomedical Applications, Current Drug Targets, 2013, 14(5):612-619.

Venkateswarlu et al., Surfactant-Free Green Synthesis of Fe3O4 Nanoparticles Capped with 3, 4-Dihydroxyphenethylcarbamodithioate: Stable Recyclable Magnetic Nanoparticles for the Rapid and Efficient Removal of Hg(II) Ions from Water, Dalton Transactions, 2015, 44(42):18427-18437.

Verma et al., Preparation of Scaffolds from Human Hair Proteins for Tissue-Engineering Applications, Biomedical Materials, 2008, 3(2):025007, pp. 1-12.

Vig et al., Respiratory Syncytial Virus Inhibition by Gold and Titanium Nanoparticles, NSTI-Nanotech 2009, 2:139-142.

Vijayakumar et al., Gold Nanoparticles as an HIV Entry Inhibitor, Current HIV Research, 2012, 10(8):643-646.

Vilaplana et al., Environmental and Resources Aspects of Sustainable Biocomposites, Polymer Degradation and Stability, 2010, 95(11):2147-2161.

Vonnemann et al., Virus Inhibition Induced by Polyvalent Nanoparticles of Different Sizes, Nanoscale, 2014, 6(4):2353-2360.

Wang et al., Multivalent Glyconanoparticles with Enhanced Affinity to the Anti-Viral Lectin Cyanovirin-N, Chemical Communications, 2011, 47(30):8620-8622.

Wang et al., pH-Dependent Evolution of Five-Star Gold Nanostructures: An Experimental and Computational Study, ACS Nano, 2013, 7(3):2258-2265.

Wang et al., The Mouse Excisional Wound Splinting Model, Including Applications for Stem Cell Transplantation, Nature Protocols, 2013, 8(2):302-309.

Wang et al., Preparation of Hybrid Gold/Polymer Nanocomposites and their Application in a Controlled Antibacterial Assay, ACS Applied Materials & Interfaces, 2016, 8(42):29101-29109.

Wang et al., Construction of Cellulose/ZnO Composite Microspheres in NaOH/Zinc Nitrate Aqueous Solution Via One-Step Method, Cellulose, 2019, 26(1):557-568.

Warner et al., Perspectives on Moving Ionic Liquid Chemistry into the Solid Phase, Analytical Chemistry, 2014, 86(15):7184-7191.

Watters et al., Enzymatic Degradation of in Vitro *Staphylococcus aureus* Biofilms Supplemented with Human Plasma, Infection and Drug Resistance, 2016, 9:71-78.

Wei et al., The Synthesis of Chitosan-Based Silver Nanoparticles and their Antibacterial Activity, Carbohydrate Research, 2009, 344(17):2375-2382.

Weingarten et al., Prediction of Wound Healing in Human Diabetic Foot Ulcers by Diffuse Near-Infrared Spectroscopy: A Pilot Study, Wound Repair and Regeneration, 2010, 18(2):180-185.

Weinreb et al., Long-Term Clinical Outcomes in Type 1 Gaucher Disease Following 10 Years of Imiglucerase Treatment, Journal of Inherited Metabolic Disease, 2013, 36:543-553.

Welton, Room-Temperature Ionic Liquids: Solvents for Synthesis and Catalysis, Chemical Reviews, 1999, 99(8):2071-2083.

Westad et al., Variable Selection in Near Infrared Spectroscopy Based on Significance Testing in Partial Least Squares Regression, Journal of Near Infrared Spectroscopy, 2000, 8(2):117-124.

Westad et al., Finding Relevant Spectral Regions Between Spectroscopic Techniques by Use of Cross Model Validation and Partial Least Squares Regression, Analytica Chimica Acta, 2007, 595(1-2):323-327.

Westad et al., Incorporating Chemical Band-Assignment in Near Infrared Spectroscopy Regression Models, Journal of Near Infrared Spectroscopy, 2008, 16(3):265-273.

Westrick et al., A Review of Cyanobacteria and Cyanotoxins Removal/Inactivation in Drinking Water Treatment, Analytical and Bioanalytical Chemistry, 2010, 397:1705-1714.

(56) References Cited

OTHER PUBLICATIONS

Wikipedia, Composite Material, Retrieved from https://en.wikipedia.org/wiki/Composite_material, Accessed on Aug. 21, 2019, 1 page.
Williams et al., Dual-Band MWIR/LWIR Radiometer for Absolute Temperature Measurements, Thermosense XXVIII, SPIE, 2006, 6205, 13 pages.
Wishart et al., The 13C Chemical-Shift Index: A Simple Method for the Identification of Protein Secondary Structure using 13C Chemical-Shift Data, Journal of Biomolecular NMR, 1994, 4:171-180.
Wittaya-Areekul et al., Development and in Vitro Evaluation of Chitosan-Polysaccharides Composite Wound Dressings, International Journal of Pharmaceuticals, 2006, 313(1-2):123-128.
Wold et al., PLS-Regression: A Basic Tool of Chemometrics, Chemometrics and Intelligent Laboratory Systems, 2001, 58(2):109-130.
Wound Source, 3M™ Silvercel™ Non-Adherent Antimicrobial Alginate Dressing with 3M™ Easylift™ Precision Film Technology, Copyright 2008-2023 HMP Global, Inc., Retrieved from https://www.woundsource.com/product/3m-silvercel-non-adherent-antimicrobial-alginate-dressing-easylift-precision-film-technology, 7 pages.
Wright et al., Soft-and Hard-Templated Organic Salt Nanoparticles with the Midas Touch: Gold-Shelled NanoGUMBOS, Journal of Materials Chemistry C, 2014, 11 pages.
Wright et al., Cooling of Burns: Mechanisms and Models, Burns, 2015, 41(5):882-889.
Wu et al., Cellulose/Soy Protein Isolate Blend Films Prepared via Room-Temperature Ionic Liquid, Industrial & Engineering Chemistry Research, 2009, 48(15):7132-7136.
Wu et al., In Situ Synthesis of Silver-Nanoparticles/Bacterial Cellulose Composites for Slow-Released Antimicrobial Wound Dressing, Carbohydrate Polymers, 2014, 102:762-771.
Xia et al., Recent Developments in Shape-Controlled Synthesis of Silver Nanocrystals, The Journal of Physical Chemistry C, 2012, 116(41):21647-21656.
Xiao et al., Dissolution and Blending of Chitosan using 1,3-Dimethylimidazolium Chloride and 1-H-3-Methylimidazolium Chloride Binary Ionic Liquid Solvent, Carbohydrate Polymers, 2011, 83(1):233-238.
Xie et al., Ionic Liquids as Novel Solvents for the Dissolution and Blending of Wool Keratin Fibers, Green Chemistry, 2005, 7(8):606-608.
Xu et al., Biological Evaluation of Human Hair Keratin Scaffolds for Skin Wound Repair and Regeneration, Materials Science and Engineering: C, 2013, 33(2):648-655.
Yamada et al., DNA-Cyclodextrin-Inorganic Hybrid Material for Absorbent of Various Harmful Compounds, Materials Chemistry and Physics, 2011, 126(1-2):278-283.
Yan et al., Plankton Community Succession in Artificial Systems Subjected to Cyanobacterial Blooms Removal Using Chitosan Modified Soils, Microbial Ecology, 2009, 58:47-55.
Yang et al., Gold Nanomaterials at Work in Biomedicine, Chemical Reviews, 2015, 115(19):10410-10488.
Yang et al., Nitric Oxide Based Strategies for Applications of Biomedical Devices, Biosurface and Biotribology, 2015, 1(3):177-201.
Yilmaz et al., Enantioselective Hydrolysis of Racemic Naproxen Methyl Ester with Sol-Gel Encapsulated Lipase in the Presence of Sporopollenin, Journal of Molecular Catalysis B: Enzymatic, 2010, 62(2):162-168.
Yin et al., Study on Effective Extraction of Chicken Feather Keratins and their Films for Controlling Drug Release, Biomaterials Science, 2013, 1(5):528-536.
Zegura et al., Genotoxicity and Potential Carcinogenicity of Cyanobacterial Toxins—A Review, Mutation Research/Reviews in Mutation Research, 2011, 727(1-2):16-41.
Zhang et al., 1-Allyl-3-Methylimidazolium Chloride Room Temperature Ionic Liquid: A New and Powerful Nonderivatizing Solvent for Cellulose, Macromolecules, 2005, 38(20):8272-8277.
Zhang et al., Crystallization and Prevention of Supercooling of Microencapsulated N-Alkanes, Journal of Colloid and Interface Science, 2005, 281(2):299-306.
Zhang et al., Antibacterial Activity of Cyclodextrins Against Bacillus Strains, Archives of Microbiology, 2008, 190(5):605-609.
Zhang et al., Fabrication and Performances of Microencapsulated Phase Change Materials Based on N-Octadecane Core and Resorcinol-Modified Melamine-Formaldehyde Shell, Colloids and Surfaces A: Physicochemical and Engineering Aspects, 2009, 332(2-3):129-138.
Zhang et al., Synthesis and Properties of Microencapsulated N-Octadecane with Polyurea Shells Containing Different Soft Segments for Heat Energy Storage and Thermal Regulation, Solar Energy Materials and Solar Cells, 2009, 93(8):1366-1376.
Zhang et al., CuO Nanostructures: Synthesis, Characterization, Growth Mechanisms, Fundamental Properties, and Applications, Progress in Materials Science, 2014, 60:208-337.
Zhang et al., Design and Synthesis of Multifunctional Microencapsulated Phase Change Materials with Silver/Silica Double-Layered Shell for Thermal Energy Storage, Electrical Conduction and Antimicrobial Effectiveness, Energy, 2016, 111:498-512.
Zhao et al., Review on Microencapsulated Phase Change Materials (MEPCMs): Fabrication, Characterization and Applications, Renewable and Sustainable Energy Reviews, 2011, 15(8):3813-3832 [in two parts due to file size].
Zhao et al., Sustainable and Practical Utilization of Feather Keratin by an Innovative Physicochemical Pretreatment: High Density Steam Flash-Explosion, Green Chemistry, 2012, 14(12):3352-3360.
Zheng et al., Removal of Chlorophenols from Groundwater by Chitosan Sorption, Water Research, 2004, 38(9):2315-2322.
Zheng et al., Polysaccharide-Based Nanocomposites and their Applications, Carbohydrate Research, 2015, 405:23-32.
Zou et al., Removal of Cyanobacterial Blooms in Taihu Lake Using Local Soils, II, Effective Removal of Microcystis Aeruginosa Using Local Soils and Sediments Modified by Chitosan, Environmental Pollution, 2006, 141(2):201-205.
European Patent Office, Partial Supplementary European Search Report, Application No. 14797027.1, Dec. 22, 2016, 6 pages.
European Patent Office, Extended European Search Report, Application No. 14797027.1, Apr. 11, 2017, 4 pages.
European Patent Office, Extended European Search Report, Application No. 17764084.4, Oct. 31, 2019, 4 pages.
European Patent Office, Extended European Search Report, Application No. 17862605.7, May 11, 2020, 4 pages.
PCT International Search Report and Written Opinion, PCT/US2014/038381, Oct. 16, 2014, 8 pages.
PCT International Search Report and Written Opinion, PCT/US2017/021552, Jun. 8, 2017, 11 pages.
PCT International Search Report and Written Opinion, PCT/US2017/057134, Feb. 7, 2018, 8 pages.
PCT International Search Report and Written Opinion, PCT/US2020/038184, Sep. 24, 2020, 12 pages.
Jacob et al., Encapsulation of High-Temperature Phase Change Materials, High-Temperature Thermal Storage Systems using Phase Change Materials, 2018, Chapter 9, pp. 231-274, in Cabeza, editor, High-Temperature Thermal Storage Systems using Phase Change Materials, Academic Press.
Chowdhury et al., Biosorption of Basic Green 4 from Aqueous Solution by *Ananas comosus* (Pineapple) Leaf Powder, Colloids and Surfaces B: Biointerfaces, 2011, 84(2):520-527.
Cilurzo et al., Regenerated Keratin Proteins as Potential Biomaterial for Drug Delivery, Polymers for Advanced Technologies, 2013, 24(11):1025-1028.
Combat Medical, Our Process, Copyright Combat Medical 2023, Retrieved from https://combatmedical.com/our-process/, 3 pages.
Conte et al., Modifications of the Metal and Support during the Deactivation and Regeneration of Au/C Catalysts for the Hydrochlorination of Acetylene, Catalysis Science & Technology, 2013, 3:128-134.
Convatec, Aquacel® Family of Dressings, Copyright 2022 Convatec, Inc., Retrieved from https://www.convatec.com/advanced-wound-care/aquacel-family-of-dressings/, 4 pages.

(56) References Cited

OTHER PUBLICATIONS

Corliss et al., Preserving the Inflated Structure of Lyophilized Sporopollenin Exine Capsules with Polyethylene Glycol Osmolyte, Journal of Industrial and Engineering Chemistry, 2018, 61:255-264.
Costa et al., Modeling and Comparison of Dissolution Profiles, European Journal of Pharmaceutical Sciences, 2001, 13(2):123-133.
Costerton et al., Bacterial Biofilms: A Common Cause of Persistent Infections, Science, 1999, 284:1318-1322.
Crane et al., Monitoring the Healing of Combat Wounds using Raman Spectroscopic Mapping, Wound Repair and Regeneration, 2010, 18(4):409-416.
Crane et al., Profiling Wound Healing with Wound Effluent: Raman Spectroscopic Indicators of Infection, Proceedings of SPIE—The International Society for Optical Engineering, 2012, 8220, 9 pages.
Crane et al., Raman Spectroscopic Analysis of Combat-Related Heterotopic Ossification Development, Bone, 2013, 57(2):335-342.
Crini, Recent Developments in Polysaccharide-Based Materials Used as Adsorbents in Wastewater Treatment, Progress in Polymer Science, 2005, 30(1):38-70.
Cui et al., Transglutaminase-Modified Wool Keratin Film and its Potential Application in Tissue Engineering, Engineering in Life Sciences, 2013, 13(2):149-155.
Da Roz et al., Adsorption of Chitosan on Spin-Coated Cellulose Films, Carbohydrate Polymers, 2010, 80(1):65-70.
Da Silva Ferreira et al., Green Production of Microalgae-Based Silver Chloride Nanoparticles with Antimicrobial Activity Against Pathogenic Bacteria, Enzyme and Microbial Technology, 2017, 97:114-121.
Dai et al., Chitosan Acetate Bandage as a Topical Antimicrobial Dressing for Infected Burns, Antimicrobial Agents and Chemotherapy, 2009, 53(2):393-400.
De Alvarenga, Characterization and Properties of Chitosan, Biotechnology of Biopolymers, 2011, 91:91-108.
De Guzman et al., Mechanical and Biological Properties of Keratose Biomaterials, Biomaterials, 2011, 32(32):8205-8217.
Deng et al., Superparamagnetic High-Magnetization Microspheres with an Fe3O4@SiO2 Core and Perpendicularly Aligned Mesoporous SiO2 Shell for Removal of Microcystins, Journal of the American Chemical Society, 2008, 130(1):28-29.
Dhakal et al., Synthesis of Unconventional Materials using Chitosan and Crown Ether for Selective Removal of Precious Metal Ions, World Academy of Science, Engineering and Technology, 2009, 56:204-208.
Dhas et al., Facile Synthesis of Silver Chloride Nanoparticles using Marine Alga and its Antibacterial Efficacy, Spectrochimica Acta Part A: Molecular and Biomolecular Spectroscopy, 2014, 120:416-420.
Diego-Taboada et al., Protein Free Microcapsules Obtained from Plant Spores as a Model for Drug Delivery: Ibuprofen Encapsulation, Release and Taste Masking, Journal of Materials Chemistry B, 2013, 1(5):707-713.
Ditta et al., Photocatalytic Antimicrobial Activity of Thin Surface Films of TiO 2, CuO and TiO 2/CuO Dual Layers on *Escherichia coli* and Bacteriophage T4, Applied Microbiology and Biotechnology, 2008, 79:127-133.
Do et al., Phase-Change Core/Shell Structured Nanofibers Based on Eicosane/Poly(vinylidene fluoride) for Thermal Storage Applications, Korean Journal of Chemical Engineering, 2013, 30(7):1403-1409.
Docherty et al., Toxicity and Antimicrobial Activity of Imidazolium and Pyridinium Ionic Liquids, Green Chemistry, 2005, 7(4):185-189.
Dousseau et al., Determination of the Secondary Structure Content of Proteins in Aqueous Solutions from their Amide I and Amide II Infrared Bands, Comparison between Classical and Partial Least-Squares Methods, Biochemistry, 1990, 29(37):8771-8779.
Dreve et al., Chitosan-Based Delivery Systems for Diclofenac Delivery: Preparation and Characterization, Journal of Physics: Conference Series, 2009, 182:012065, pp. 1-4.

Dubinin, The Potential Theory of Adsorption of Gases and Vapours for Adsorbents with Energetically Non-Uniform Surfaces, Chemical Reviews, 1960, 60(2):235-241.
Duong et al., Nanoparticle (Star Polymer) Delivery of Nitric Oxide Effectively Negates Pseudomonas Aeruginosa Biofilm Formation, Biomacromolecules, 2014, 15(7):2583-2589.
Duri et al., Determination of Chemical Homogeneity of Fire Retardant Polymeric Nanocomposite Materials by Near-Infrared Multispectral Imaging Microscopy, Analytical Letters, 2010, 43(10-11):1780-1789.
Duri et al., Polysaccharide Ecocomposite Materials: Synthesis, Characterization and Application for Removal of Pollutants and Bacteria, ECS Transactions, 2013, 50(11):573-594.
Duri et al., Supramolecular Composite Materials from Cellulose, Chitosan, and Cyclodextrin: Facile Preparation and their Selective Inclusion Complex Formation with Endocrine Disruptors, Langmiur, 2013, 29(16):5037-5049.
Duri et al., Enantiomeric Selective Adsorption of Amino Acid by Polysaccharide Composite Materials, Langmuir, 2014, 30(2):642-650.
Duri et al., Composites Containing Fullerenes and Polysaccharides: Green and Facile Synthesis, Biocompatibility and Antimicrobial Activity, ACS Sustainable Chemistry & Engineering, 2017, 5(6):5408-5417.
Dyab et al., Encapsulation of Erythromycin and Bacitracin Antibiotics into Natural Sporopollenin Microcapsules: Antibacterial, Cytotoxicity, In Vitro and In Vivo Release Studies for Enhanced Bioavailability, RSC Advances, 2018, 8(58):33432-33444.
El-Hefian et al., Rheological and Morphological Studies of Chitosan/Agar/Poly (Vinyl Alcohol) Blends, Journal of Applied Sciences Research, 2010, 6(5):460-468.
Ellis, Infra-Red Absorption by the N-H Bond II in Aryl, Alkyl and Aryl-Alkyl Amines, Journal of the American Chemical Society, 1928, 50(3):685-695.
El-Mekawy et al., Preparation of Chitosan Films Mixed with Superabsorbent Polymer and Evaluation of its Haemostatic and Antibacterial Activities, Journal of Applied Polymer Sciences, 2010, 116(6):3489-3496.
El-Tahlawy et al., Novel Method for Preparation of β-Cyclodextrin/Grafted Chitosan and its Application, Carbohydrate Polymers, 2006, 63(3):385-392.
Eroy-Reveles et al., Near-Infrared Light Activated Release of Nitric Oxide from Designed Photoactive Manganese Nitrosyls: Strategy, Design, and Potential as NO Donors, Journal of the American Chemical Society, 2008, 130(13):4447-4458.
Eser et al., Antimicrobial Activity of Copper Alloys Against Invasive Multidrug-Resistant Nosocomial Pathogens, Current Microbiology, 2015, 71:291-295.
Fakayode et al., Multicomponent Analyses of Chiral Samples by Use of Regression Analysis of UV-Visible Spectra of Cyclodextrin Guest-Host Complexes, Analytical and Bioanalytical Chemistry, 2009, 394:1645-1653.
Fan et al., Extraction of Cage-Like Sporopollenin Exine Capsules from Dandelion Pollen Grains, Scientific Reports, 2018, 8(1):6565, pp. 1-11.
Fan et al., Transformation of Hard Pollen into Soft Matter, Nature Communications, 2020, 11(1):1449, pp. 1-10.
Fang et al., Characterization and Evaluation of Silk Protein Hydrogels for Drug Delivery, Chemical and Pharmaceutical Bulletin, 2006, 54(2):156-162.
Fang et al., Ultrasonic Synthesis and Characterization of Polystyrene/N-Dotriacontane Composite Nanoencapsulated Phase Change Material for Thermal Energy Storage, Applied Energy, 2014, 132:551-556.
Fayaz et al., Inactivation of Microbial Infectiousness by Silver Nanoparticles-Coated Condom: A New Approach to Inhibit HIV- and HSV-Transmitted Infection, International Journal of Nanomedicine, 2012, 7:5007-5018.
Fendt et al., Viscosities of Acetate or Chloride-Based Ionic Liquids and Some of their Mixtures with Water or Other Common Solvents, Journal of Chemical & Engineering Data, 2011, 56(1):31-34.

(56) References Cited

OTHER PUBLICATIONS

Feng et al., Near-Infrared Hyperspectral Imaging and Partial Least Square Regression for Rapid and Reagentless Determination of Enterobacteriaceae on Chicken Fillet, Food Chemistry, 2013, 138(2-3):1829-1836.
Fink et al., Structure Formation of Regenerated Cellulose Materials from NMMO—Solutions, Progress in Polymer Science, 2001, 26(9):1473-1524.
Petruzzi et al., Biofilm Formation and Avian Immune Response Following Experimental Acute and Chronic Avian Cholera due to Pasteurella Multocida, Veterinary Microbiology, 2018, 222:114-123.
Phaechamud et al., Antibacterial Activity and Drug Release of Chitosan Sponge Containing Doxycycline Hyclate, AAPS PharmSciTech, 2008, 9(3):829-835.
Pinkert et al., Ionic Liquids and their Interaction with Cellulose, Chemical Reviews, 2009, 109(12):6712-6728.
Poduri et al., *Citrullus lanatus* 'Sentinel' (Watermelon) Extract Reduces Atherosclerosis in LDL Receptor-Deficient Mice, The Journal of Nutritional Biochemistry, 2013, 24(5):882-886.
Pope et al., Absorption Spectrum (380-700 nm) of Pure Water, II, Integrating Cavity Measurements, Applied Optics, 1997, 36(33):8710-8723.
Prahl, Optical Absorption of Hemoglobin, Retrieved from https://omlc.org/spectra/hemoglobin/index.html, 1998, 4 pages.
Prahl, Tabulated Molar Extinction Coefficient for Hemoglobin in Water, Retrieved from https://omlc.org/spectra/hemoglobin/summary.html, 1998, 7 pages.
Pusateri et al., Effect of a Chitosan-Based Hemostatic Dressing on Blood Loss and Survival in a Model of Severe Venous Hemorrhage and Hepatic Injury in Swine, Journal of Trauma and Acute Care Surgery, 2003, 54(1):177-182.
Pyo et al., Adsorption of Microcystin LR by Activated Carbon Fibers, Bulletin of the Korean Chemical Society, 2005, 26(12):2089-2092.
Rabea et al., Chitosan as Antimicrobial Agent: Applications and Mode of Action, Biomacromolecules, 2003, 4(6):1457-1465.
Raffi et al., Investigations into the Antibacterial Behavior of Copper Nanoparticles Against *Escherichia coli*, Annals of Micriobiology, 2010, 60(1):75-80.
Rebek, Jr., Introduction to the Molecular Recognition and Self-Assembly Special Feature, Proceedings of the National Academy of Sciences, 2009, 106(26):10423-10424.
Rebek, Jr., Molecular Behavior in Small Spaces, Accounts of Chemical Research, 2009, 42(10):1660-1668.
Reddy et al., Bio-Thermoplastics from Grafted Chicken Feathers for Potential Biomedical Applications, Colloids and Surfaces B: Biointerfaces, 2013, 110:51-58.
Reichl, Films Based on Human Hair Keratin as Substrates for Cell Culture and Tissue Engineering, Biomaterials, 2009, 30(36):6854-6866.
Ribeiro et al., Burn Wounds Infected by Contaminated Water: Case Reports, Review of the Literature and Recommendations for Treatments, Burns, 2010, 36(1):9-22.
Rimando et al., Determination of Citrulline in Watermelon Rind, Journal of Chromatography A, 2005, 1078(1-2):196-200.
Ritger et al., A Simple Equation for Description of Solute Release I: Fickian and Non-Fickian Release from Non-Swellable Devices in the Form of Slabs, Spheres, Cylinders, or Discs, Journal of Controlled Release, 1987, 5(1):23-36.
Ropel et al., Octanol-Water Partition Coefficients of Imidazolium-Based Ionic Liquids, Green Chemistry, 2005, 7(2):83-90.
Rosewald et al., Cellulose-Chitosan-Keratin Composite Materials: Synthesis, Immunological and Antibacterial Properties, ECS Transactions, 2014, 64(4):499-505.
Rossi et al., Analysis of Protein-Ligand Interactions by Fluorescence Polarization, Nature Protocols, 2011, 6(3):365-387.
Rouse et al., A Review of Keratin-Based Biomaterials for Biomedical Applications, Materials, 2010, 3(2):999-1014.
Rowan et al., Burn Wound Healing and Treatment: Review and Advancements, Critical Care, 2015, 19:1-12.
Samano-Valencia et al., Characterization and Biocompatibility of Chitosan Gels with Silver and Gold Nanoparticles, Journal of Nanomaterials, 2014, 2014:543419, pp. 1-11.
Sametband et al., Effective Multi-Strain Inhibition of Influenza Virus by Anionic Gold Nanoparticles, MedChemComm, 2011, 2(5):421-423.
Sando et al., Photochemical crosslinking of soluble wool keratins produces a mechanically stable biomaterial that supports cell adhesion and proliferation, Journal of Biomedical Materials Research, Part A, 2010, 95(3):901-911.
Sardar et al., Spectroscopic and Microscopic Investigation of Gold Nanoparticle Formation: Ligand and Temperature Effects on Rate and Particle Size, Journal of the American Chemical Society, 2011, 133(21):8179-8190.
Sari et al., Preparation, Characterization and Thermal Properties of PMMA/N-Heptadecane Microcapsules as Novel Solid-Liquid MicroPCM for Thermal Energy Storage, Applied Energy, 2010, 87(5):1529-1534.
Sathishkumar et al., Immobilization of Silver Nanoparticles Synthesized using Curcuma Longa Tuber Powder and Extract on Cotton Cloth for Bactericidal Activity, Biosource Technology, 2010, 101(20):7958-7965.
Saul et al., Keratin Hydrogels Support the Sustained Release of Bioactive Ciprofloxacin, Journal of Biomedical Materials Research, Part A, 2011, 98(4):544-553.
Sen et al., Human Skin Wounds: A Major and Snowballing Threat to Public Health and the Economy, Wound Repair and Regeneration, 2009, 17(6):763-771.
Sharma et al., Fabrication of Antibacterial Silver Nanoparticle—Sodium Alginate—Chitosan Composite Films, RSC Advances, 2012, 2(13):5837-5843.
Shekhter et al., Beneficial Effect of Gaseous Nitric Oxide on the Healing of Skin Wounds, Nitric Oxide, 2005, 12(4):210-219.
Silverlon, Silverlon Acute Burn Glove Dressings, LC-CE-IFU-ABG, 2005, 3 pages.
Singaravelu et al., Novel Extracellular Synthesis of Monodisperse Gold Nanoparticles Using Marine Alga, Sargassum Wightii Greville, Colloids and Surfaces B: Biointerfaces, 2007, 57(1):97-101.
Siripatrawan et al., Rapid Detection of *Escherichia coli* Contamination in Packaged Fresh Spinach Using Hyperspectral Imaging, Talanta, 2011, 85(1):276-281.
Sirota et al., Rotator Phases of the Normal Alkanes: An X-ray Scattering Study, The Journal of Chemical Physics, 1993, 98(7):5809-5824.
Sirota et al., Phase Transitions Among Rotator Phases of the Normal Alkanes, The Journal of Chemical Physics, 1994, 101(12):10873-10882.
Sohrabnezhad et al., Spectroscopic Study of Silver Halides in Montmorillonite and their Antibacterial Activity, Journal of Photochemistry and Photobiology B: Biology, 2016, 163:150-155.
Soni et al., Isolation of Sporopollenin-Like Biopolymer from Aspergillus Niger and its Characterisation, Chemical Papers, 2016, 70(12):1556-1567.
Soukup-Hein et al., Ionic Liquids in Analytical Chemistry, Annual Review of Analytical Chemistry, 2009, 2:145-168.
Souza et al., Study of Enzyme Replacement Therapy for Gaucher Disease: Comparative Analysis of Clinical and Laboratory Parameters at Diagnosis and After Two, Five and Ten Years of Treatment, Brazilian Journal of Hematology and Hemotherapy, 2014, 36(5):345-350.
Stuart et al., Emerging Applications of Stimuli-Responsive Polymer Materials, Nature Materials, 2010, 9(2):101-113.
Su et al., Crystallization Features of Normal Alkanes in Confined Geometry, Accounts of Chemical Research, 2014, 47(1):192-201.
Sule et al., A Combination of Assays Reveals Biomass Differences in Biofilms Formed by *Escherichia coli* Mutants, Letters in Applied Microbiology, 2009, 49(3):299-304.
Sullivan, Solid-Phase Behavior of Several Long-Chain n-Paraffins, Esters, and a Ketone, Journal of Research of the National Bureau of Standards, Section A, Physics and Chemistry, 1974, 78A(2):129-141.

(56) References Cited

OTHER PUBLICATIONS

Sun et al., Ionic Liquids in Analytical Chemistry, Analytica Chimica Acta, 2009, 48 pages.
Sundaram et al., Classification and Structural Analysis of Live and Dead *Salmonella* Cells Using Fourier Transform Infrared Spectroscopy and Principle Component Analysis, Journal of Agricultural and Food Chemistry, 2012, 60(4):991-1004.
Svircev et al., Freshwater Cyanobacterial Blooms and Primary Liver Cancer Epidemiological Studies in Serbia, Journal of Environmental Science and Health, Part C, 2009, 27(1):36-55.
Swatloski et al., Dissolution of Cellulose with Ionic Liquids, Journal of the American Chemical Society, 2002, 124(18):4974-4975.

\* cited by examiner

MATERIALS BASED ON NATURAL POLLEN GRAINS AND USES THEREOF

CROSS-REFERENCE TO RELATED PATENT APPLICATIONS

This application represents the U.S. national stage entry of International Application No. PCT/US2020/038184 filed Jun. 17, 2020, which claims the benefit of priority under 35 U.S.C. § 119 (e) to U.S. Provisional Application No. 62/862,270, filed on Jun. 17, 2019, the contents of which are incorporated herein by reference in their entireties.

BACKGROUND

The field of the invention relates to composite materials containing structural polysaccharides, structural proteins, and sporopollenin exine capsules (SECs), and ionic liquid compositions for preparing the composite materials. In particular, in one embodiment, the field of the invention relates to composite materials containing structural polysaccharides, such as cellulose, chitin, or chitosan, structural proteins, such as keratin, and sporopollenin exine capsules (SECs) encapsulating various materials, which composite materials are formed from ionic liquid compositions. In another embodiment, the field of the invention relates to the use of SECs to encapsulate useful materials, such as flame retardant materials, phase change materials, and therapeutic materials, such as probiotics and prebiotics.

SUMMARY

Disclosed are materials related to sporopollenine exine capsules (SECs) and methods for preparing such materials. In one embodiment, the disclosed subject matter relates to methods for preparing SECs which can be utilized for encapsulating useful materials, such as flame retardant materials, phase change materials, and therapeutic materials, such as probiotics and prebiotics.

In another embodiment, the present invention relates to methods for preparing a composite material comprising one or more structural polymers and SECs which may be utilized to encapsulate one or more useful materials. Suitable structural polymers may include structural polysaccharides, structural proteins, or mixtures thereof. Preferably, the encapsulated materials within the SECs are probiotics, prebiotics, phase changing materials, and/or fire retardant changing materials.

The composite materials may be prepared from ionic liquid compositions comprising the one or more structural polymers and the SECs combined in the one or more ionic liquids forming the liquid ionic composition. The composite materials may be prepared from the ionic liquid compositions, for example, by removing the ionic liquid from the ionic liquid composition and retaining the one or more structural polymers, and the SECs.

The disclosed composite materials comprise SECs obtained from washing natural pollen grains with an organic solvent such as acetone, followed by washing with an acid, and finalizing the wash with a strong alkaline solution. Suitable natural pollen grains may include, but are not limited to, *Lycopodium clavatum*, sunflower (*Helianthus annuus*), short ragweed (*Ambrosia artemisiifolia*), black alder (*Alnus glutinosa*), and cottonwood or necklace poplar (*Populus deltoides*).

Suitable acids may include, but are not limited to, phosphoric acid, sulfuric acid, and hydrochloric acid. Suitable strong alkalines may include, but are not limited to, potassium hydroxide and sodium hydroxide.

The disclosed composite materials typically comprise one or more structural polymers. Suitable structural polymers may include, but are not limited to, structural polysaccharides, structural proteins, or mixtures thereof.

Suitable polysaccharides may include, but are not limited to polymers such as polysaccharides comprising monosaccharides linked via beta-1,4 linkages. For example, suitable structural polysaccharides may include polymers of 6-carbon monosaccharides linked via beta-1,4 linkages. Suitable structural polysaccharides for the disclosed compositions and composites may include, but are not limited to cellulose, chitin, and modified forms of chitin such as chitosan.

The disclosed compositions and composites preferably comprise one or more structural proteins. Suitable structural proteins may include, but are not limited to, keratin. Natural components that comprise keratin may be used to prepare the disclosed composite materials include wool, human hair, and/or chicken feathers.

The disclosed composite materials may be formed from ionic liquid compositions, for example, ionic liquid compositions comprising the one or more structural polymers dissolved in one or more ionic liquids to form an ionic liquid composition, where preferably, the one or more nitric acid releasing compounds are added to the ionic liquid composition. Suitable ionic liquids for forming the ionic liquid compositions may include but are not limited to alkylated imidazolium salts. In some embodiments, the alkylated imidazolium salt is selected from a group consisting of 1-butyl-3-methylimidazolium salt, 1-ethyl-3-methylimidazolium salt, and 1-allyl-3-methylimidazolium salt. Suitable salts may include, but are not limited to chloride salts.

In the disclosed ionic liquid compositions, a structural polysaccharide may be dissolved in an ionic liquid. In some embodiments, the ionic liquid may comprise at least about 2%, 4%, 6%, 8%, 10%, 15%, 20% w/w, dissolved structural polysaccharide.

In the disclosed ionic liquid compositions, a structural protein may be dissolved in the ionic liquid. In some embodiments, the ionic liquid may comprise at least about 2%, 4%, 6%, 8%, 10%, 15%, 20% w/w, dissolved structural protein.

The disclosed ionic liquid compositions may be utilized in methods for preparing the disclosed composite materials that comprise a structural polymer and SECs. For example, in the disclosed methods, a composite material comprising a structural polysaccharide and/or a structural protein, and SECs may be prepared by: (1) obtaining SECs from washing natural pollen grains as disclosed herein; (2) obtaining or preparing an ionic liquid composition as disclosed herein comprising a structural polysaccharide and/or a structural protein, where the structural polysaccharide and/or the structural protein are dissolved in an ionic liquid to form an ionic liquid composition; (3) adding empty or encapsulated SECs to the ionic liquid composition; (3) removing the ionic liquid from the ionic liquid composition; and (4) retaining the structural polysaccharide and/or the structural protein, and the empty or encapsulated SECs as a composite material.

The ionic liquid may be removed from the ionic liquid compositions by steps that include, but are not limited to washing (e.g., with an aqueous solution). The water remaining in the composite materials after washing may be removed from the composite materials by steps that include, but are not limited to drying (e.g., in air) and lyophilizing (i.e., drying under a vacuum). The composite material may be formed into any desirable shape, for example, a film and/or fabric material.

The composite materials may be utilized to produce temperature-regulating materials wherein, the composite material may contain phase change materials encapsulated into SECs. For example, the composite material may be utilized in the production of temperature-regulating materials, such as textiles or building materials. As such, the composite material may be utilized in building materials or textiles requiring building- or body-temperature control.

In other embodiments, the composite materials may be utilized to carry and release a compound. For example, the composite materials may be utilized to carry and release a compound gradually over an extended period of time (e.g., probiotic and/or prebiotic). As such, the composite material may be utilized in food products requiring delivery of probiotics and/or prebiotics.

DETAILED DESCRIPTION

Figure 1:
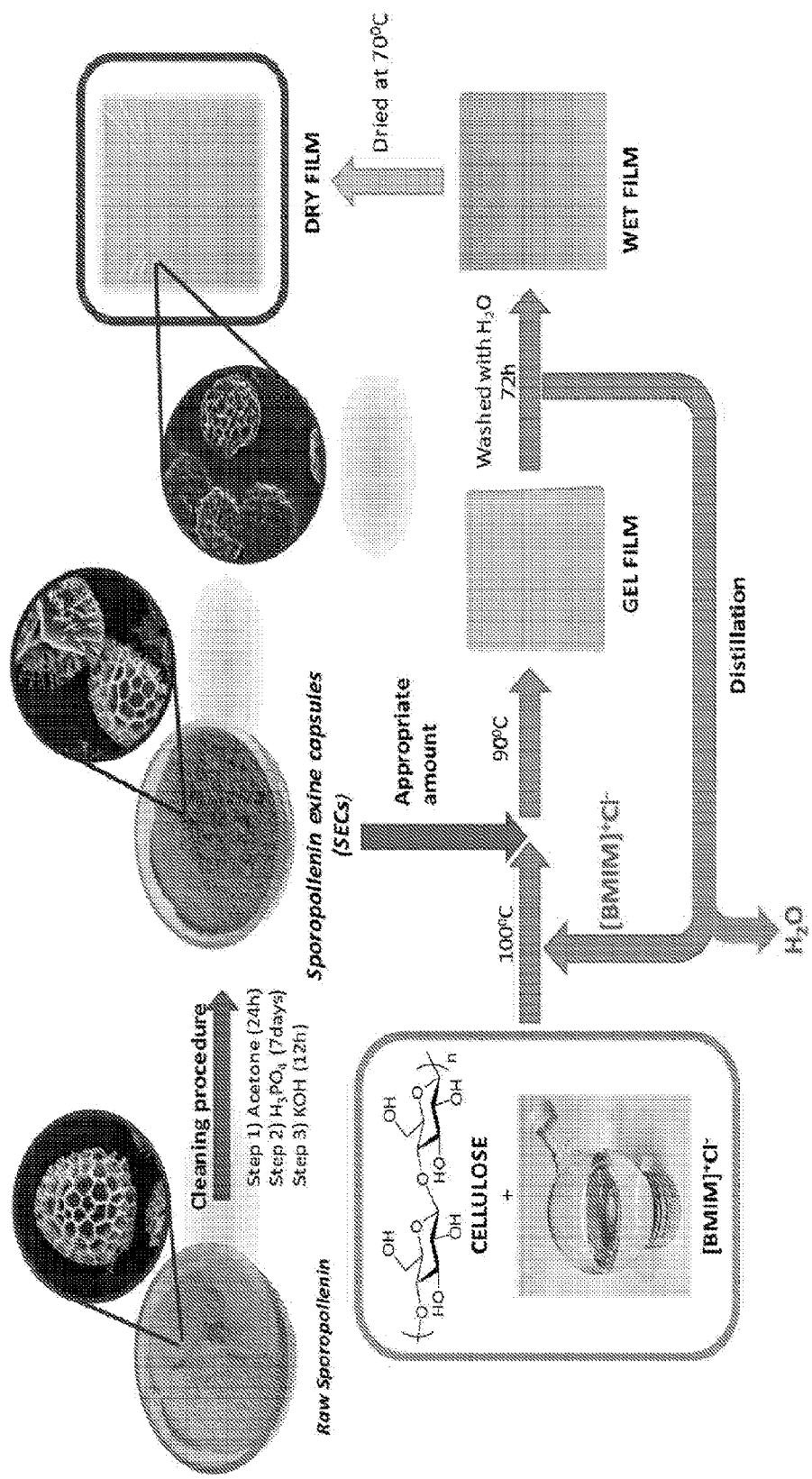
FIG. 1. Schematic diagram of procedure used to purify natural pollen grains and synthesize [CEL+SEC] composites.

The disclosed subject matter further may be described utilizing terms as defined below.

Definitions

Unless otherwise specified or indicated by context, the terms "a", "an", and "the" mean "one or more." For example, "a compound" should be interpreted to mean "one or more compounds."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term that permits additional elements succeeding this transitional term, but only if those additional elements do not materially affect the basic and novel characteristics of the claim.

Disclosed are composite materials and ionic liquid compositions for preparing the composite materials. The composite materials typically include one or more structural polymers (which may include structural polysaccharides and/or structural proteins) and SECs.

As used herein, "structural polysaccharides" refer to water insoluble polysaccharides that may form the biological structure of an organism. Typically, structurally polysaccharides are polymers of 6-carbon sugars such as glucose or modified forms of glucose (e.g., N-acetylglucosamine and glucosamine), which are linked via beta-1,4 linkages. Structural polysaccharides may include, but are not limited to cellulose, chitin, and chitosan, which may be formed from chitin by deacetylating one or more N-acetylglucosamine monomer units of chitin via treatment with an alkali solution (e.g., NaOH). Chitosan-based polysaccharide composite materials and the preparation thereof are disclosed in Tran et al., J. Biomed. Mater. Res. Part A 2013:101A:2248-2257 (hereinafter "Tran et al. 2013), which is incorporated herein by reference.

As used herein, a "structural protein" is a protein that is used to build structural components of a body. Suitable structural proteins for the disclosed composite materials may include but are not limited to keratin. Keratin for use in the disclosed methods for preparing the disclosed composite materials may be derived from a number of sources, including but not limited to wool, human hair, and chicken feathers.

The disclosed composite materials may be prepared from ionic liquid compositions that comprise one or more structural polysaccharides and/or one more structural proteins dissolved in one or more ionic liquids. As used herein, an "ionic liquid" refers to a salt in the liquid state, typically salts whose melting point is less than about 100° C. Ionic liquids may include, but are not limited to salts based on an alkylated imidazolium cation, for example,

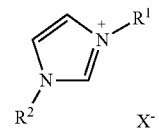

where $R^1$ and $R^2$ are C1-C6 alkyl (straight or branched), and $X^-$ is any cation (e.g., a halide such as chloride, a phosphate, a cyanamide, or the like).

Preparation of Sporopollenin Exine Capsules (SECs)

The disclosed compositions preferably comprise purified SECs obtained from washing natural pollen grains. As used herein, "SECs" refer to empty spherical micron-sized capsules. Further, the SECs are empty spherical microcapsules with diameters of ~25 µm and extensive networks of ~200 nm diameter holes. Suitable natural pollen grains may include, *Lycopodium clavatum*, sunflower (*Helianthus annuus*), short ragweed (*Ambrosia artemisiifolia*), black alder (*Alnus glutinosa*), and cottonwood or necklace poplar (*Populus deltoides*). These pollens are commercially available from various companies including Sigma-Aldrich (Milwaukee, WI), Greer laboratories (Lenoir, NC), Pharmallega (Liswov, Czech Republic).

As disclosed herein, SECs are obtained from washing natural pollen grains. In general, the washing method preferably consists of washing the natural pollen grains with acetone (for about 12 h), followed by acid (for about 7 days), and last with a strong alkaline (for about 12 h). The washing method includes heating the natural pollen grains in the respective solvent in temperatures of about 60-80° C. This cleaning process effectively removes all exterior and interior materials from the natural pollen grains, yielding the SECs. More importantly, the structure and morphology of the pollens remain intact throughout the treatment with this robust procedure. Sizes, structures and morphology of the SECs are dependent on the type of pollens use. Suitable acids for use in the washing method may be phosphoric acid, sulfuric acid, and hydrochloric acid. Suitable strong alkalines for use in the washing method include, but are not limited to, potassium hydroxide and sodium hydroxide.

SECs are green, biocompatible and stable against strong acid and basic conditions as well as corrosive chemicals. They are also thermally stable. These unique properties enable SECs to be uniquely used as novel microencapsulator for applications that are not otherwise possible.

The preferred method for obtaining SECs from natural pollen grains is described in detail below but some variations may be possible.

Prior art methods based on the use of different chemicals sulfuric acid, hydrochloric acid, sodium hydroxide), the order of treatment (e.g., treat with strong alkaline before strong acid), and duration of each step of treatment have been reported. Various ionic liquids have also been used to remove external and internal materials of pollens to yield SECs. We have found that the method of the present invention completely removed all external and internal materials of the pollens to yield SECs with intact size, structure and morphology.

Use of SECs to Encapsulate Materials

The disclosed compositions and composites may comprise SECs that have encapsulated materials. As used herein, the term "encapsulating" refers to material enclosed in the microcavities of the SECs. Suitable examples of "encapsulated materials" may include, but are not limited to, probiotics, prebiotics, synbiotics, fire retardant materials, phase changing materials, dyes, drugs (e.g., ibuprofen, erythromycin, bacitracin), and proteins (e.g., bovine serum albumin). As used herein, the term "microcavity" generally means a microcapsule having an average effective diameter of 25 µm and having extensive networks of ~200 nm diameter holes.

As used herein, "synbiotics" refer to the combination of probiotics and prebiotics in a form of synergism. "Probiotics" refer to microorganisms intended to provide health benefits when consumed. Suitable examples of probiotics may include, but are not limited to, *Lactobacillus plantarum* (*L. plantarum*), *L. acidophilus, L. reuteri, Bifidobacteria animalis* (*B. animalis*), *B. breve, B. lactis,* and *B. longum.* "Prebiotics" refer to non-digestible compounds that induce the growth or activity of beneficial microorganisms or probiotics. Examples of prebiotics may include mannan oligosaccharide and other fructooligosaccharides. As used herein, "fire retardant materials" are materials designed to burn slowly. Suitable examples of fire retardant materials may include, but are not limited to, gypsum, perlite, calcium silicate, sodium silicate, potassium silicate, silicon dioxide, aluminum oxide, magnesium oxide, coated nylon, carbon foam, melamine, modacrylic, polyhydroquinone-diimidazopyridine, polybenzimidazole, aramids, and ionic liquid-based metal-organic hybrid (PMAIL) such as a reaction product between phosphonate-based ionic liquid and phosphomolybdic acid.

As used herein, "phase changing materials" refer to materials that change state with temperature. These materials absorb energy during the heating process to undergo the change from crystalline (or solid) to amorphous (or liquid state), and release energy in the reverse cooling phase. The energy absorbed or released depending on the phase change will, in effect, regulate the environment, i.e., cool down the hot environment and heat the cool environment. Suitable examples of applications of phase changing materials may include, but are not limited to, sodium acetate heating pad and hand warmer (e.g., sodium acetate solution crystallizes, heat produced by crystallization produce "warming effect") and smart building insulation such as Infinite R™ by Syndergo LLC (when installed within a structure, Infinite R™ actively stabilizes interior temperature, absorbing heat when temperature exceeds a desired target and releasing heat when temperature drops below that target). Other suitable phase change materials to be encapsulated by the capsules disclosed herein include acyclic alkanes. Suitable acyclic alkanes include, but are not limited to, n-octadecane (C18), n-eicosane (C20, EIS), n-docosane (C22) and mixtures thereof.

The SEC encapsulating method consists of mixing purified SECs and a material to be encapsulated, approximately at a 1:1 ratio. The resulting mixture is heated under vacuum at about 70° C., followed by washing and filtration, followed by drying. The method for encapsulating materials into SECs is described in detail below.

Composite Preparation

The composite preparation method comprises dissolving a structural polysaccharide and/or structural protein in an ionic liquid. Once dissolved, the appropriate quantity (about 0%, 1%, 2%, 3%, 5%, 10%, 15%, 33.3% (wt/wt) of the mass of CEL) of empty or encapsulated SECs is added. The resulting mixture is poured into molds and allowed to undergo gelation. The gel is washed to remove the ionic liquid and the resulting films are dried. The methods for preparing composites with empty or encapsulated SECs are described in detail below.

Methods for preparing the disclosed composites are modified (to include SECs) from previously disclosed methods by the Inventor in the following applications: Tran, WO 2017/156256A1; Tran, WO 2014/186702A1; Tran, WO 2018/075614; the contents of which are incorporated herein by reference in their entireties.

The disclosed composite materials may be utilized to produce temperature-regulating materials wherein, the composite material may contain phase change materials encapsulated into SECs. For example, the composite material may be utilized in the production of temperature-regulating materials, such as textiles or building materials. As such, the composite material may be utilized in building materials or textiles requiring building- or body-temperature control. As used herein "building materials" refer to materials used for construction purposes. Suitable examples of building materials may include, but are not limited to, cement, wood, concrete, foam, glass, steel, aluminum, copper, and ceramic. As used herein "textiles" or "fabric" are used interchangeably and refer to materials used to make clothes. Suitable examples of textiles may include, but are not limited to, natural biopolymers (e.g., cotton, hemp, linen, wool, silk) alone or blended and synthetic polymers such as polytetrafluoroethylene (PTFE), polyester, nylon, and polypropylene.

In other embodiments, the disclosed composite materials may be utilized to produce temperature-regulating materials wherein, the composite material may contain fire retardant materials encapsulated into SECs. For example, the composite material may be utilized in the production of temperature-regulating materials, such as textiles or insulated building materials. As such, the composite material may be utilized in building materials or textiles requiring building- or body-temperature control.

In other embodiments, the disclosed composite materials may be utilized to produce temperature-regulating materials wherein, the composite material may contain both fire retardant materials and phase changing materials encapsulated into SECs.

In other embodiments, the disclosed composite materials may be utilized to produce biocompatible microencapsulators for probiotics and/or prebiotics. The disclosed composite materials may protect probiotics and/or prebiotics from stomach acids and enzymes, so they retain their activity when they reach the intestines.

Various methods have been previously developed to improve the stability of bacterial probiotics, including water-based suspensions, lyophilization, spray-drying, and microencapsulation (ME). ME has been found to improve the stability and activity of probiotics under harsh gastric conditions by placing the probiotics within protective microcapsules that preserve their activity. MEs can also control the release of probiotics into targeted environments. To date, most microcontainers are derived from man-made polymers. As such, they are not biocompatible, are costly, and difficult to synthesize. The disclosed composite materials are well suited for use as microencapsulators for probiotics because they are cheap, biocompatible, biodegradable. Bacteria such as *Lactobacillus plantarum* (LP), can be encapsulated into its cavity. In some embodiments, the disclosed composite materials may encapsulate a probiotic and its corresponding prebiotic mannan oligosaccharide (MOS). The mixture of probiotics and prebiotics is known to be synbiotic.

The disclosed compositions and composites may include additional active agents. Suitable active agents may include anti-microbial agents (e.g., anti-bacterial agents, and anti-fungal agents). Suitable anti-microbial agents may include, but are not limited to ciprofloxacin, amoxicillin, doxycycline, azithromycin, erythromycin, roxithromycin, flucloxacillin metronidazole, co-trimoxazole, cephalexin, and the like. As disclosed herein the release of anti-microbial agents incorporated into the disclosed composite materials may be controlled, for example, based on the concentration of structural protein in the composite material such as keratin.

In other embodiments, the disclosed composite materials may be utilized to produce high-performance dressings (bandages) to heal or treat infected wounds and burn wounds wherein, the composite material may contain the additional active agents.

Illustrative Embodiments

The following embodiments are illustrative and are not intended to limit the scope of the claimed subject matter.

Embodiment 1. An ionic liquid composition comprising: (a) a structural polysaccharide and/or a structural protein dissolved in an ionic liquid; and (b) sporopollenin exine capsules (SEC).

Embodiment 2. The composition of embodiment 1, wherein the structural polysaccharide is a polymer comprising 6-carbon monosaccharides linked via beta-1,4 linkages.

Embodiment 3. The composition of any of the foregoing embodiments, wherein the structural polysaccharide comprises cellulose.

Embodiment 4. The composition of any of the foregoing embodiments, wherein the structural polysaccharide comprises chitin.

Embodiment 5. The composition of any of the foregoing embodiments, wherein the structural polysaccharide comprises chitosan.

Embodiment 6. The composition of any of the foregoing embodiments, wherein the structural protein comprises keratin.

Embodiment 7. The composition of any of the foregoing embodiments, wherein the structural protein is a mixture of at least two materials selected from cellulose, chitin, chitosan, and keratin.

Embodiment 8. The composition of any of the foregoing embodiments, wherein the SECs contains an encapsulated material.

Embodiment 9. The composition of embodiment 8, wherein the encapsulated material comprises at least one of probiotics, prebiotics, fire retardant materials, and phase change materials.

Embodiment 10. The composition of any of the foregoing embodiments, wherein the ionic liquid is an alkylated imidazolium salt.

Embodiment 11. The composition of embodiment 10, wherein the alkylated imidazolium salt is selected from a group consisting of 1-butyl-3-methylimidazolium salt, 1-ethyl-3-methylimidazolium salt, and 1-allyl-3-methylimidazolium salt.

Embodiment 12. The composition of any of the foregoing embodiments, wherein the ionic liquid is 1-butyl-3-methylimidazolium chloride.

Embodiment 13. The composition of any of the foregoing embodiments, wherein the ionic liquid composition comprises at least 4% w/w of the dissolved structural polysaccharide and/or structural protein.

Embodiment 14. The composition of any of the foregoing embodiments, wherein the ionic liquid composition comprises at least 10% w/w of the dissolved structural polysaccharide and/or structural protein.

Embodiment 15. A method for preparing a composite material comprising a structural polysaccharide and/or a structural polypeptide and SECs, the method comprising: (a) dissolving a structural polysaccharide and/or the structural polypeptide and SECs in an ionic liquid, and (b) removing the ionic liquid to obtain a composite material.

Embodiment 16. The method of embodiment 15, wherein the SECs contain an encapsulated material.

Embodiment 17. The method of any of embodiments 15 or 16, wherein the ionic liquid is removed by steps that include washing the ionic liquid composition with an aqueous solution to obtain the composite material and drying the composite material thus obtained.

Embodiment 18. A composite material prepared by the method of any of embodiments 15-17.

Embodiment 19. A method for delivering a material, the method comprising providing the composite material of embodiment 18 and allowing the encapsulated material to diffuse from the composite material.

Embodiment 20. A method for producing a textile, the method comprising adding the composite material of embodiment 18, wherein the SEC encapsulates a phase change material, to a fabric used in the production of a textile.

Embodiment 21. A method for producing a building material, the method comprising adding the composite material of embodiment 18, wherein the SEC encapsulates a phase change material, to a mixture used in the production of a building material.

Embodiment 22. A method for producing a building material, the method comprising adding the composite material of embodiment 18, wherein the SEC encapsulates a fire retardant material, to a mixture used in the production of a building material.

Embodiment 23. A method for producing a textile, the method comprising adding the composite material of embodiment 18, wherein the SEC encapsulates a fire retardant material, to a fabric used in the production of a textile.

Embodiment 24. A method for producing SECs from natural pollen grains, the method comprising: (a) washing natural pollen grains with acetone for about 24 hours, (b) followed by washing with phosphoric acid for about 7 days, and (c) then washed with a strong alkaline for about 12 hours.

Embodiment 25. The method of embodiment 24, wherein the natural pollen grain is *Lycpodium clavatum*.

Embodiment 26. The method of any of embodiments 24 or 25, wherein the strong alkaline is potassium hydroxide.

Embodiment 27. A method for encapsulating a material into SEC microcavities, the method comprising: (a) mixing the encapsulated material with SECs produced by the method of claim 24, (b) heating the mixture under vacuum, (c) washing the mixture with ethanol, (d) filtering the mixture, and (e) drying the mixture.

Embodiment 28. The method of embodiment 27, wherein the encapsulated material comprises a material selected from the group consisting of phase change materials, fire retardant materials, probiotics, and prebiotics.

EXAMPLES

The following examples are illustrative and are not intended to limit the claimed subject matter.

Example 1

Natural Sporopollenin Microcapsules Facilitated Encapsulation of Phase Change Material into Cellulose Composites for Smart and Biocompatible Materials Sporopollenin exine capsules (SECs) are empty microcapsules that are 25 μm in diameter and have extensive networks of ~200 nm diameter holes obtained by chemically removing all external and internal cytoplastic materials from the natural pollen grains. We have demonstrated that a phase change material (PCM) such as n-eicosane (EIS), a natural paraffin wax, can be successfully encapsulated in the SECs to produce [EIS@SEC]. The high stability and robust nature of SECs retain EIS in the microcavity even during phase transitions, enabling EIS to fully maintain its phase change property, while also protecting the EIS from elevated temperatures and corrosive environments. [EIS@SEC] can, therefore, be incorporated into cellulose (CEL) composites with a synthetic process that uses the simple ionic liquid butylmethylimmidazolium chloride to produce [CEL+EIS@SEC] composites. Similar to EIS alone, EIS in the [CEL+EIS@SEC] composites melts when heated and crystallizes when cooled. The energies associated with the crystallization and melting processes enable the [CEL+EIS@SEC] composites to fully exhibit the properties expected of PCMs, i.e., heating the surroundings when they cool and absorbing energy from the surroundings when they warm. The efficiency of latent heat storage and release of [CEL+EIS@SEC] composites was estimated to be around 57% relative to pure EIS. The fact that the DSC curves of the [CEL+EIS@SEC] composites remain the same after going through the heating-melting cycle 220 times clearly indicates that SEC effectively retains EIS in its cavity, protects it from leaking, and that the [CEL+EIS@SEC] composites are highly stable and reliable as a phase change material. The [CEL+EIS@SEC] composites are superior to any other available materials based on encapsulated PCM because they are not only robust, reliable, and stable and have strong mechanical properties. They are also are sustainable and biocompatible because as they are synthesized from all naturally abundant materials using a green and recyclable synthesis. These features enable the [CEL+EIS@SEC] composites to be uniquely suited as high performance materials for such uses as dressings to treat burnt wounds, smart textiles for clothing, and smart building materials, and energy storage.

Introduction

Smart materials can sense and react to environmental conditions in a predetermined way.[1-4] For example, smart building materials and smart textiles can sense and respond to ambient temperatures, keeping the building and the body's temperature steady regardless of the environmental temperature.[1-4] The material absorbs energy when it is hot in order to lower the ambient temperature, and releases absorbed energy when it is cold to warm it up. Such materials not only improve human well-being but also improve energy efficiency.[1-4] Considerable efforts have been made to produce these materials, but only with limited success. To date, most available materials are based on synthetic polymers because polymeric materials can easily and readily be designed and synthesized with specific properties.[1-4] As a consequence, they may not be biocompatible, and hence, cannot be used for applications related to medicine and foods. It is therefore desirable to develop smart materials entirely from natural and sustainable biopolymers.

Recently, we developed a novel, green and recyclable method based on the use of a simple ionic liquid, 1-methylbutyl imidazolium chloride (BMIm$^+$Cl), as the sole solvent to synthesize biocompatible composites from all natural and sustainable biopolymers such as cellulose (CEL), chitosan (CS) and keratin (KER) from either wool, hair or chicken feathers.[5-11] The composites obtained fully retain the properties of their components, i.e., superior mechanical strength (from CEL), excellent adsorbent for pollutants (organic pollutants, heavy metal ions and toxins), hemostatic, anti-inflammatory, antimicrobial activity, and wound healing (from CS and KER).[5-11] The composites have been successfully used to purify drinking water and for use as high-performance dressings to heal ulcerous and infected wounds common to diabetic patients.[5-8, 11] It would be desirable if these biocompatible composites could also be able to control and regulate temperature. It may be possible to add this property to the CEL composites by synergistically exploring the use of phase change materials and sporopollenin exine capsules.

Phase change materials (PCM) are materials that change their state with temperature.[12-15] They absorb energy during the heating process to change from crystalline (or solid) to amorphous or (liquid state), and release energy in the reverse cooling process. The energy absorbed or released concomitance with their phase change, will, in effect, regulate the environment, i.e., absorb heat from warmer surroundings and release heat to cooler surroundings.[12-15] PCMs have been used to provide materials with the ability to regulate building and body temperature.[12-15] Considerable efforts have been made to further explore these possibilities, but to date only limited success has been achieved. A variety of reasons might account for this lack of success, but the most critical drawback is due to the difficulty associated with retaining PCMs in the materials when the PCMs undergo phase change from solid to liquid.[12-15] Synthetic microcapsules have been used to encapsulate PCMs, so that the PCMs can be retained in the materials, but again it is not desirable to use synthetic polymeric microcapsules as they are not biocompatible or biodegradable.[12-15]

Sporopollenin exine capsules (SECs) are hollow spherical microcapsules (diameter ~25 μm) with a porous wall made up of an extensive network of ~200 nm diameter holes.[16-26] They are derived from natural pollen grains using cleaning processes that remove cytoplasmic materials. Being derived from natural pollen grains, SECs are biocompatible.[16-26] More importantly, they are highly resistant to high temperature, chemicals, acids, and alkalis.[16-26] Because of their unique properties, considerable efforts have been made to explore the use of SECs as alternatives to synthetic microencapsulators. Notable successes have been made, particularly in the field of drug delivery and the food industry.[24,25] It may be possible to use SEC as all natural microencapsulator to encapsulate PCMs, and then incorporating the resulting PCM@SECs into the CEL composites to render the composites the ability to regulate and control temperature.

The information presented is compelling and indicates that it is possible to use all natural biopolymers such as cellulose, natural pollen grains, and phase change material to synthesize a novel and high-performance biocompatible composite that can control and regulate temperature for applications such as smart building materials and smart textiles. Such considerations prompted us to start this study which aims to hasten a breakthrough by systematically developing a novel method to synthesize biocompatible composites from sustainable and all natural biopolymers including CEL, natural pollen grains, and eicosane, a natural PCM. Specifically, we will (1) develop a method to process *Lycopodium clavatum* powder, derived from natural pollen grains from clubmoss, to produce SECs; (2) encapsulate eicosanes (EIS) into SECs; and (3) incorporate EIS@SEC into CEL composites. The synthesis, characterization and properties of the [EIS@SEC+CEL] composites are reported herein.

Experimental Section

Chemicals. Cellulose (microcrystalline powder), chitosan (molecular weight≈310-375 kDa), Nile Blue hydrochloride (90%) were purchased from Sigma-Aldrich (Milwaukee, WI) and used as received. *Lycopodium clavatum* powder, orthophosphoric acid (85%), potassium hydroxide, acetone and ethanol were from Fischer Scientific Company (USA). Sodium hydroxide (98%), HCl (37%) and Malachite Green oxalate were purchased from ACROS Organics. 1-Methyl-imidazole and n-chlorobutane (both from Alfa Aesar, Ward Hill, MA) were distilled and subsequently used to synthesize [BMIM]$^+$Cl$^-$ using previously reported method.[5-11] n-eicosane (99%) (Alfa Aesar, Ward Hill, MA) was recrystallized from methanol. Its purity was verified by GC-MS.

Instruments. X-ray powder diffraction (XRD) measurements were taken with a Rigaku MiniFlex II diffractometer equipped with Ni-filtered Cu Kα radiation (1.54059 Å). The X-ray tube was operated at 30 kV and 15 mA. The samples were measured within the 2θ range of 5.0-50.0°. The scan rate was 2°/min. The Jade 8 program was used to process the data package. FTIR spectra were recorded from 650 to 4000 cm$^{-1}$ and with 4 cm$^{-1}$ resolution on an FTIR spectrometer (Spectrum 100 Series, PerkinElmer) using the ATR method. The scanning electron microscopy (SEM) images of the pollen grains and the composites were recorded under vacuum with a JEOL JSM-6510LV/LGS scanning electron microscope with standard secondary electron and backscatter electron detectors. The composites were initially made conductive by applying a 20 nm gold-palladium coating onto their surfaces using an Emitech K575x Peltier Cooled Sputter Coater (Emitech Products, TX). The tensile strength of the composite films was evaluated on an Instron 5500R tensile tester (Instron Corp., Canton, MA) equipped with a 5.0 kN load cell and operated at a crosshead speed of 0.5 mm min$^{-1}$. Fluorescence confocal images were taken on a Nikon Eclipse Ti-E inverted microscope from Nikon, Japan using a 60× water objective. The microscope was equipped with Cascade blue (375-420 nm), FITC (494-518 nm) and Texas Red (595-613 nm) laser lines. The scan speed was set at 32 fps. Images obtained were analyzed and processed using NIS Elements—Microscope Imaging software by Nikon NIS Elements—Microscope Imaging software by Nikon.

Thermogravimetric analysis (TGA) of the composites was taken on a Thermal Analysis (TA) TGA instrument (model Q5000) using a platinum pan and at a heating rate of 20.0° C./min (to 800.00° C.) under a continuous flow of 10.0 mL/min of nitrogen gas.

DSC was used to measure the thermal transitions of EIC and [CEL+EIC@SEC] composites. The measurements were performed with a TA Q2000 DSC instrument with aluminum sample pan in nitrogen atmosphere and a static nitrogen flow of 50.0 mL/min. The sample was initially equilibrated isothermally at 0.00° C. for 2.0 min, heated to 120.00° C., and then isothermally equilibrated for 1.0 min before cooling down to 0.0° C./min. Both heating and cooling rate were 2.0° C./min. For each of the [CEL+EIS@SEC] composites, heat of crystallization and melting enthalpy values (ΔH$_c$ and ΔH$_m$) for five different samples were measured, and average ΔH$_c$ and ΔHm values are reported together with their associated standard deviations.

Dynamic mechanical analysis was carried out using a TA DMA Q800 instrument in 3-point bending mode. The testing temperature was varied from −120.0° C. to 300.0° C. at a constant frequency of 1 Hz and heating rate of 10.0° C./min. The values of storage modulus (E'), loss modulus (E"), and damping factor (tan δ) were recorded.

Procedure used to clean natural pollen grains to produce empty Sporopollenin Exine Capsules (SECs). The cleaning procedure, shown in the Scheme 1 was performed using reported procedure.[12-16] Briefly, *Lycopodium clavatum* pollen grains were stirred overnight in acetone under reflux, filtered and air dried for 12 h. The pollens were then transferred to a 6% w/v orthophosphoric acid solution under vigorous stirring at 60° C. for 7 days, filtered and sequentially washed twice with hot water, acetone, 2M HCl, 2M NaOH, six times with water, acetone and ethanol. The pollens were dried overnight and transferred to 6% w/v KOH aqueous solution, stirred at 80° C. for 12 h. After vacuum filtration the pollens were washed 6 times with hot water, acetone, hot ethanol and finally dried at 60° C. until constant weight to yield fine brown powder SECs with 31% yield.

Encapsulation of dyes into SECs. Evan blue was encapsulated into the cavity of the SECs to render visualizing the inner cavity of the SECs. The dye was used as ethanolic solution (0.5 g/mL) and loaded into the pollens in quantity of 1 g/g (2 ml of ethanolic solution/g of SECs) under vacuum for 2.0 h as reported in literature.[24,25] The SECs were then washed twice with ice cold water to remove any surface adsorption. The pollens were dried at 70° C. until constant weight and then analyzed with the fluorescence confocal microscope.

Encapsulation of n-eicosane into SECs. n-eicosane (EIS) and SECs were finely mixed at appropriate ratio, e.g., 2 g of EIS per 1 g of SEC, at room temperature and placed into a round bottom flask. The solid mixture was gently stirred at 70° C., under vacuum for 3.0 h. Subsequently, the n-eicosane loaded SECs (i.e., EIS@SECs) was washed twice with ethanol (2 mL/10 mg for 5 min) to remove any possible traces of EIS adsorbed to SEC surface. The suspension was filtered, and the (EIS@SECs) obtained was air-dried overnight. XRD diffractograms of the (EIS@SECs) are used to confirm that the EIS was encapsulated into the cavity of the SECs. SEM images of the (EIS@SECs) are used to verify that there was no solid EIS adsorbed on the surface of the SECs.

Synthesis of [CEL+SEC] composites. As shown in Scheme 1, microcrystalline cellulose (3% wt/wt) was completely dissolved in [(BMIM)$^+$Cl$^-$] at 100° C. Once dissolved the temperature was reduced to 90° C. and the appropriate quantity of SECs (0%, 1%, 2%, 3%, 5%, 10%, 15%, 33.3% (wt/wt) of the mass of CEL) was added. The mixture was stirred for 1.0 h and then casted onto PTFE molds, the amount (g) of mixture poured into each mold was kept constant to maintain constant thickness of the composite films. The mixture was allowed to undergo gelation at room temperature for 24.0 h, and then washed with water for 72.0 h to remove [BMIM$^+$Cl$^-$] from the films. The wet films were then dried in the oven at 70° C. for 5 days to yield the [CEL+SEC] dried films.

Procedure used to prepare [CEL+EIS@SEC] composites. [CEL+EIS@SEC] composites were synthesized using procedure similar to that used to synthesize the [CEL+SEC] composites. Essentially, CEL was completely dissolved in [BMIM+Cl−] at 100° C. (3% w/w); the temperature was then reduced to 90° C. and appropriate amount (10%, 20%, 33%) of the EIS@SEC were added. The mixture was stirred for 1.0 h and then casted into PTFE molds. The mixture was allowed to undergo gelation at room temperature for 24.0 h, and subsequently, washed with water for 72.0 h to remove the IL. The [CEL+EIS@SEC] wet film obtained was then dried at 30° C. under vacuum for 5 days to yield the [CEL+EIS@SEC] dry films.

Results and Discussion

Figure 2:
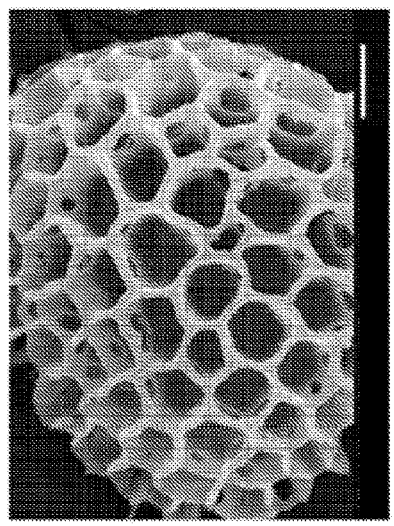
FIG. 2. Scanning electron microscope (SEM) images of intact natural pollen grains (A and B); sporopollenin (SEC) (C and D) and eicosane (EIS) encapsulated in SEC (E and F). Scale bar: A-10 μM; B-5 μM; C-5 μM; D-10 μM; E-5 μM; and F-5 μM.
Figure 2:
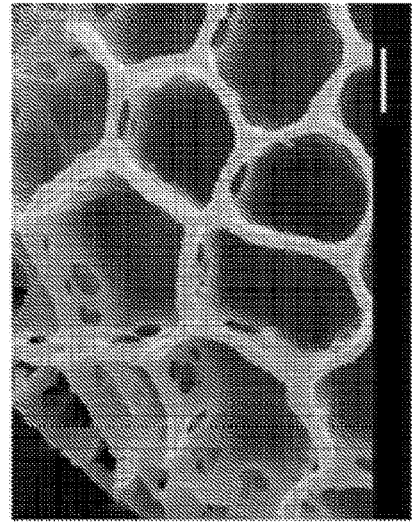
Figure 2:
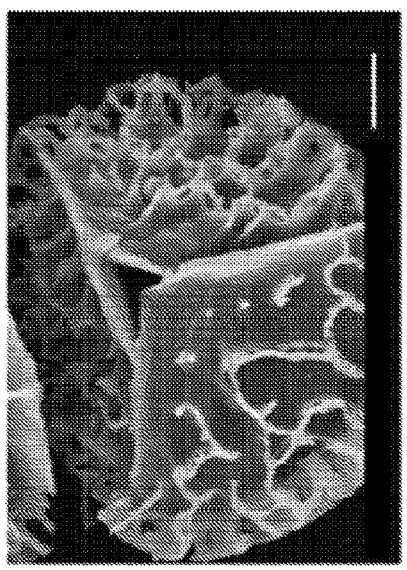
Figure 2:
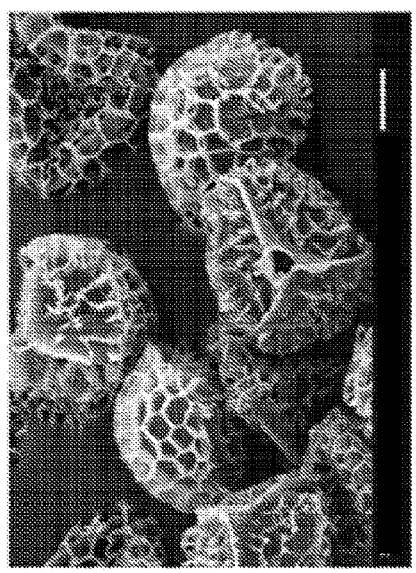
Figure 2:
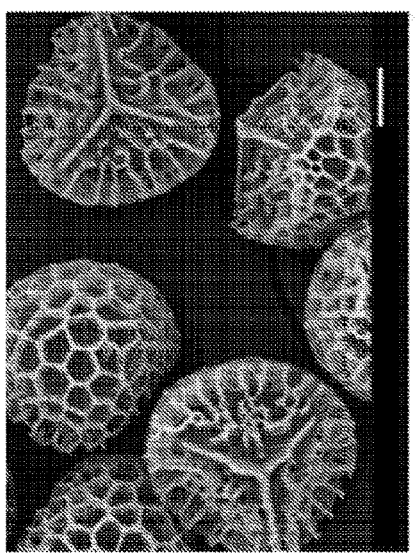
Figure 2:
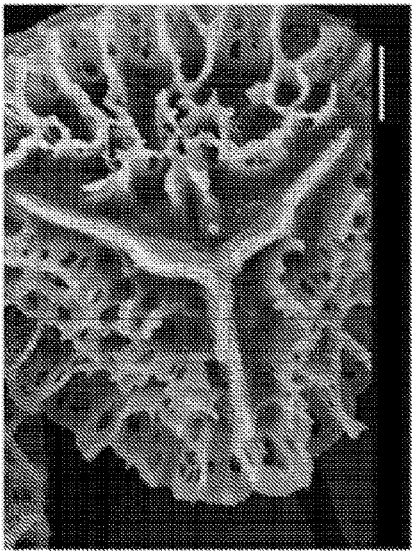
Figure 3:
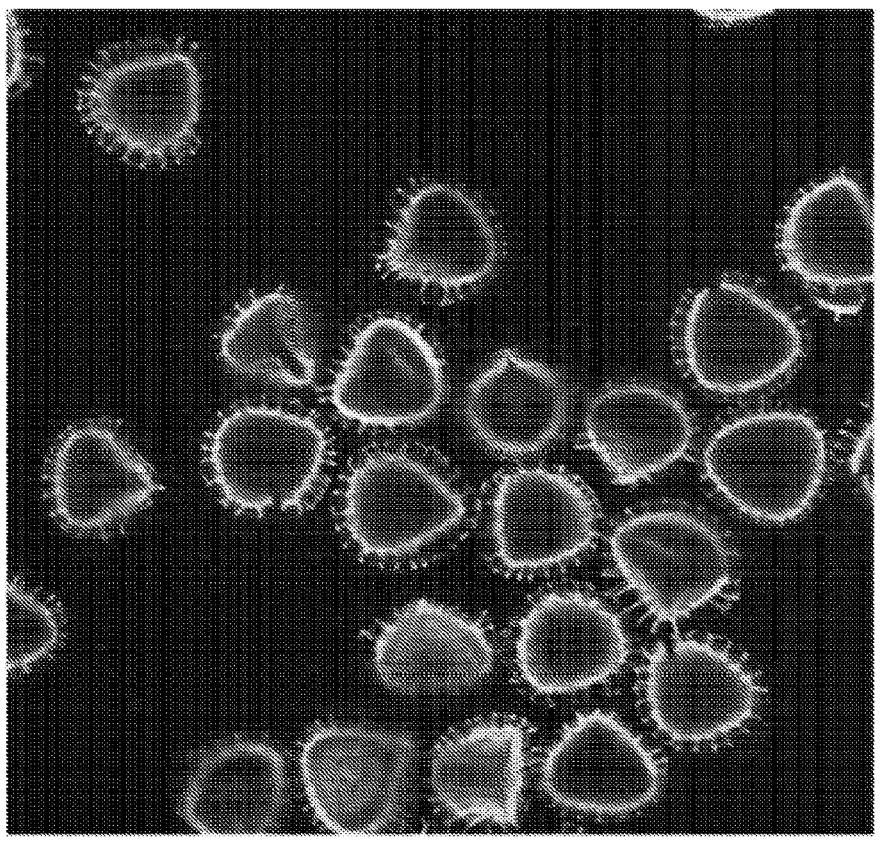
FIG. 3. Confocal fluorescence microscope images of intact pollens (A) and SEC stained with evan blue (B).
Figure 3:
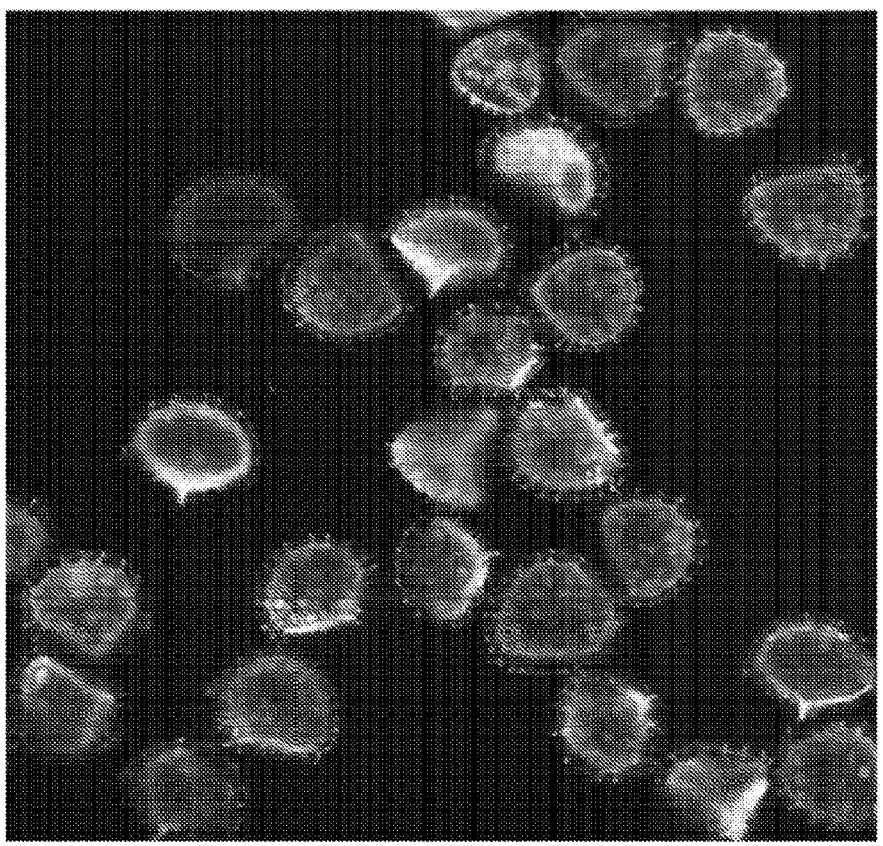

Cleaning Procedure to Produce Sporopollenin Exine Capsules (SECs) from Natural Pollen Grains. SECs obtained using cleaning procedure described in the Experimental Section were characterized by scanning electron microscope (SEM) and confocal fluorescence microscope. The results obtained, shown in in FIGS. 2A and B, are SEM images of raw, untreated pollen, and those of SEC are shown in FIGS. 2C and D. As illustrated, the fact that the SEM images of SEC are very similar to those of the raw pollen clearly indicates that even with this robust treatment, SECs (FIGS. 2C and 2D) fully retained their native structure and morphology with consistent size. FIG. 2 shows Scanning electron microscope (SEM) images of intact natural pollen grains (FIGS. 2A and 2B); (ca 25 µm in diameter extensive networks of ~200 nm diameter holes). A confocal fluorescence microscopic image of SEC that was stained with Evan Blue is shown in FIG. 3B together with the image of unstained raw pollen (3A). It is clear from these images that all interior cytoplastic materials of the pollen were effectively removed by the treatment to yield SECs that are empty spherical microcapsules with intact structure and morphology.

Figure 4:
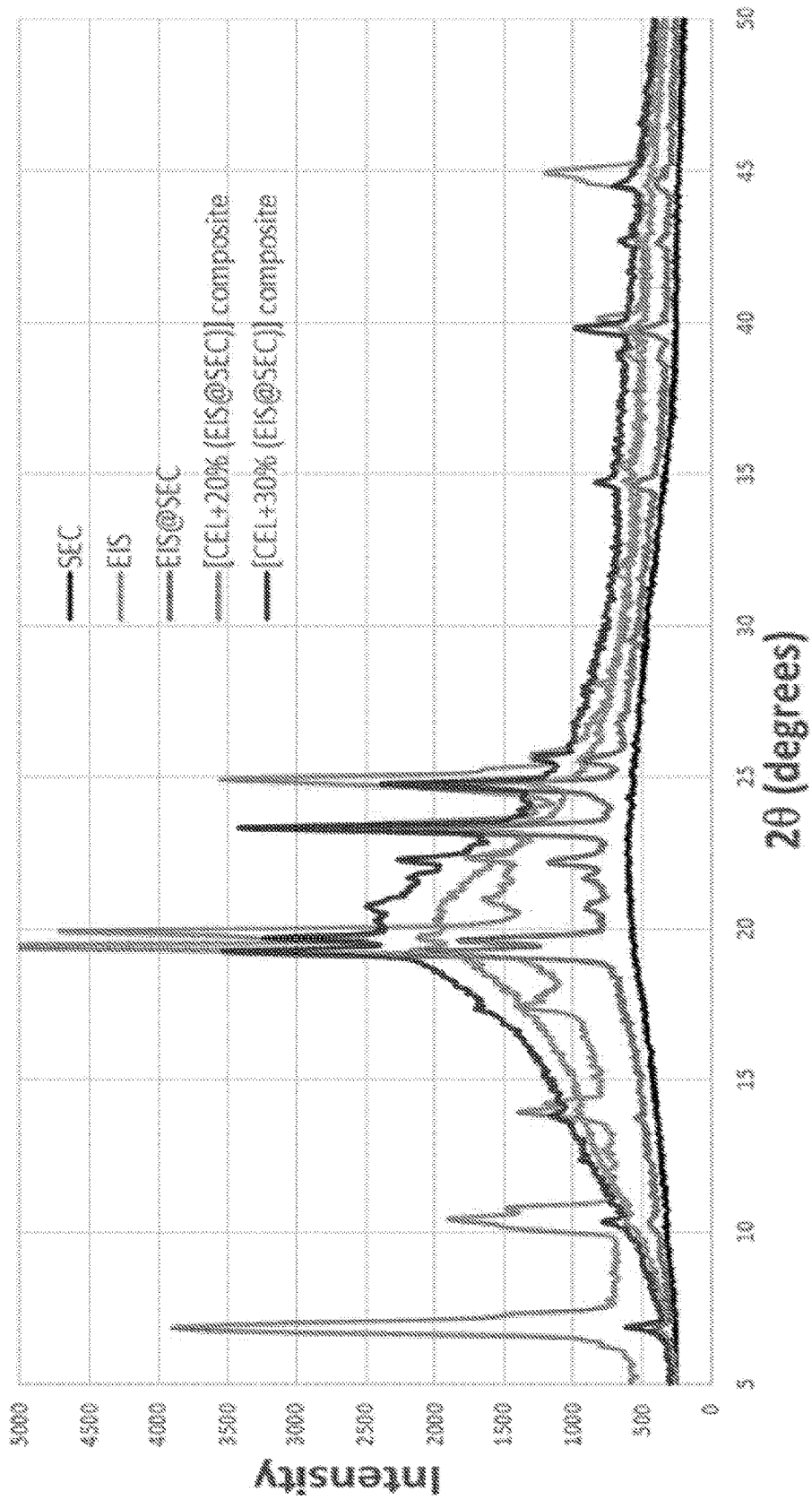
FIG. 4. Powder X-ray diffractograms of SEC (black), eicosane, EIS@SEC, [CEL+20% EIS@SEC] composite and [CEL+30% EIS@SEC] composite.

Encapsulating Phase Change Material into Cavity of SECs. There are many different compounds that possess the PCM property. n-eicosane (EIS) was selected for this study because it is readily available in nature, and has a melting point around 38° C., making it is particularly well-suited for use in smart textile to maintain body temperature or in building materials to regulate building temperature at 38° C. As described in the Experimental Section, EIS was encapsulated into the cavity of SEC by heating under vacuum. X-ray diffraction (XRD) was used to verify the effectiveness of the encapsulation. As illustrated in FIG. 4, SECs with their amorphous structure have only a broad XRD band whereas EIS exhibits many discrete bands as expected for its crystalline structure. The fact that the EIS@SEC spectrum contains the same discrete XRD bands as those for EIS alone clearly indicates that EIS was successfully encapsulated into the cavity of SEC.

Even though the EIS@SEC was washed thoroughly after encapsulating EIS into SEC, there is a possibility that some EIS remains adsorbed onto the surface of SEC.[26] This possibility was investigated by comparing SEM images of [EIS@SEC] to those of SEC. As depicted in FIG. 2, the fact that the SEM images of EIS@SEC (2E and F) are very clear but also are very similar to those of SEC (2C and D) clearly indicates that no EIS adsorbed onto the surface of SEC; all EIS was effectively encapsulated into the cavity of SEC.

As will be described in detail in the subsequent section on differential scanning calorimetry (DSC), by comparing DSC curves of EIS alone and with EIS@SEC, it is estimated that this method (i.e., 2 g of EIS per 1 g of SEC) successfully encapsulated at least 63% of EIS (relative to the amount of EIS used for encapsulation) into the SEC cavity. Preliminary results show that it may be possible to encapsulate larger amounts of EIS into SEC using a higher ratio of EIS/SEC (e.g., 3 g of EIS/1 g of SEC), and repeating the heating and cooling cycle of the EIS+SEC mixture under vacuum several times.

Figure 5:
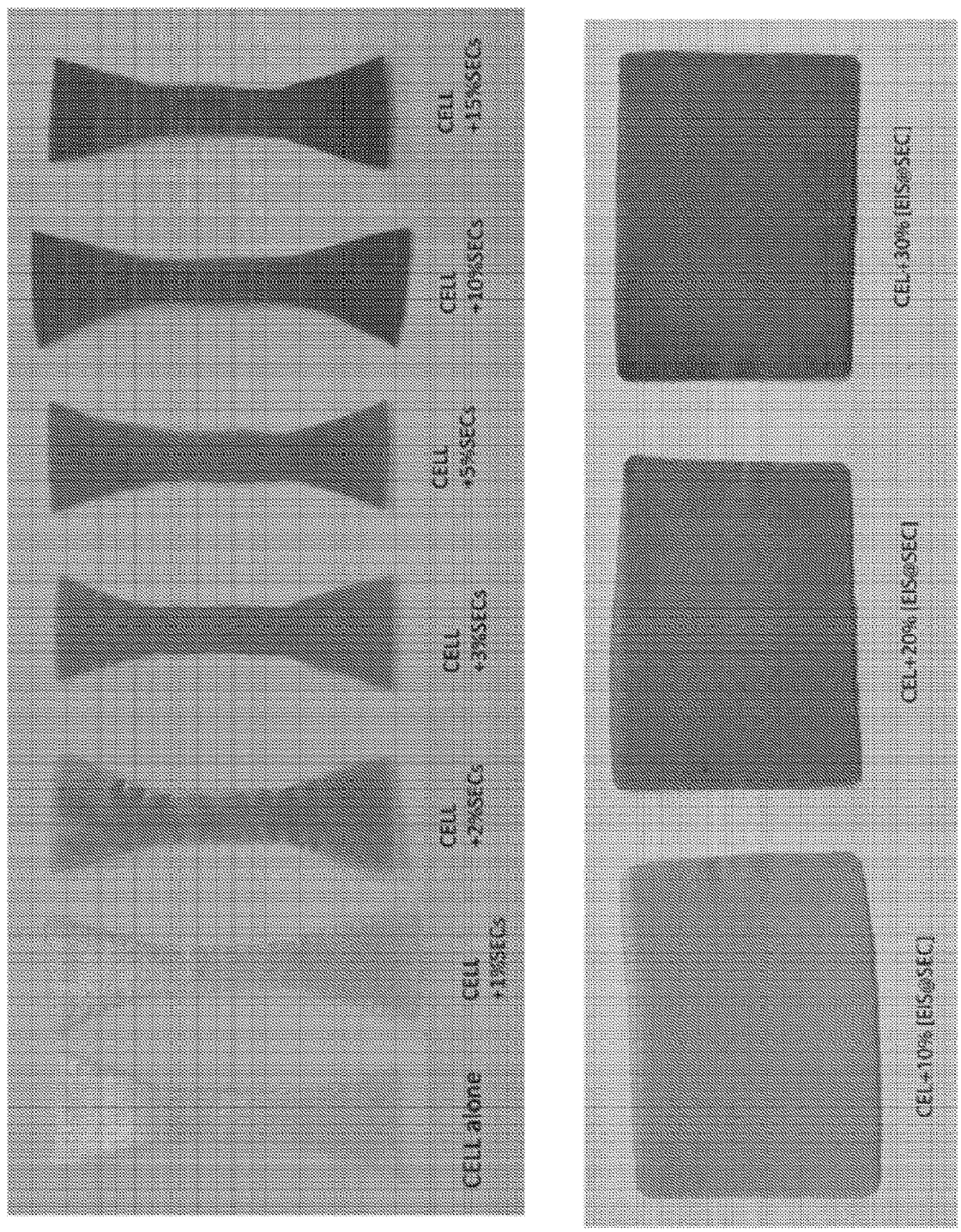
FIG. 5. Photographs of (A) CEL composites without SEC and with different concentrations of encapsulated SEC, and (B) CEL composites with different concentrations of encapsulated [EIS@SEC].

Synthesis and Characterization of [CEL+SEC] and [CEL+EIS@SEC] Composites. As described in the Experimental Section and illustrated in FIG. 1, the same procedure was used to prepare [CEL+SEC] composites and [CEL+EIS@SEC] composites. FIG. 5 shows photographs of [CEL+SEC] composites and [CEL+EIS@SEC] composites with different concentrations of SEC and [EIS@SEC], respectively together with CEL composite without any SEC or [EIS@SEC]. Similar to CEL composites used in our previous studies[5-8], the CEL composite has no color and is transparent. As shown in FIG. 1, because SEC is brown and EIS is white, so composites with higher concentration of SEC (or EIS@SEC) appears darker. At comparable SEC and EIS@SEC content, the [CEL+SEC] composite is visually similar to the [CEL+EIS@SEC] composite, and composite with higher concentration of SEC (or EIS@SEC) appears darker. As described above, the melting point of EIS is 38° C., and in the synthesis of [CEL+EIS@SEC], the [EIS@SEC] was added to the BMIm+Cl− at 90° C., there is a possibility that EIS melted at this temperature and escaped from the cavity of SEC. Accordingly, this possibility was investigated by measuring XRD diffractograms of [CEL+EIS@SEC] composites with different concentrations of [EIS@SEC]. Shown in FIG. 4 are XRD diffractograms of [CEL+20% EIS@SEC] composite and [CEL+30% EIS@SEC] together with those for SEC (black curve), EIS and [EIS@SEC]. The fact that both [CEL+20% EIS@SEC] and [CEL+30% EIS@SEC] composites exhibit the same discrete bands characteristic of EIS and also that the intensity of these bands correlates with the concentration of [EIS@SEC] in the composite clearly indicates that EIS remained in the cavity of SEC during the synthetic process where the [EIS@SEC] was subjected to a temperature as high as 90° C. Additional information on structure and morphology of the composites from the SEM images is described below.

Figure 6:
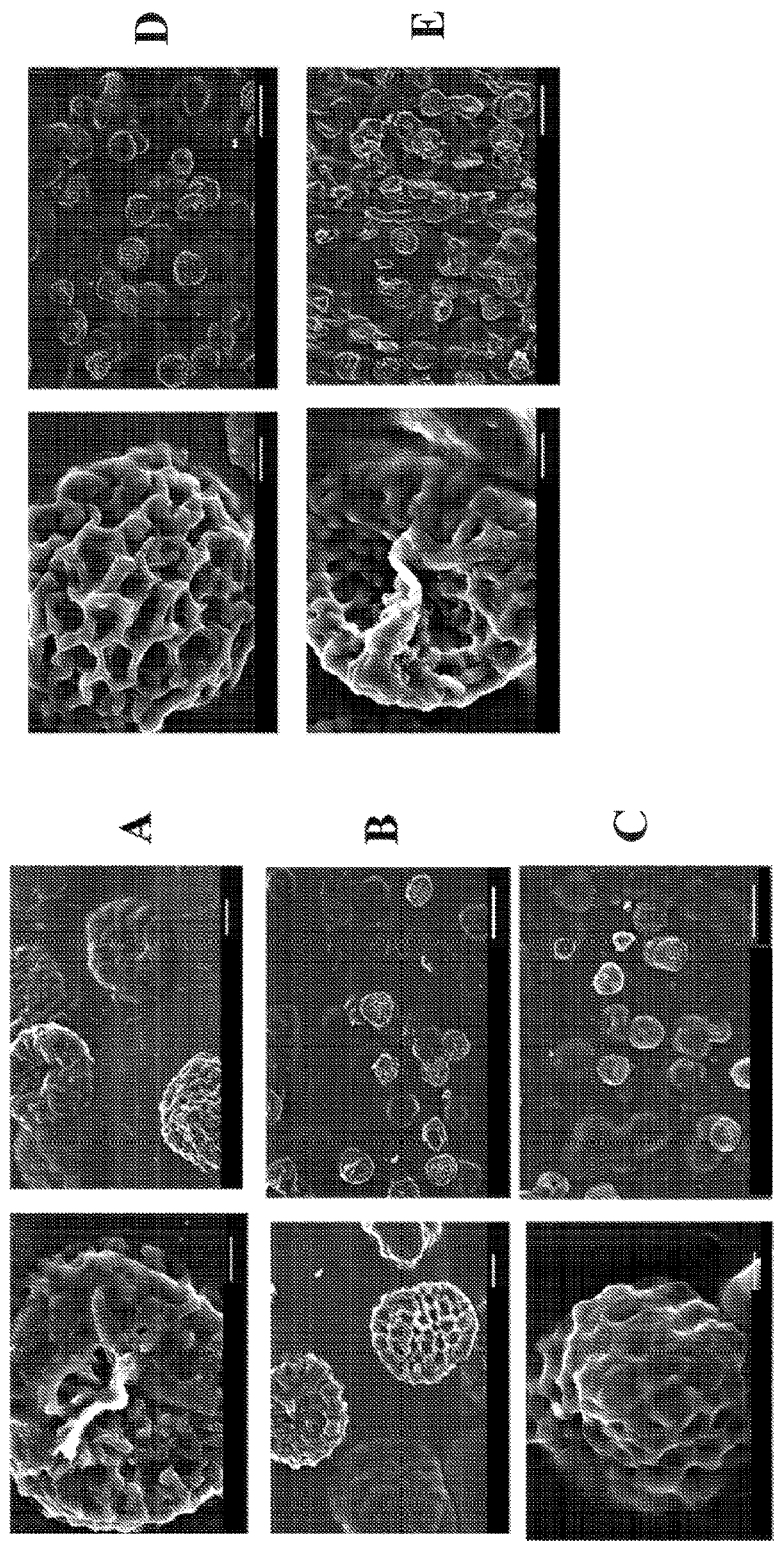
FIG. 6. SEM images of (A) [CEL+5% SEC] composite, (B) [CEL+10% SEC] composite, (C) [CEL+10% EIS@SEC] composite, (D) [CEL+15% SEC] composite and (E) [CEL+33% SEC] composite. Scale bar: A left panel-5 μM; A right panel-10 μM; B left panel-10 μM; B right panel-50 μM; C left panel-5 μM; C right panel-50 μM; D left panel-5 μM; D right panel-50 μM; E left panel-5 μM; E right panel-50 μM.

SEM. SEM images of [CEL+SEC] composites with 5%, 10%, 15% and 33% SEC taken at different magnifications are shown in FIG. 6 as A, B, D and E respectively. For comparison, an image of a [CEL+10% EIS@SEC] composite is also shown as C in the figure. Carefully inspection of these SEM images and those of SEC alone (FIGS. 2C and 2D) reveals that the structure and morphology of SEC remained the same upon encapsulation into the CEL composite, and that for all [CEL+SEC] composites and with various SEC alone (i.e., without EIS) with SEC concentrations ranging from only 5% to up to 33%, interfaces between SEC and CEL polymer matrix can be clearly observed, namely, the polymer matrix pulled away from the SEC surface. These results seem to indicate that the SECs lie in void pockets of the cellulose polymer matrix, and that there does not appear to be any significant molecular interaction between the SEC and cellulose molecules. Detained information on the composites can be obtained by comparing images of CEL composite with 10% SEC alone (i.e, [CEL+10% SEC], FIG. 6B) with those of CEL composite with the same SEC content and with EIS encapsulated in the SEC, i.e., [CEL+10% EIS@SEC], Fig C). Similar to [CEL+SEC] composites with different SECs concentrations, SEC in the [CEL+10% SEC] can be clearly observed in the images. Conversely, at the same SEC concentration level where EIS is encapsulated in the composite ([CEL+10% EIS@SEC]) the images appear to be unfocussed, and SECs cannot be clearly observed. This is as expected because energy from the e-beam in the SEM heats up the composite made some of EIS molecules in in the composite melt as EIS melts at 38° C., thereby making it impossible to focus well on the sample, and to obtain clear images. Taken together, the results clearly reconfirm that the robust nature of SEC enables it to fully retain its structure and morphology even after it is subject to dissolution in [BMIm$^+$Cl$^-$] at 90° C. during the synthesis of the [CEL+SEC] composite, and that it effectively retains EIS in the cavity even during phase transitions.

Figure 7:
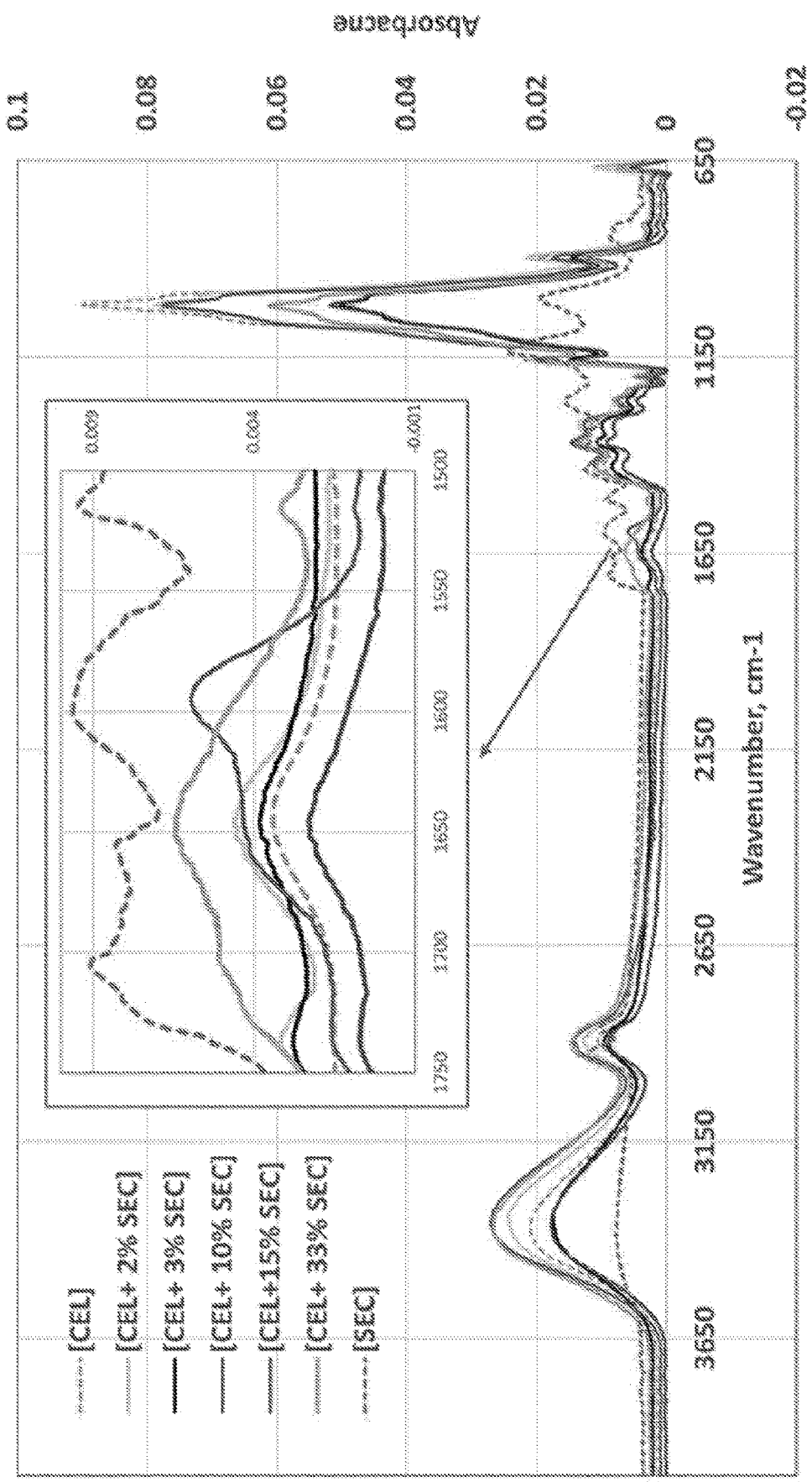
FIG. 7. FTIR of SEC (dashed-line), CEL composite (dashed-line), [CEL+2% SEC] composite (solid line), [CEL+3% SEC] composite (solid black line), [CEL+10% SEC] composite (solid line), [CEL+15% SEC] composite (solid line) and [CEL+33% SEC] composite (solid line).

FTIR. Encapsulation of SECs into the CEL composite was spectroscopically confirmed by FTIR results. This was achieved by comparing the FTIR spectra of SEC powder and [CEL+SEC] composites with different concentrations of SEC. Shown as the dashed spectrum in FIG. 7, SEC exhibits prominent bands at 1704 cm$^{-1}$ and 1654 cm$^{-1}$ that can be attributed to its carbonyl stretching frequency whereas the aromatic C—H out of plane deformation of its phenolic group can be seen in bands at 1595 cm$^{-1}$ and 1514 cm$^{-1}$.[19-21] Since CEL does not have these group, its spectrum (dashed curve) contains a set of different bands, including a band at 2900 cm$^{-1}$ that can be assigned to aliphatic sp$^3$ stretch, a pronounced bands centered at 1050 cm$^{-1}$ that is due to the C—O stretch at C-3 position and a band due to ether bonding at 898 cm$^{-1}$.[5-8] Carefully inspecting the spectra of CEL composite with different concentrations of SECs reveals that SECs were successfully encapsulated into CEL. Specifically, not only that the spectrum of [CEL+SEC] composites contain bands of both CEL and SEC but also that the intensity of the bands due to groups in SEC increases concomitantly with concentration of SEC in the composite. For example, as the concentration of SEC increase from 10% to 15% (solid curve spectra) intensity of the bands due to C—H out of plane deformation of phenolic group at 1595 and 1514 cm$^{-1}$ appeared to grow in intensity relative to other bands due to CEL.

Figure 8:
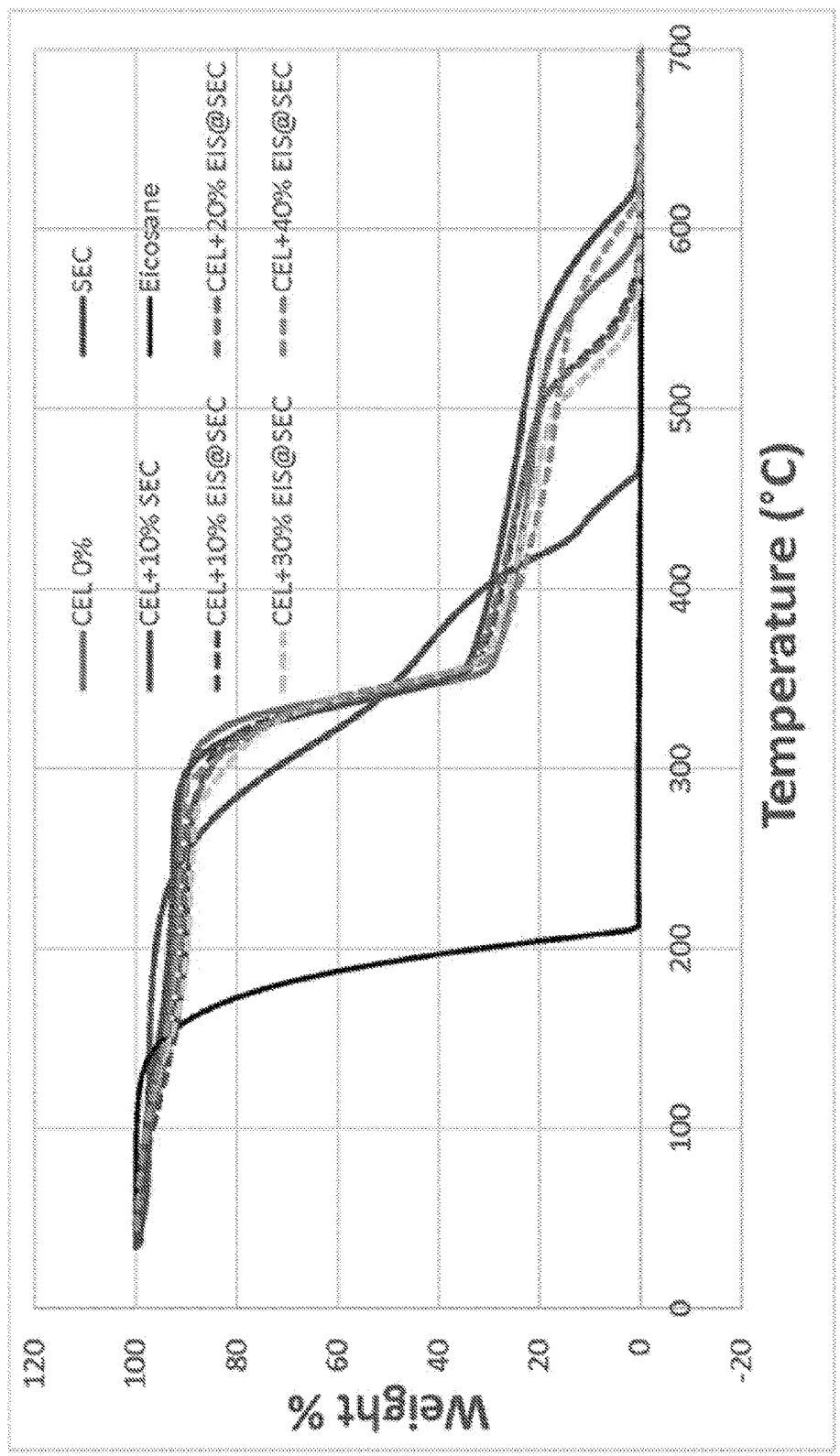
FIG. 8. Thermal gravimetric analysis curves of EIS (black solid line), SEC (solid line), CEL composite (solid line), [CEL+10% SEC] composite (solid line), [CEL+10% EIS@SEC] composite (dashed-line), [CEL+20% EIS@SEC] composite (dashed-line), [CEL+30% EIS@SEC] composite (dashed-line) and [CEl+40% EIS@SEC] composite (dashed-line).

Thermal Gravimetric Analysis (TGA). The effect of SEC encapsulation on the thermal physical property of EIS and [CEL+EIS@SEC] composites was investigated by thermal gravimetric analysis (TGA) measurements. Shown in FIG. 8 are TGA curves of EIS alone, SEC, [CEL+10% SEC] composite, and [CEL+EIS@SEC] composites with 0%, 10%, 20%, 30% and 40% of EIS@SEC. As illustrated, EIS (black solid line) starts to lose weight at approximately 140° C. and it completely loses its weight at 215° C. These results are in agreement with those reported previously.[27,28] Interestingly, when the TGA curve of EIS is compared with those of a CEL composite with only 10% SEC, ie., [CEL+10% SEC] (solid curve), and with 10% EIS@SEC, i.e., [CEL+ 10% EIS@SEC] (puple dashed-line), it is clear that the thermal stability of EIS substantially improved upon SEC encapsulation and subsequent incorporation into the CEL composite. Specifically, similar to the [CEL+10% SEC], the [CEL+10% EIS@SEC] composite remained thermally stable until about 500° C. whereas the composite with just SEC (i.e., [CEL+10% SEC]) does not undergo any mass loss until about 550° C. Since the only difference between these two composites is the presence of encapsulated EIS in the cavity of the SEC, the early mass loss of the [CEL+10% EIS@SEC] composite can, therefore, be attributed to the loss of n-eicosane. The fact that EIS alone underwent complete mass loss at 215° C. even though it remained thermally stable until 500° C. when encapsulated in the cavity of SEC clearly indicates that SEC's compact and rigid cavity not only retains EIS from leaking out when it becomes liquid at T>38° C. and also substantially improves the thermal stability of EIS by keeping it from completely decomposing between 275°-500° C.

The TGA curve of SEC (solid line) exhibits four phases of mass loss. This mass loss pattern is similar to those previously observed for SECs,[18-21, 29, 30] and can be attributed to the loss of physically absorbed water in the first phase between 50-150° C. The second phase from 250-350° C. is probably due to a partial decomposition of the SEC wall material with the loss of some gases such as oxygen.[23, 29, 30] The decomposition continues in the third phase at 350-450° C., and finally, a decomposition of the solid residual in the fourth phase at 450-480° C.[18-21, 29, 30] TGA curves of CEL composite without SEC (solid line) is similar to that observed previously.[5-8,29-31] Moreover, it is also similar to that of CEL composites with different EIS@SEC contents, namely [CEL+10% EIS@SEC] composite (dashed line), [CEL+20% EIS@SEC] composite (dashed-line) [CEL+30% EIS@SEC] composite (dashed-line) and [CEL+40% EIS@SEC] composite (dashed-line). All of them exhibit three phases of mass loss. The first small weight loss observed in the 80-120° C. range can be attributed to the release of moisture from the composites. Subsequently, all composites showed a two-step thermal degradation process with elevating temperature. The first obvious weight loss was found in the temperature range 300-350° C., which was attributed to the onset of cellulose decomposition. The second weight loss peak at 400-530° C. was caused by oxidation and burning of cellulose, and eicosane decomposition for [CEL+EIS@SEC] composites. The results presented show that even though SEC and EIS are relatively less thermally stable thermally than CEL, when they were added to the CEL composite even at concentration as high as 40%, similar to CEL composite, the [CEL+EIS@SEC] composite remained thermally stable up until about 500° C. This means that adding EIS and SECs into the CEL composite does not seem to produce any pronounce effect on its thermal stability.

Figure 9:
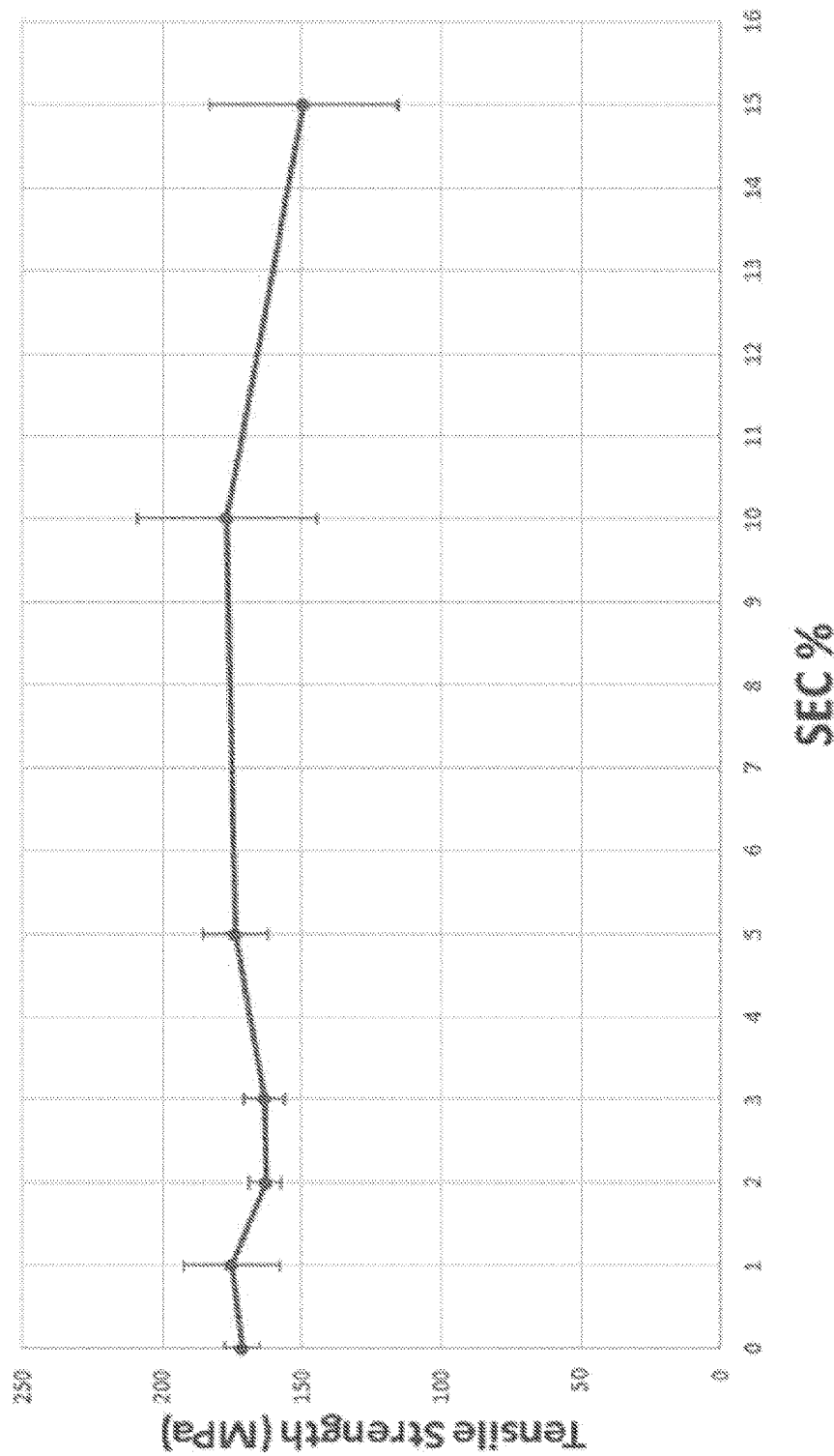
FIG. 9. Plot of tensile strength versus concentration of SEC encapsulated in [CEL] composite.

Tensile Strength. It is possible that adding empty SEC microcapsules into CEL composite may alter its mechanical properties. Measurements were therefore made to determine if adding SECs to CEL composite have any effect on its tensile strength, and if it does, what would be the effect of added SEC concentration. Results obtained (FIG. 9) show that tensile strength values of all CEL composites, without and with different amounts of added SEC, i.e., 1%, 2% 3%, 5%, 10% or 15%, are the same within experimental error. It is, therefore, clear that adding SECs to CEL composite does not produce any significant effect on the tensile strength and mechanical property of the CEL composite at this concentration range. Lack of change in the mechanical property is in agreement with results gained from SEM images, namely, it seems that added SECs fits well into void volume of CEL composite, and because there is no significant molecular interaction between cellulose molecules and SECs, the mechanical property of the [CEL+SEC] composites is similar to that of CEL composite without any SEC.

Figure 10:
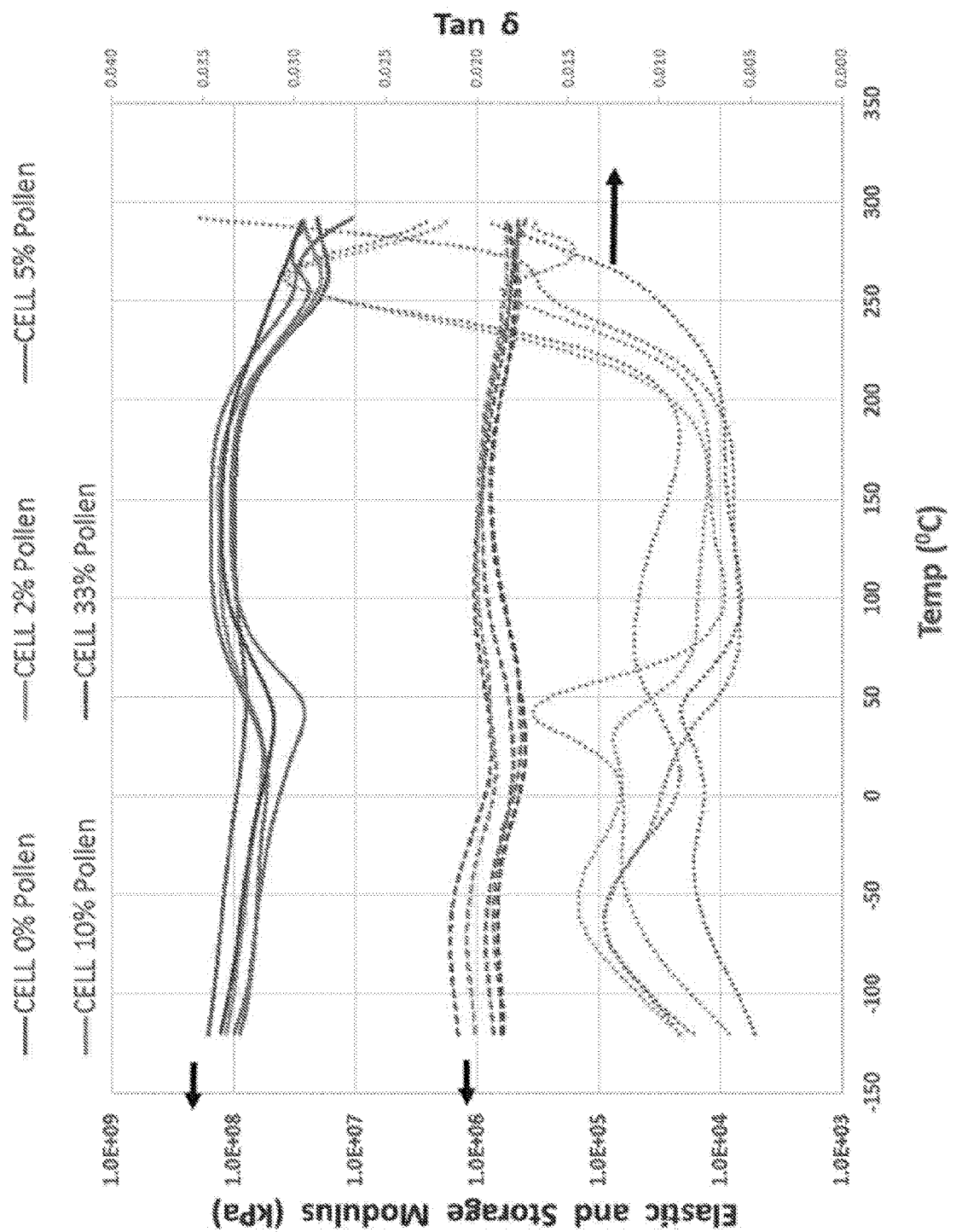
FIG. 10. Plot of Storage or Elastic Modulus (E') (solid line), loss or elastic modulus (E") (dashed line) and tan δ (dotted line) as a function of temperature for CEL composite, [CEL+2% SEC] composite, [CEL+5% SEC] composite, [CEL+10% SEC] composite and [CEL+33% SEC] composite.

Dynamic Mechanical Analysis (DMA). Even though adding SEC does not seem to have any observable effect on the static mechanical property of the CEL composite, it may still produce a change in the viscoelastic properties of the CEL composite. Accordingly, dynamic mechanical analysis (DMA) measurements were carried out on the CEL composites and the [CEL+SEC] composites with 2%, 5% 10% and 33% of SEC concentration. DMA results allow determination of the viscoelastic behavior of materials over a broad temperature range and is strongly sensitive to the morphology and structure of the composites. In the DMA measurements, two different moduli were simultaneously recorded: the storage modulus or elastic modulus E' which provides information on the stiffness of the composite, the loss modulus E" which is for the viscous response of the materials, and tan δ, i.e, the ratio of E" to E which is a useful quantifier of the presence and extent of elasticity. Shown in FIG. 10 are plots of E' (solid curves), E" (dashed-line curves), and tan δ (dotted curves) as a function of temperature for CEL composite without, and with 2%, 5%, 10% and 33% of SEC concentration. As illustrated, in general, both storage and loss modulus for all composites do not seem to change significantly over the temperature range −120° C. to 200° C. There is a slight decrease in both moduli in all composites with temperature up to about 40° C. followed by a recovery before another decrease starting around 200° C. It is general accepted that a modulus must undergoes a change by at least an order of magnitude for it to be considered significant. In this case, the decrease of both moduli at around 40° C. for all composites is only about half or less than half of an order of magnitude. Therefore, it can be assumed that such a minor change is not due to the any change in the rheological property of the composites but probably is due to the fact that the composites became slightly softer and more flexible as they are heated up to about 40° C. The recovery of this slight decrease in the moduli was subsequently observed in the region from around 40° C. to about 100° C. Similar phase change is also observed for the same composites in the TGA (FIG. 8) and can therefore, be attributed to the result of water/moisture leaving the composites as the temperature continued to increase. Any water or moisture in the composites can act as a plasticizer and as the water escaped, the composites became relatively harder and brittle thereby leading to a slight increase in both moduli.

The final decrease in the moduli from about 200° C. may be due to onset of thermal decomposition. According to TGA data (FIG. 8), the composites have not yet undergone thermal decomposition in the region from 200° C. to 250° C. The modulus decrease in this region may be due to the weakening in the structure integrity of the composites which lead to the decrease in storage modulus. That is, the modulus decrease in this region is due to the composites weakening which was induced by heating rather than by CEL polymer chains softening. Finally, as indicated by the TGA results, the composites underwent thermal decomposition into gaseous products at temperature above 250° C. It is, therefore, difficult to interpret the changes on storage modulus, elastic modulus and tan δ in this region.

Taken together, the DMA results agree well with the TGA and the tensile strength results, namely, they all indicate that adding SECs to CEL composite even at SEC content as high as 33% does not appear to produce any significant change to the thermal properties and modulus of the CEL composite.

Differential Scanning calorimetry (DSC): Since it was reported that phase transitions of n-alkanes including EIS are very sensitive to impurity,[34,35] EIS used in this work was recrystallized from methanol, and its purity was verified by GC-MS. Differential scanning calorimetry (DSC) curve of pure EIS is presented as black dashed-line in FIG. 11A. As illustrated, the DSC curve of EIS exhibits two exothermic bands, a narrow band at 33.1° C. and a relatively broader band at 34.0° C. during its crystallization process. This type of bimodal phase transition was widely reported for most of the n-alkane paraffins including n-EIS.[34,35] It has been suggested that EIS presents a rotator phase above the bulk crystallization temperature during the phase transition from liquid to solid. That is, a metastable rotator phase is considered as the orthorhombic rotator phase with respect to the layers.[34-43] As a result, EIS undergoes two phase transitions between the isotropic liquid and stable orthorhombic phases, namely the first transition is from the homogeneously nucleated liquid to the rotator phase, and the second one is from the heterogeneously nucleated rotator phase to the crystalline phase.[34-43] This unusual crystallization behavior in n-alkanes is probably due to the methyl-end with low surface energy or long chain geometrical form of n-alkanes.[34-43] Another possible reason may be that surface freezing can be entropically stabilized by fluctuations along the axis of the molecules.[34-43]

Conversely, and similar to those reported previously, pure EIS exhibits only a single endothermic band at 38.9° C. during the melting process. As listed in Table 1, EIS generates phase change enthalpies of 252.0 and 255.8 J/g during the crystallization and melting processes, respectively. These results clearly indicate that EIS can effectively serve as phase change material for latent-heat storage-release.

TABLE 1

Phase change properties of EIS, EIS encapsulated in SECs (EIS @ SEC) and [CEL + EIS @ SEC] composites with different [EIS @ SEC] contents.

| Compound | $T_c$ (° C.) | $\Delta H_c$ (J/g) | $T_m$ (° C.) | $\Delta H_m$ (J/g) |
|---|---|---|---|---|
| Eicosane | 33.1, 34.0 | 252.0 | 38.9 | 255.8 |
| EIS @ SEC | 33.0, 34.5 | 158 ± 1 | 38.0 | 158 ± 1 |
| CEL + 20% EI @ SEC | 35.39 | 11.68 ± 0.04 | 37.18 | 11.57 ± 0.07 |
| CEL + 30% EI @ EIC | 33.9 | 33.4 ± 0.1 | 38.0 | 32.8 ± 0.2 |
| CEL + 40% EI @ SEC | 34.4 | 40.5 ± 0.1 | 37.4 | 33.7 ± 0.2 |
| CEL + 50% EI @ SEC | 34.6 | 45.9 ± 0.1 | 37.4 | 43.9 ± 0.3 |

Figure 11A:
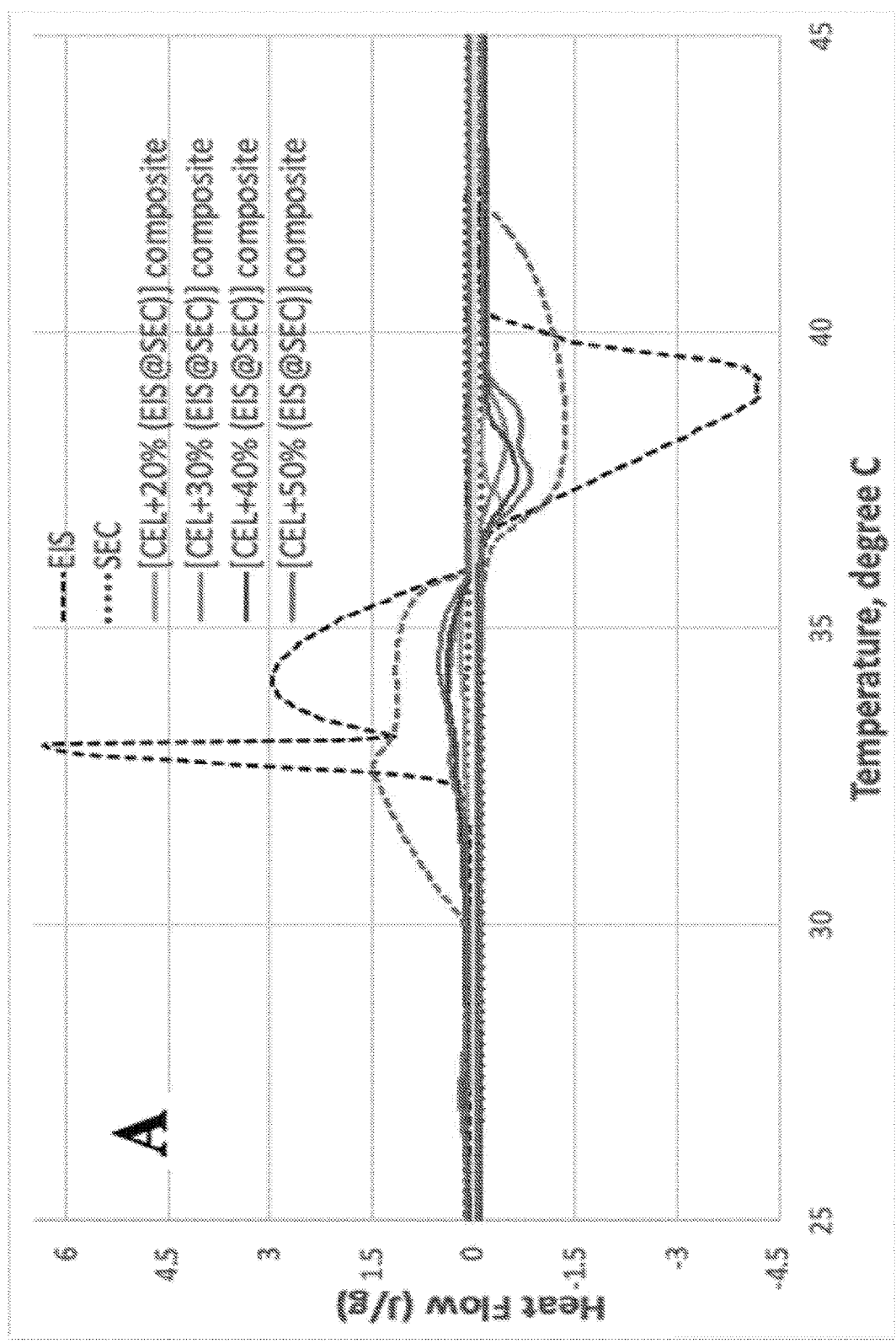
FIG. 11. Different scanning calorimetry curves of SEC (dotted line), EIS (black dashed-line), EIS@SEC (dashed-line) [CEL+20% EIS@SEC] composite (solid line), [CEL+30% EIS@SEC] composite (solid line), [CEL+40% EIS@SEC] composite (solid line) and [CEL+50% EIS@SEC] composite (solid line). (B) is expanded scale of DSC curves in (A) to facilitate clearer visualization of DSC curves of [CEL+SEI@SEC] composites.

Similar to pure EIS, EIS encapsulated in SEC (i.e., EIS@SEC) also exhibits bimodal phase transitions during the crystallization process and a single band during the melting process (dashed-line curve in FIG. 11A). The $T_c$ values for EIS@SEC are 33.0 and 34.5° C. whereas its $T_m$ value was found to be 38.0° C. (Table 1). These values are, as expected, similar to that observed for pure EIS. However, the bands of the DSC curve for EIS@SEC are much broader compared to those of pure EIS. Furthermore, the crystallization enthalpy ($\Delta H_c$) and the melting enthalpy ($\Delta H_m$) values for EIS@SEC were found to be (158±1) J/g and (158±1) J/g which are relatively lower than those found for pure EIS. Using the measured enthalpy values for EIS and EIS@SEC, it is estimated that the amount of EIS encapsulated in the SEC is, at least, about 63% of the weight of the SECs. This value was calculated assuming that SEC shell does not hinder heat absorbed and release by EIS. However, such assumption may not be valid as it is evident from the DSC dotted-line curve of SEC in FIG. 11A, SEC shell does not undergo any phase changes in the DSC scanning temperature range. In fact, it has been reported that heat transfer from and to environment to the core is slowed down when PCM is encapsulated into cavity of microencapsulators,[34, 35, 37, 39, 42, 43] which can also be observed in this case as DSC bands of EIS@SEC are much broader compared to relatively narrower bands of EIS alone. As a consequence, the actual amount of EIS being encapsulated in the SEC may be higher than 65%.

Figure 11B:
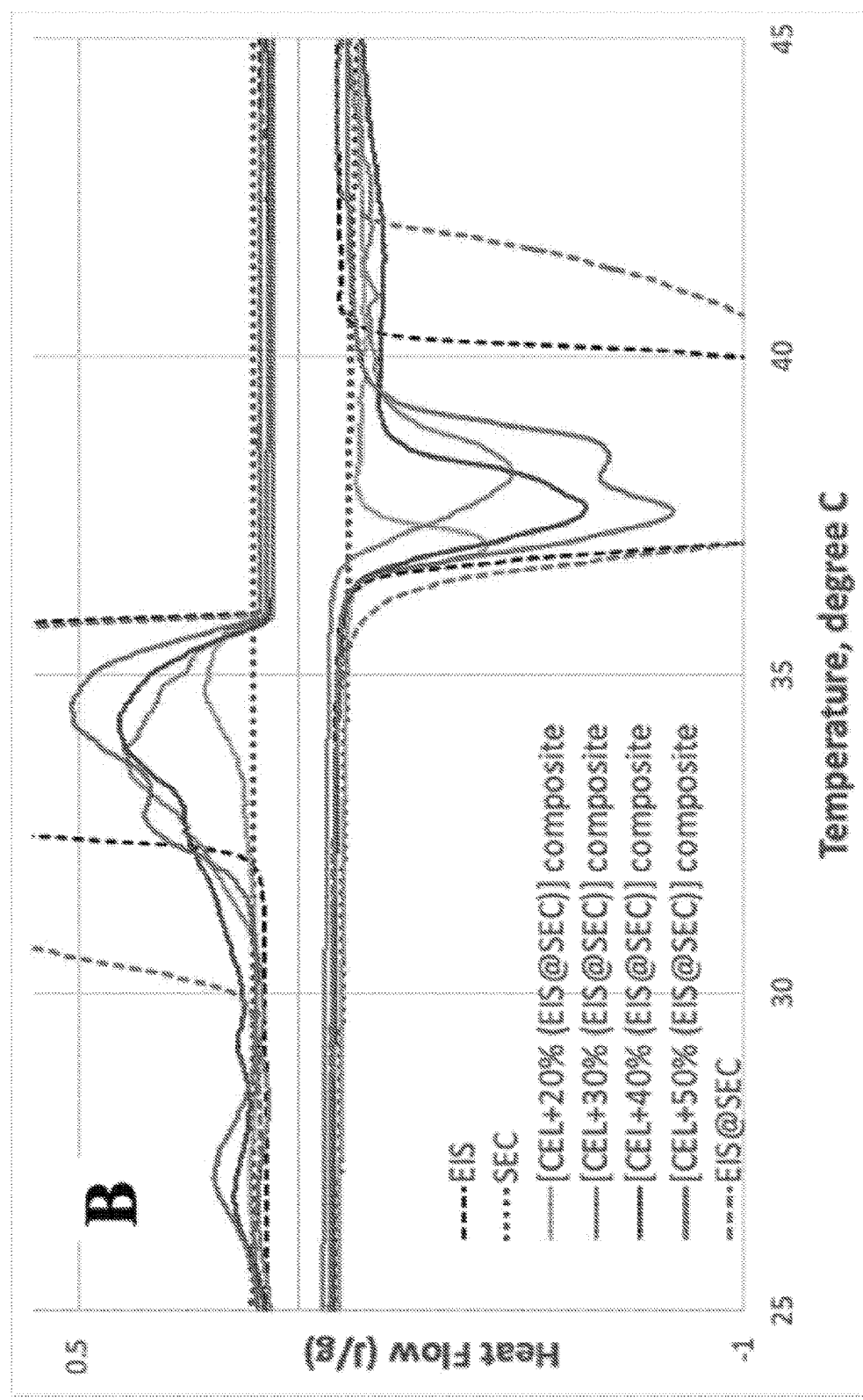

DSC curves of CEL composites with different contents of EIS@SEC are also shown in FIG. 11A. To render clearer visualization of DSC curves of the composites, the scale of FIG. 11A was expanded and shown in FIG. 11B. As expected, the DSC bands of the composites increase concomitantly with the content of EIS@SEC in the composites. Specifically, both exothermic and endothermic bands of [CEL+20% (EIS@SEC)] composite increased when the concentration of EIS@SEC in the composite increased to 30%, and continued to increase as the concentration increased to 40% and then 50%. In fact, it is pleasing to see that EIS fully retains its phase change property when it was encapsulated into SECs, and subsequently when [EIS@SEC] was incorporated into the CEL. That is, EIS undergoes crystallization upon cooling and melting when heated when it was alone as well as when it was encapsulated into SECs, and then in the CEL.

From the DSC curves, the crystallization temperature, $T_c$, and melting temperature, $T_m$, can be obtained together with the associated latent heat, $\Delta H_c$ and $\Delta H_m$. The values obtained are listed in Table 1. EIS has $\Delta H_c$ values of 252.0 J/g and (158±1) J/g when it is alone and when it is encapsulated in the cavity of SEC, respectively. The $\Delta H_c$ value of the [CEL+20% EIS@SEC] composite was found to be (11.68±0.04) J/g. This value increases by at least 3.2 folds to (33.4±0.1) J/g when the EIS@SEC content in the composite increased to 30.0%. Further increase in the EIS@SEC content to 40% and 50% leads to 21% and 13% increase, respectively to (40.5±0.1) J/g and (45.9±0.1) J/g, respectively. Similarly, the melting enthalpy, $\Delta H_m$, also correlates with the content of EIS@SEC in the composites, namely, when EIS is alone and in the cavity of SEC, the $\Delta H_m$ values were found to be 255.8 J/g and (158±1) J/g, respectively. For CEL composites with EIS@SEC content of 20%, 30%, 40% and 50%, $\Delta H_m$ values increase from (11.57±0.07) J/g to (32.8±0.2) J/g, (33.7±0.2) J/g and (43.9±0.3) J/g, respectively. The fact that for all composites with [EIS@SEC] contents ranging from 20% to 50%, the latent heat release and absorbed values were very reproducible and their associated standard deviations were much lower than 1%. This clearly indicates that the composites are very stable and their phase change property are highly reproducible.

The crystallization enthalpy ($\Delta H_c$) and melting enthalpy ($\Delta H_m$) of the [CEL+EIS@SEC] composites are found to decrease significantly in comparison of pure EIS. The decrease of the latent heat of the [CEL+EIS@SEC] composites from EIS alone to EIS encapsulated in the composites cannot be attributed solely to the lower content of EIS in the composites. Another factor leading to the loss of the latent heat are the interactions between EIS and supporting materials which in this case are SEC and CEL. This, in effect, hinders EIS from crystallizing and reducing the enthalpy of the [CEL+EIS@SEC] composites. At the lowest concentration of EIS (20%), the observation that the latent heat of the composite is much lower than expected from the EIS content may be attributed to relatively higher concentration of SECs to EIS that seems to hinder the crystallization of the EIS, thereby leading to a lower than expected latent heat. As expected, at other higher EIS concentrations (20%, 30%, 40% and 50%), there seem to be a correlation of the eicosane concentration with the observed latent heat increases. Additionally, as evident from the DSC curves, the SEC and the CEL do not perform any phase changes. Only the EIS in the core store and release latent heat through phase changes. Therefore, the phase change enthalpies of [CEL+EIS@SEC] composites are mainly determined by the loading of the EIS@SEC in the composites. The efficiency of latent heat release and storage for the [CEL+EIS@SEC] composites was estimated to be about 57% from the cooling and heating enthalpies, the encapsulation efficiency and the content of EIS@SEC in the CEL composite. While this efficiency is not as high as that of pure EIS, it is important to realize that EIS even when it is encapsulated into the cavity of SEC, and subsequently into the CEL composites, still exhibits the same heat-storage and release property as the pure EIS. Considering the superiority of SEC in encapsulation and protection of EIS, and that the [CEL+EIS@SEC] composites are biocompatible, robust, highly stable and reproducible, the phase change efficiency loss of EIS due to encapsulation is totally acceptable in terms of its potential applications in various fields such as smart building materials and textiles as well as biomedicine. Moreover, phase change efficiency of [CEL+EIS@SEC] composites can be readily increased by increasing the loading of [EIS@SEC] in the composites.

Figure 12:
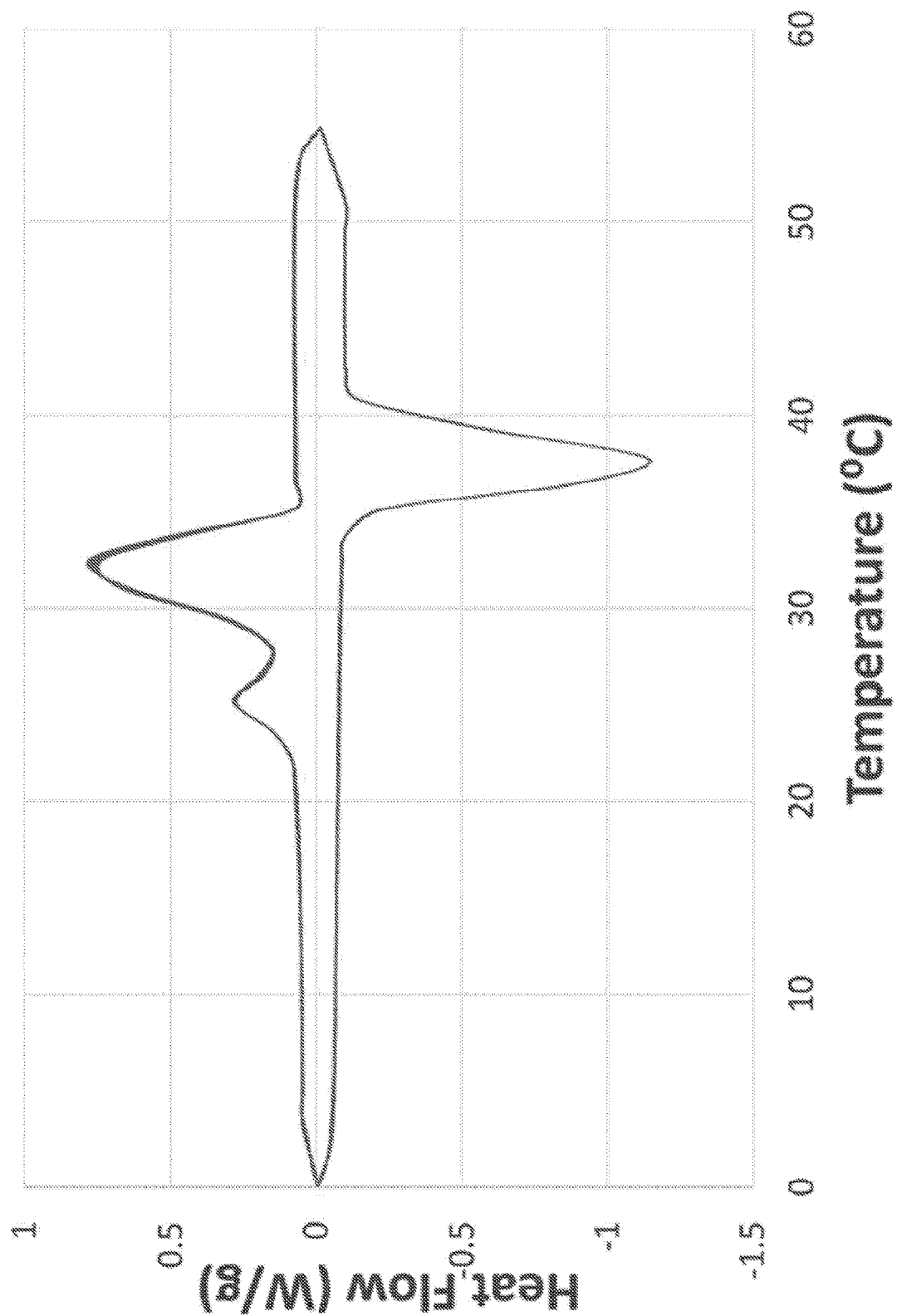
FIG. 12. A collection of 220 of heat-cooling cycles of the [CEL+40% EIS@SEC] composite showing the stable encapsulation during endothermic and exothermic process.

Effectiveness of SEC as a Microencapsulator, and Stability and Reliability of [CEL+EIS@SEC] Composites as Phase Change Material: Heating-cooling cycles of the [CEL+40% EIS@SEC] composite were repeatedly carried out for 220 cycles and their corresponding DSC curves were recorded, and presented in FIG. 12. As illustrated, even after repeatedly being scanned for 220 cycles, which took more than 2 days, the melting and crystallization temperatures, and the enthalpy for heat absorbed and heat release values remained the same. In fact, the differences between the highest and lowest $\Delta H_c$ and $\Delta H_m$ values are just 0.14% and 0.13%, respectively. These results clearly show that SEC effectively protects and keeps EIS in its cavity during phase change transition, and that the [CEL+EIS@SEC] composites are highly stable, reliable and, possess reproducible phase change properties.

Conclusion

In summary, we have shown that natural pollen grains can be effectively cleaned to remove all external and internal cytoplastic material to produce SECs that are empty microcapsules of 25 μm in diameter having extensive networks of ~200 nm diameter holes. Even with the robust cleaning procedure, the SECs obtained fully retain the structure and morphology of the natural pollen grains. SECs are chemically and thermally stable. More importantly, their empty microcavities enable it to serve as microencapsulator. We have demonstrated that a phase change material such as EIS can be successfully encapsulated into the microcavity of the SECs to produce [EIS@SEC] with an encapsulation efficiency of at least 63 wt %. The high stability and robust nature of SECs effectively keeps EIS in its cavity and protects it from elevated temperatures and corrosive environments. As a consequence, the [EIS@SEC] was successfully incorporated into the CEL composite during the synthetic process which involved dissolving CEL in a heated ionic liquid solution of BMIm$^+$Cl$^-$ at 90° C. to produce [CEL+EIS@SEC] composites. Of significance is the fact that SEC not only protects and keeps EIS from leaking out from its microcavity during the phase change transition, but it also enables EIS to fully retain its phase change property. That is, similar to EIS alone, EIS in the [CEL+EIS@SEC] composites undergoes crystallization upon cooling and melting when heated. The energies associated with the crystallization and melting process allow the [CEL+EIS@SEC] composites to fully exhibit the property expected for phase change material, ie., heating the surroundings when it is cold and absorbing energy from the surroundings when it is hot. The efficiency of latent heat storage and release of [CEL+EIS@SEC] composites was estimated to be around 57%. The fact that the DSC curves of the [CEL+EIS@SEC] composites remain the same after being repeatedly scanned through the heating-melting cycle 220 times clearly indicates that SEC effectively retains EIS in its cavity, protects it from leaking, and that the [CEL+EIS@SEC] composites are highly stable and reliable as a phase change material.

The [CEL+EIS@SEC] composites developed here are superior to all other available materials based on microencapsulated phase change because these composites are not only robust, reliable and stable, and have strong mechanical property and are also sustainable and biocompatible because they are synthesized from all naturally abundant materials using a green and recyclable synthesis. Because SEC protects and retains EIS in its cavity, the performance characteristics of these composites are reproducible and much better than other PCMs available, which often suffer from complications associated with decomposition and/or leakage of phase change compounds. These features enable the [CEL+EIS@SEC] composites to be uniquely suited for use as high performance materials for such use as dressings to treat burnt wounds, smart textiles for clothing, and smart materials for buildings and energy storage. These possibilities are the subject of our intense investigation.

Example 2

Biocompatible and Smart Composites from Cellulose, Wool and Phase Change Materials Encapsulated in Natural Sporopollenin Microcapsules Natural pollen grains were cleaned to remove all external and internal cytoplastic materials to produce sporopollenin exine capsules (SECs). SECs are empty microcapsules with extensive networks of holes that are ~200 nm in diameter, which remain intact. Various substances including phase change materials (PCMs) such as n-octadecane (C18), n-eicosane (C20, EIS), n-docosane (C22) or a mixture of them (C18+C22) can be encapsulated into the cavity of SECs. The [EIS (or PCMs)@SEC] was obtained with an encapsulation efficiency of at least 76 wt %. SECs are robust and very stable. They protect encapsulated EIS during phase transitions, so they retain their phase change property, and guard them against corrosive environments and elevated temperatures. [EIS@SEC] can therefore be incorporated into cellulose (CEL) and keratin (KER, from wool) composites using butylmethylimmidazolium chloride [BMIM$^+$Cl$^-$], a simple ionic liquid, as a sole solvent to synthesize [CEL+KER+EIS@SEC] composites. EIS in the [CEL+KER+EIS@SEC] composites behaves similarly to EIS alone. It will melt when heated and crystallize when cooled. Energy resulting from these phase transitions allows [CEL+KER+EIS@SEC] composites, like other PCMs, to warm their surroundings by releasing energy and, conversely, to cool their surroundings as they heat up by absorbing energy. The latent heat storage and release efficiency of the [CEL+KER+EIS@SEC] composites is estimated to be about 80%. After going through the heating-melting cycle 200 times, the DSC curves of the [CEL+KER+EIS@SEC] composites stayed the same. This indicates that SECs are in fact fully and effectively retaining the encapsulated EIS and protecting it from leaking out. The [CEL+KER+EIS@SEC] composites are robust, have strong mechanical properties and possess antibacterial activity. This makes them superior to other microencapsulated phase change materials that are currently available. Furthermore, the composites are sustainable and biocompatible as they are synthesized from naturally abundant materials (cellulose, wool, natural pollen grains, and wax) using a green and recyclable synthesis. More importantly, the fact that not only individual PCM such as EIS but also a mixture of two different PCMs such as a mixture of (C22+C18) can be simultaneously encapsulated into the SEC. These features enable the [CEL+KER+EIS@SEC] composites to be uniquely suited as high performance materials for such uses as dressings to treat infected burn wounds, smart textiles for clothing, smart building materials, and energy storage at any given temperature.

Introduction

Smart materials can detect and respond to ambient temperatures. For example, smart textiles help stabilize the body's temperature by keeping it at a preset value regardless of the ambient temperature. Smart buildings similarly help maintain room temperature. The materials possess such properties because they absorb energy when it is hot and release energy when it is cold. Such materials can offer more bodily comfort in outdoor environments and improve overall energy efficiency indoors. Considerable effort has already gone into making smart materials, with most of them being based on synthetic polymers. This is probably they are relatively easier to produce with specific properties. The downside is that these materials are not biocompatible, which limits their use in medical and food applications where biocompatibility is critical.[1-4] Smart materials derived from natural biopolymers that remain biocompatible are thus highly desired.

We have demonstrated recently that a simple ionic liquid (IL), butylmethylimidazolium chloride [BMIM$^+$Cl$^-$], can dissolve both cellulose (CEL) and keratin (KER) (from either wool, hair, or chicken feathers). Through the use of this IL as the sole solvent, we developed a simple, green and totally recyclable method to synthesize biocompatible composites from all-natural and sustainable biopolymers such as CEL and KER. The composites obtained fully retain the properties of their components, i.e., superior mechanical strength (from CEL), and antimicrobial activity, wound healing, and controlled delivery of drugs (from KER).[5-11] The composites have been successfully used to kill bacteria and fungi and to heal ulcerous and infected wounds.[5-8,11] If these biocompatible composites would also have the ability to control and regulate temperature, they could be used as "smart" material and their use could potentially be extended to various applications including energy storage, smart textiles, and building materials, as well as high performance dressings to cool and heal infected burn wounds. It may be possible to add this property to the composites by synergistically exploring the use of phase change materials and sporopollenin exine capsules.

Phase change materials (PCMs) change their state as the temperature changes.[4,12-14] During the heating process, they absorb and change from the solid phase to the liquid phase. The energy is released back into the environment during the cooling process when the temperatures drops below the material's melting point, causing a reverse from the liquid phase back into the solid phase. The energy being released or absorbed concomitant with the phase change regulates the temperature.[4,12-14]

One of the most commonly used PCMs is Paraffin wax (n-alkane) because it is easily found in nature. This linear hydrocarbon also has a comfortable phase change temperature range for humans that spans 18° C.-36° C., and can also easily be integrated into textiles and building materials.[4,12-14] While much effort has been put into using Paraffin waxes, there have only been a limited number of successes so far. The reason for this is that it is hard to retain Parrafin waxes integrated into the materials when it changes from the solid to the liquid phase.[4,12-14] If PCMs are encapsulated they stand a much better chance of maintaining their solid form while being heated and will also have a larger surface area to accommodate heat transfer. Encapsulation using materials like melamine formaldehyde resin, polyurea-formaldehyde resin, poly(methyl methacrylate) (PMMA) and polystyrene have been attempted.[15-20] These systems, however, need to use synthetic polymeric microcapsules, which are not biodegradable or biocompatible.

Sporopollenin exine capsules (SECs) are spherical microcapsules with hollow cavities. Their diameter is around ~25 µm and they contain a porous wall composed of networks of ~200 nm diameter holes.[21-26] They are made by removing all the internal and external cytoplasmic materials from natural pollen grains. Being made from natural pollen grains also makes the SECs biocompatible.[21-26] They are resilient against high temperatures, acids, alkalis and other chemicals.[21-26] This makes them prime candidates for applications that synthetic microencapsulators cannot be used for and we have already seen some successes in the fields of drug delivery and the food industry.[21-34] For example, it was reported recently that pollen grains can be transformed into soft microgel by de-esterifying pectin molecules on the pollen wall structure.[34] Of particular interest is that it may even be possible to use SECs as natural microencapsulators for PCMs, so that they can be incorporated to yield [PCM@SECs] composites that have the ability to regulate temperature. In fact, recently, we have successfully encapsulated a PCM such as eicosane (EIS), a natural paraffin wax, into the cavity of SEC, and then incorporated [EIS@CEL] into CEL composite, using a green and recyclable synthetic method we previously developed, to produce [CEL+EIS@SEC], the first sustainable and biocompatible phase change material.[35] While the [CEL+EIS@SEC] composite has superior phase change property in terms of efficient energy storage, reliability and reproducibility, it does not have active biological property such as antimicrobial activity which is required for use as biomedical material. Also, it would be important to demonstrate that not only EIS can be encapsulated into microcavity of SECs which limits application of this [CEL+EIS@SEC] composite to regulate temperature at the melting point of EIS. Rather other PCM compound or a mixture of PCMs compounds can also be simultaneously encapsulated as well, so that the composites can be generally used to regulate any temperatures.

The information presented herein is indeed provocative and indicates that it is possible to use all-natural biopolymers such as cellulose and wool, along with natural pollen grains and paraffin wax to synthesize a novel and high-performance biocompatible composite that has antimicrobial activity, the ability to provide the controlled delivery of drugs, and the ability to assist in the regulation of temperature. Such considerations prompted us to initiate this study which aims to hasten the breakthrough by systematically developing a novel method to synthesize biocompatible composites from sustainable and all-natural polysaccharide (CEL) and protein (keratin (KER) from wool), natural pollen grains, and a natural PCM such as paraffin wax; e.g., eicosane. Specifically, we (1) developed a method to process Lycopodium clavatum powder, natural pollen grains from clubmoss, to produce SECs; (2) encapsulated not only a single PCM compound such as n-eicosane (EIS) but also a mixture of other PCM compounds into SECs to produce [EIS (or PCMs)@SEC]; and (3) incorporated [EIS (or PCMs)@SEC] into [CEL+KER] composites. Such composites would have unique properties which no other pollen-based composites including soft pollen hydrogels have. They are sustainable, biocompatible, robust, antimicrobial activity, delivery of drugs, regulate and controlled temperature. The synthesis, characterization, and properties of the [CEL+KER+EIS@SEC] composites, especially their phase change property, are reported herein.

Materials and Methods

Chemicals. Cellulose (microcrystalline powder, Avicel, DP□300) was used as received from Sigma-Aldrich (Milwaukee, WI). Lycopodium clavatum powder, orthophosphoric acid (85%), potassium hydroxide, acetone, and ethanol were obtained from Fischer Scientific Company (USA). Sodium hydroxide (98%), HCl (37%), and Malachite green oxalate were purchased from ACROS Organics. 1-Methylimidazole and n-chlorobutane (Alfa Aesar, Ward Hill, MA) were distilled and for subsequent use in the synthesis of n-butyl methylimidazolium chloride [BMIM$^+$Cl$^-$] using previously reported method.[5-11] n-octadecane (C18), n-eicosane (C20 or EIS) and n-docosane (C22) were purchased from Alfa Aesar, and recrystallized from methanol. Their purity was verified by GC-MS. Untreated raw sheep wool, obtained from a local farm, was cleaned using previously reported method.[5-11] Essentially, the raw wool was initially cleaned by Soxhlet extraction with a 1:1 (v/v) acetone/ethanol mixture at 80° C. for 48 h, rinsed with distilled water and then dried at 100±1° C. for 12 h.[5-11]

Instruments. X-ray powder diffraction (XRD) measurements were made on a Rigaku MiniFlex II diffractometer equipped with Ni-filtered Cu Kα radiation (1.54059 Å) with the X-ray tube operated at 30 kV and 15 mA. Samples were measured in the 2θ range of 5.0-50.0° at a scan rate of 2°/min. Data were processed using the Jade 8 program. FTIR spectra in the 650 to 4000 cm$^{-1}$ range were recorded with 4 cm$^{-1}$ resolution on a Perkin Elmer Spectrum 100 FTIR spectrometer using the ATR method. Scanning electron microscopy (SEM) images of the raw pollen grains, SEC, and the composites were taken under vacuum with a JEOL JSM-6510LV/LGS scanning electron microscope with standard 2$^{nd}$ electron and backscatter electron detectors. An Emitech K575x Peltier Cooled Sputter Coater (Emitech Products, TX) was used to apply 20 nm gold-palladium coating were onto the surfaces of composites to render them conductive for measurements.

An Instron 5500R tensile tester (Instron Corp., Canton, MA), equipped with a 5.0 kN load cell and operated at a crosshead speed of 0.5 mm min$^{-1}$, was used to measure tensil strength of the composites. Fluorescence confocal images were recorded on a Nikon Eclipse Ti-E inverted microscope from Nikon using a 60× water objective. The microscope was equipped with Cascade blue (375-420 nm), FITC (494-518 nm) and Texas Red (595-613 nm) laser lines. Images, obtained with a scan speed of 32 fps, were analyzed and processed using NIS Elements—Microscope Imaging software by Nikon.

Thermogravimetric analysis (TGA) of the composites was measured on a Thermal Analysis (TA) TGA instrument (model Q5000) using a platinum pan and at a heating rate of 20.0° C./min (to 800.00° C.) under a continuous flow of 10.0 mL/min of nitrogen gas.

Differential scanning calorimetry (DSC) was used to measure the phase change transition of EIS, [CEL+KER+EIS] and [CEL+KER+EIS@SEC] composites. Two different DSC instruments were used for measurements: a TA Q2000 DSC instrument or a Mettler Toledo DSC822e instrument. Measurements were made with aluminum sample pan in a nitrogen atmosphere and a static nitrogen flow of 50.0 mL/min. The sample was initially equilibrated isothermally at 0.00° C. for 2.0 min, heated to 60.00° C., and then isothermally equilibrated for 1.0 min prior to cooling down to 0.0° C./min. Both heating and cooling rate were 2.0° C./min.

Procedure to clean natural pollen grains to produce empty Sporopollenin Exine Capsules (SECs). Previously reported procedures were used to process natural pollen grains.[21-26, 35] 25.0 g of *Lycopodium clavatum* pollen grains was stirred in acetone under reflux (450 mL, 65° C.) overnight. It was then filtered under vacuum and air dried for 12.0 h. The pollens were then added to a 6% w/v orthophosphoric acid solution (450 mL) and stirred for 7 days at 60° C. Subsequently, the pollens were filtered and sequentially washed with hot water (2×250 mL), acetone (250 mL), 2M HCl (250 mL), 2M NaOH (250 mL), water (6×250 mL), acetone (250 mL) and ethanol (250 mL). Subsequent to being dried overnight, the pollens were transferred to 6% w/v KOH aqueous solution at stirred at 80° C. for 12.0 h. The pollens were then vacuum filtrated, washed with hot water (6×250 mL), acetone (250 mL), hot ethanol (250 mL) and finally dried at 60° C. until constant weight. The SECs obtained was a fine brown powder (7.78 g, 31% yield). It is noteworthy to add that there were reports which initially treated pollens with alkaline (KOH solution) prior to acidolysis step (orthophosphoric acid).[23,24] However, we as well as other groups found that it is of advantageous to clean the pollen with orthophosphoric acid solution before KOH solution as raw pollens were found to undergo changes in the external SEC morphology and microstructure.[21, 22, 25, 26, 35]

Encapsulation of Dye into cavity of SECs. Malachite green was encapsulated into the cavity of the SECs at a ratio of 1 g dye/g of SEC to render visualizing of the SECs inner cavity. Using previously reported procedure,[30, 31, 34] 1 g of SECs was added to ethanolic solution of the dye (0.5 g/mL) to produce a loading of 1 g of dye/g of SEC. The solution was stirred under vacuum for 2.0 hr.[29,30] The SECs were then washed twice with ice cold water to remove any surface adsorption and then dried at 70° C. until constant weight.

Encapsulation of Phase change materials into SECs. Two different phase changes materials were used in this work: either n-eicosane (EIS) or a mixture of n-docosane: n-octadecane (C22+C18). Initially, either EIS (or a 6:4 (w/w) mixture of (C22+C18)) and SECs were finely mixed at a ratio of 2 g of EIS (or (C22+C18)/1 g of SEC at room temperature and placed into a round bottom flask. The solid mixture was gently stirred at 70° C., under vacuum for 3.0 h. Subsequently, the EIS (or (C22+C18)) loaded SECs (i.e., [EIS or (C22+C18)@SEC] were washed twice ethanol (2 mL/10 mg for 5 min) to remove any possible traces of EIS (or (C22+C18)) adsorbed onto surface of SECs. The suspension was filtered, and the (EIS or (C22+C18)@SECs) obtained was air-dried overnight. To increase the amount of EIS (or (C22+C1)) encapsulated in SEC, the mixing and heating under vacuum cycle was repeated several times with higher EIS and SEC ratio. Specifically, encapsulation was carried out initially at a ratio of 3 g of EIS/1 g of SEC. The mixture was mixed, heated under vacuum similar to that used for 2 g/g but for 5 h. Subsequently, additional EIS at a ratio of 1.5 g/g was added to the [EIS@SEC] obtained, mixed and heated under vacuum for 3 h. Lastly, another portion of EIS at a ratio of 1 g of EIS/g of SEC was added to the mixture, mixed and heated under vacuum for 3 h before being washed with ethanol. XRD diffractograms of the (EIS or (C22+C18)@SECs) are used to confirm that the PCMs were encapsulated into the cavity of the SECs, and SEM images will verify that there was no PCMs adsorbed on the surface of the SECs.

Synthesis of [CEL+KER] and [CEL+KER+SEC] composites. [CEL+KER] and [CEL+KER+SEC] composites were successfully synthesized using a procedure previously used in our lab.[5-11] As shown in FIG. 1, [$BMIM^+Cl^-$] was heated to 120° C. and the clean wool was added in portion of 1% w/w under vigorous stirring up to 3% w/w. After 4.0 h a viscous light-yellow solution, without any visible fibers, was obtained. The temperature was then decreased to 100° C. and cellulose was added (3% w/w). For [CEL+KER] composite, the mixture then was casted into] PTFE mold. For [CEL+KER+SEC] composites, an appropriate amount of SECs (1%, 3%, 5%, 10%, 15%, 20%, 30%, 33%, 40% or 50% w/w) was added to the solution only when KER and CEL were completely dissolved and the solution had been allowed to cool to 90° C. The [$BMIM^+Cl^-$] solution of [CEL+KER+SEC] was then cast into PTFE molds. The amount (g) of mixture poured into each mold was kept constant to maintain constant thickness of the composite films. The mixture was allowed to undergo gelation at room temperature for 24 h. The IL was removed from the composite films by washing the films with water using procedure previously used in our lab[37]. Washing water was repeatedly replaced with water every 24 h until it was confirmed that IL was not detected in the washed water (by monitoring UV absorption of the IL at 290 nm). It is estimated that if any [$BMIM^+Cl^-$] remains, its concentration would be smaller than 2 μg/g of the composite film. Since this concentration is two orders of magnitude lower than the $LD_{50}$ value of the [$BMIM^+Cl^-$], if any IL remains in the composite films, it would not pose any harmful effect.[37] The wet films were then dried in an oven under a lead brick at 70° C. for 5 days to obtain the [CEL+KER+SEC] dry films.

Synthesis of [CEL+KER+EIS (or (C22+C18)@SEC)] Composites. Procedure similar to that used to synthesize [CEL+KER+SEC] composites was used to synthesize [CEL+KER+EIS or (C22+C18)@SEC] composites. Briefly, wool and cellulose were completely dissolved in [$BMIM^+Cl^-$] using the procedure described above. The solution was allowed to cool to 90° C. as before. Appropriate amount of either [EIS@SEC] or [(C22+C18)@SEC] was then added and the mixture was stirred for 2 min, followed promptly by casting into PTFE molds. The mixture was then allowed to undergo gelation at room temperature for 24 h as before. The gel films were washed with water for 72 h to remove [$BMIM^+Cl^-$], and then dried under a lead brick under vacuum at room temperature for 1 day to obtain the [CEL+KER+EIS or (C22+C18)@SEC] dry films.

Results and Discussion

Procedure to Clean *Lycopodium Clavatum* Pollens to Yield Sporopollenin Exine Capsules (SECs). As described in the Experimental Section, *Lycopodium Clavatum* raw pollens were initially washed with acetone for 12 h to remove fatty substances. They were subsequently washed with 6% orthophosphoric acid at 60° C. for 7 days to remove the proteinaceous materials from within the pollens. Any residual proteins and the cellulosic intine were finally removed by washing with 6% KOH aqueous solution at 60° C. for 12 h. The fact that this cleaning procedure effectively removed all exine and intine materials from the raw pollens to produce empty sporopollenin exine capsules (SECs) is confirmed by comparing SEM and confocal fluorescence images of the raw pollens (FIGS. 14A and 15A, respectively) to those of the treated pollens, i.e., SECs (FIGS. 14B and 15B). As illustrated, it is clear that this robust cleaning procedure effectively removed all exine materials and opened up the pollens. To facilitate observation of the interior of the sporopollenin, we gently ground the SECs, and the SEM images of the ground SECs are shown in FIGS. 14C and 14D. It is evident that this cleaning method effectively removes all intine materials from the pollens to produce empty SEC. More importantly, given that SEM images of SEC are comparable to images of raw pollen we can determine that the SECs kept their native structure and morphology even after undergoing this robust treatment. This can be seen in the confocal fluorescence microscopic image of the SEC that was stained with Malachite green in FIG. 15B when compared to the unstained raw pollen image in FIG. 15A. The images show that the cytoplasmic materials interior to the pollen were effectively removed during the cleaning process, resulting in SECs that are empty spherical microcapsules.

Figure 16:
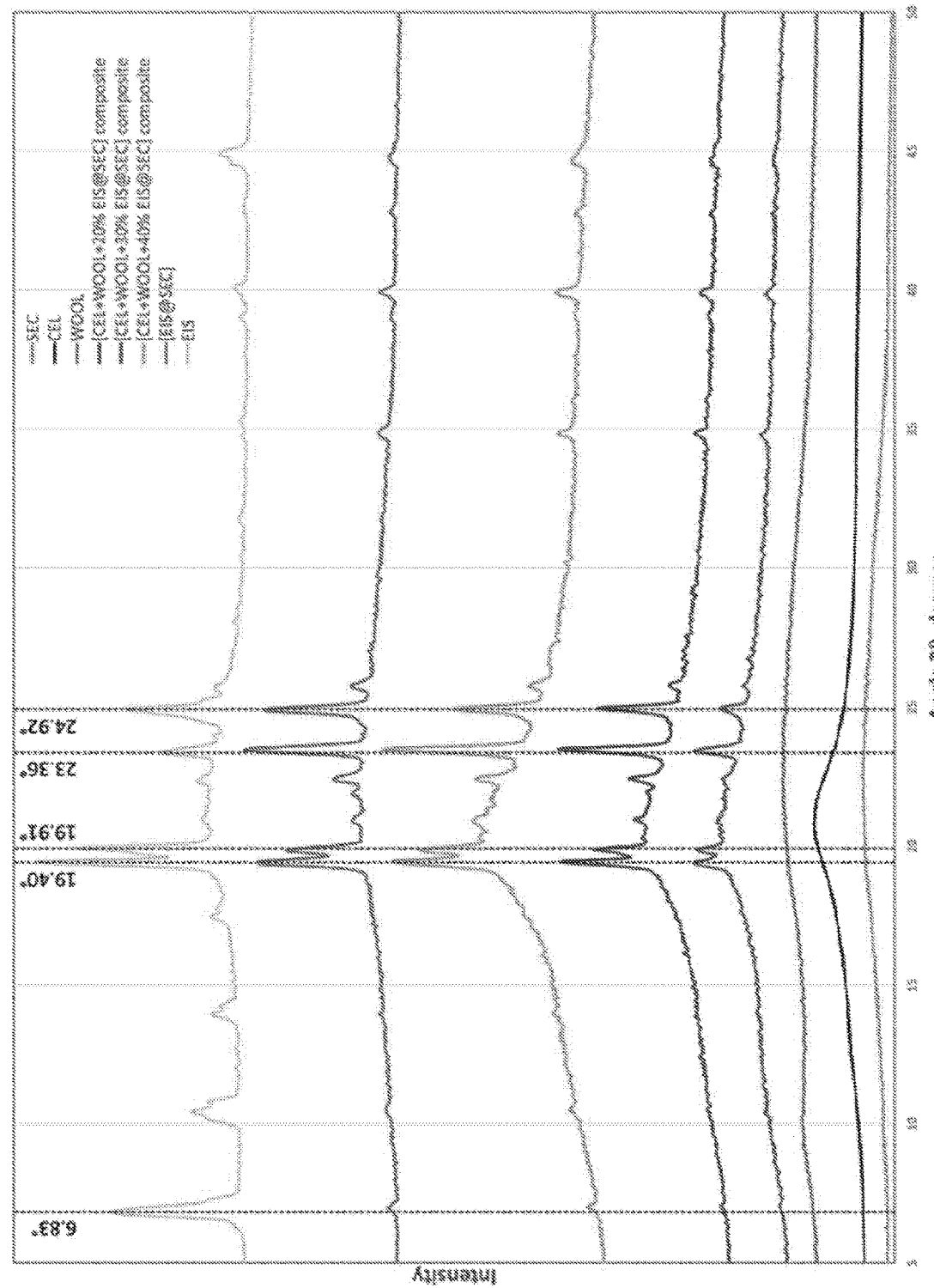
FIG. 16. Powder X-ray diffractograms of CEL (black), raw wool, SEC, EIS, [EIS@SEC], [CEL+KER+20% EIS@SEC] composite, [CEL+KER+30% EIS@SEC] composite and [CEL+KER+40% EIS@SEC] composite.

Encapsulating Phase Change Material into Cavity of SECs. Paraffin wax was used as the phase change material because they are readily available from nature. n-eicosane was used as it has a melting point at 38° C., which is the same as body temperature, making it particularly suited for use in the regulation of temperature in smart textile or smart building materials. As described in the Materials and Methods Section, EIS was encapsulated into the cavity of the SECs by heating under vacuum. Success of the encapsulation can be verified by comparing the powder X-ray diffractogram of [EIS@SEC] to that of EIS alone and SEC alone. As illustrated in FIG. 16, SEC, being amorphous, exhibits only very broad XRD band. Conversely, EIS with its crystalline structure exhibits XRD diffractogram with many discrete bands, e.g., the most pronounced bands are at 2θ values of 6.83°, 19.40°, 19.91, 23.36° and 24.92°. As expected, when EIS was encapsulated into microcavity of SEC, XRD diffractogram of the [EIS@SEC] also exhibits the same five pronounced crystalline bands due to EIS which can be clearly seen as in the figure as five vertical lines in the figure. Furthermore, these five discrete bands are riding on top of a broad background band which is similar to the XRD curve of SECs alone. Taken together, these results clearly indicate that EIS was successfully encapsulated into the cavity of the SECs.

Figure 14:
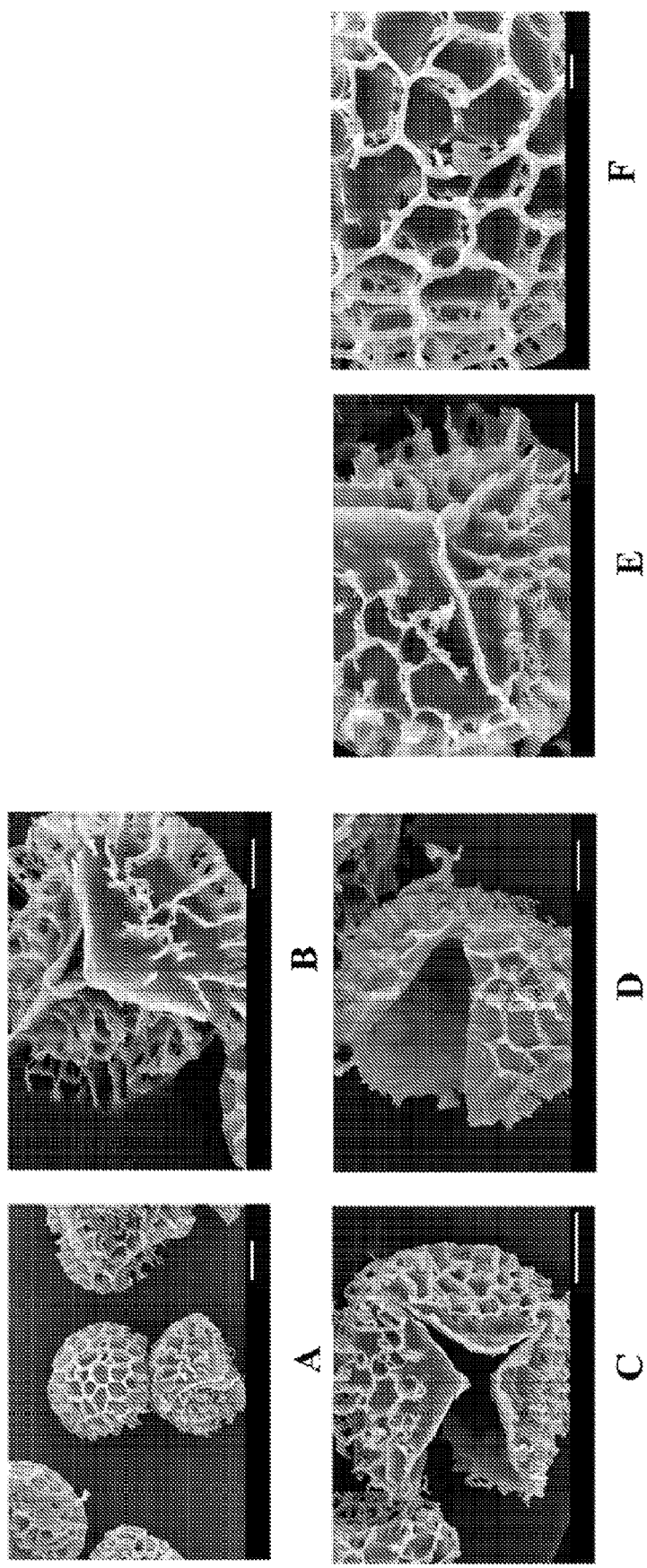
FIG. 14. SEM images of intact natural pollen grains (A), sporopollenin (SEC) (B), ground SECs (C and D), and n-eicosane (SEC) encapsulated in SEC (E, F). Scale bar: A-10 μM; B-5 μM; C-10 μM; D-5 μM; E-5 μM; F-2 μM.
Figure 15:
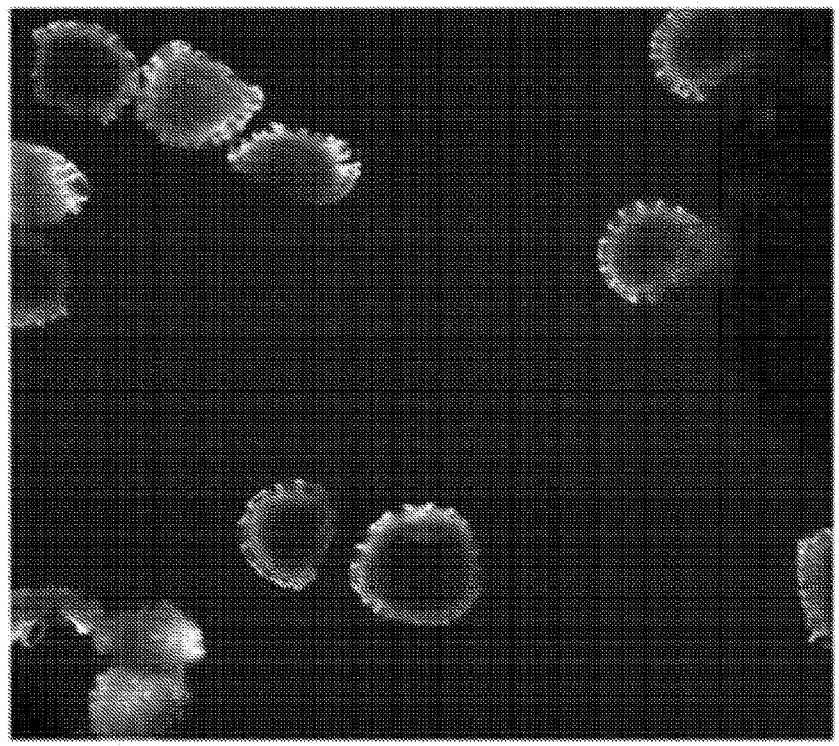
FIG. 15. Confocal fluorescence microscope images of intact pollens (A) and treated pollens or SECs (B).
Figure 15:
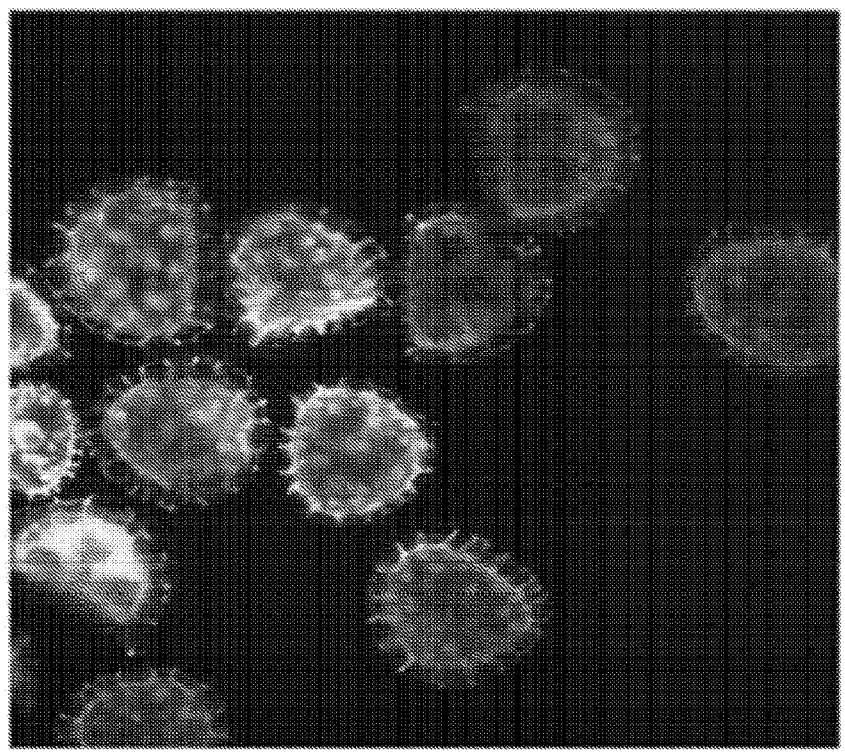

After encapsulating EIS into SEC, the [EIS@SEC] was washed thoroughly. It is possible, though, that some EIS may remain adsorbed on the surface of the SEC.[26] SEM images of [EIS@SEC] were compared to those of SEC in order to investigate this possibility. As seen in FIG. 14, the SEM images of [EIS@SEC] (14E and 14F) are very clear and very similar to those of SEC (14C and 14D). This shows that no EIS remained adsorbed on the SEC's surface, which means that the EIS was effectively encapsulated into the SEC's cavity.

Figure 13:
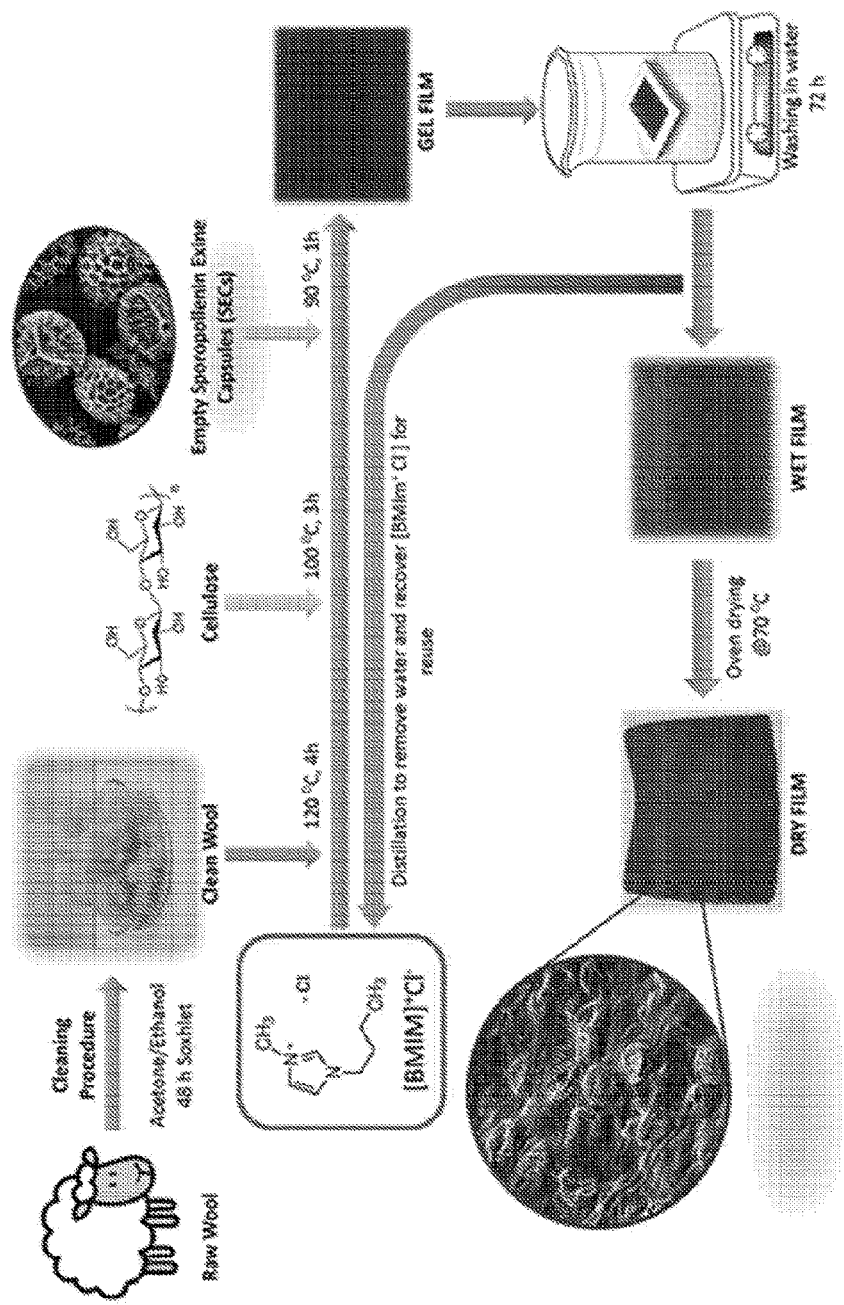
FIG. 13. Schematic diagram of the procedure used to purify natural pollen grains and synthesize [CEL+KER+SEC] composites.
Figure 21:
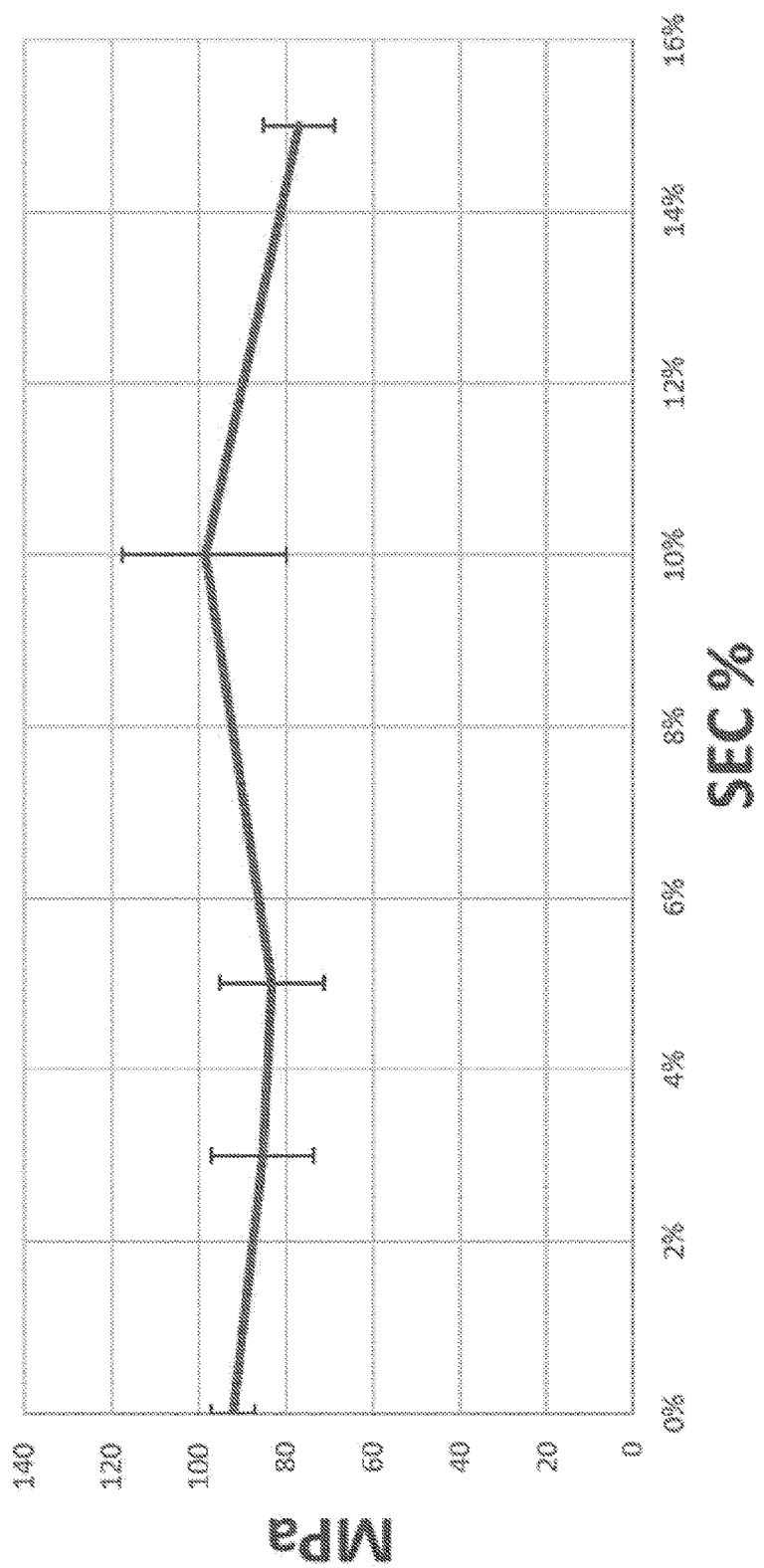
FIG. 21. Plot of tensile strength versus concentration of SEC encapsulated in [CEL+KER] composites.

Synthesis and Characterization of [CEL+KER+SEC] Composites and [CEL+KER+EIS@SEC] Composites. As illustrated in FIG. 13 and described, in details, in the Materials and Methods Section, the same procedure was used to prepare [CEL+KER+SEC] composites and [CEL+KER+EIS@SEC] composites. Photographs of [CEL+KER+EIS@SEC] composites with different contents of [EIS@SEC] are shown as FIG. 21. Because the melting point of EIS is 38° C., and since in the synthesis of [CEL+KER+EIS@SEC] composites, [EIS@SEC] was added to the [BMIM$^+$Cl$^-$] solution of CEL+KER at 90° C., it is possible that some EIS may have melted at this temperature and leaked out of the SEC's cavity. This possibility was explored by using XRD diffractograms of [CEL+KER+EIS@SEC] composites contain different ratios of [EIS@SEC]. Results are shown in FIG. 16 for [CEL+KER+20% EIS@SEC] composite, [CEL+KER+30% EIS@SEC] composite and [CEL+KER+40% EIS@SEC] composites together with [EIS@SEC]. The fact that all three [CEL+KER+EIS@SEC] composites have the same discrete bands, which are characteristic of EIS, and that band intensity correlates with [EIS@SEC] concentration in composite clearly demonstrated that EIS stayed in the SEC's cavity throughout the synthetic process during which the [EIS@SEC] was exposed to temperatures as high as 90° C.

Figure 17:
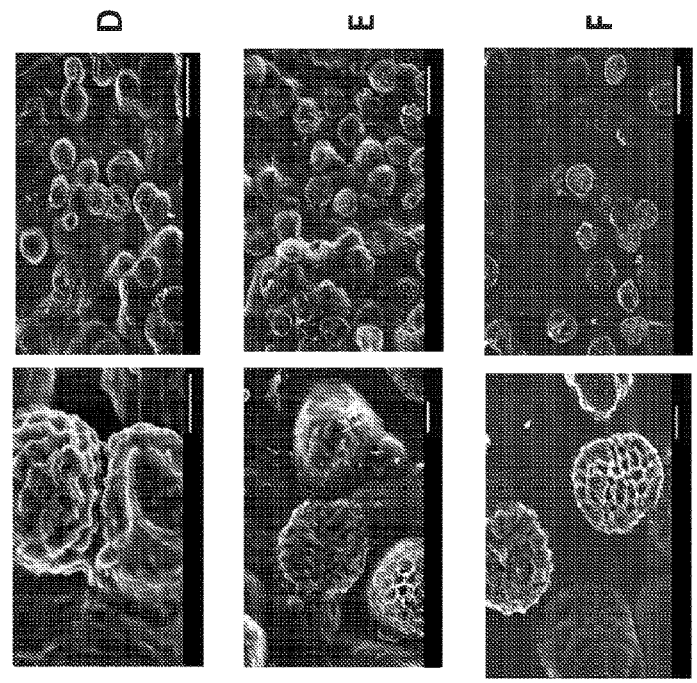
FIG. 17. SEM images with high magnification (left column) and low magnification (right column) of (A) [CEL+KER+5% SEC)] composite, (B) [CEL+KER+10% SEC)] composite, (C) [CEL+KER+15% SEC)] composite, (D) [CEL+KER+30% SEC)] composite and (E) [CEL+KER+50% SEC)] composite. (F) [CEL+10% SEC] composite. Scale bar: A left panel-10 μM; B right panel-50 μM; B left panel-5 μM; C right panel-50 μM; C left panel-10 μM; D right panel-50 μM; D left panel-10 μM; A right panel-50 μM; E left panel-10 μM; E right panel-50 μM; F left panel-10 μM; F right panel-50 μM.
Figure 17:
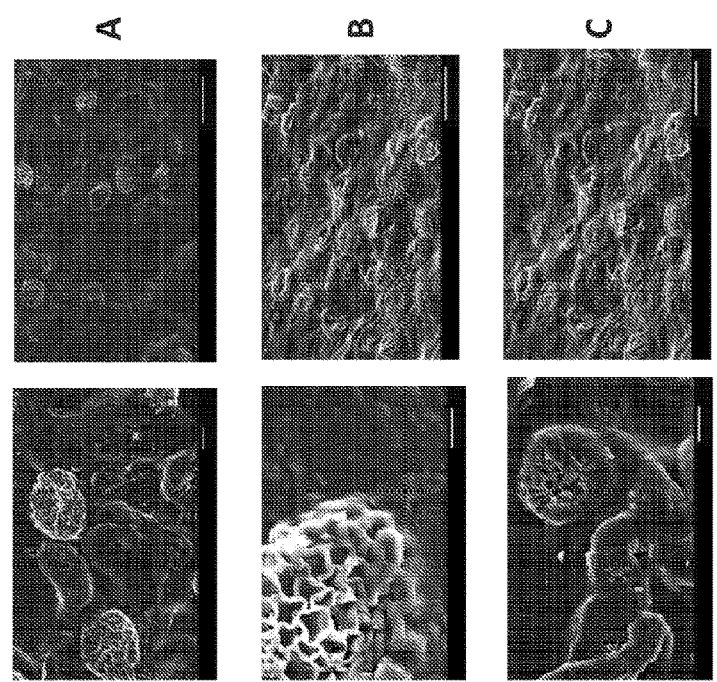

SEM. FIG. 17 shows SEM images of [CEL+KER+SEC] composites with 5%, 10%, 15%, 30% and 50% SEC taken at different magnifications. When compared, the SEM and SEC images (FIGS. 14C and 14D) show that the SECs maintained similar structure and morphology upon incorporation into the [CEL+KER] composites. Upon careful inspection of these SEM images, it was found that there may be some interactions between SEC and the polymer matrix of the [CEL+KER]. To gain insight into the interactions, we synthesized a similar composite but without KER, i.e., [CEL+10% SEC] composite, and the SEM of this composite was taken and presented as F in FIG. 17. It seems that for this composite the polymer matrix pulled away from the SEC surface. The SECs appear to lie in the void pockets of the cellulose polymer matrix and there does not appear to be any notable molecular interactions occurring between the cellulose molecules and the SECs. Conversely, for a similar composite but with KER, i.e., [CEL+KER+10% SEC] composite, shown as B in FIG. 17, there seem to be some interactions between the SECs and the [CEL+KER] polymer matrix. These results seem to indicate that rather than the polysaccharide molecules of the CEL, it is the protein molecules of KER that form some molecular interactions with the SECs. This is hardly surprising considering that the SECs with their carbonyl and phenol group can readily interact with the protein molecules of KER. Taken together, the [CEL+KER+SEC] composites are superior to composites containing only CEL or KER with SEC, i.e., [CEL+SEC] and [KER+SEC] composites, respectively. This is because, as described in the Introduction section, adding KER to CEL make the composites rheologically and mechanically stronger (from inherent property of CEL and interactions between KER and SEC), while retain antimicrobial activity, wound healing, and controlled delivery of drugs (from KER).

FTIR. FTIR spectra of [CEL+KER+SEC] composites with different contents of SECs (10%, 15%, and 33%) together with those of CEL composites, raw wool, and SEC are presented in FIG. 18. The spectrum of raw wool (dashed curve) exhibits characteristic bands that are primarily assigned to the vibrational modes of peptide bonds in KER. For example, the bands at 1636 cm$^{-1}$ and 1513 cm$^{-1}$ are due to amide C=O stretch (amide I) and C—N stretch (amide II) vibrations, respectively.[5-11] In addition, a peak at 3277 cm$^{-1}$ can be assigned to N—H stretch vibration (amide A) whilst a band at 1386-1235 cm$^{-1}$ can be assigned to the in-phase combination of the N—H bending and the C—N stretch vibrations (amide III). This finding is expected since wool is composed of more than 95% keratin protein.[5-11] It is noteworthy that the FTIR spectrum of wool does not possess any peak at 1745 cm$^{-1}$, which is ascribed to lipid ester carbonyl vibrations.[5-11] This demonstrates the effectiveness of the Soxhlet extraction method in removing any residual lipids from the wool.

The dashed curve represents the spectrum of the CEL composite in the figure. CEL does not have these groups, so its spectrum contains a different set of bands. These bands include one at 2891 cm$^{-1}$ that can be assigned to aliphatic sp$^3$ stretch, a set of pronounced bands centered at 1017 cm$^{-1}$ (owing to C—O stretch at the C-3 position), and finally a band resulting from ether bonding at 894 cm$^{-1}$.[5-11] Represented as the dashed spectrum in FIG. 18, SECs display prominent bands at 1705 cm$^{-1}$ and 1654 cm$^{-1}$. These are the result of carbonyl stretching frequency. The aromatic C—H deformation that is out of plane with its phenolic group is visible in bands at 1589 cm$^{-1}$ and 1511 cm$^{-1}$.[22, 24] The band at 1134 cm$^{-1}$ is due to C—O stretching of its phenol group.

Figure 18:
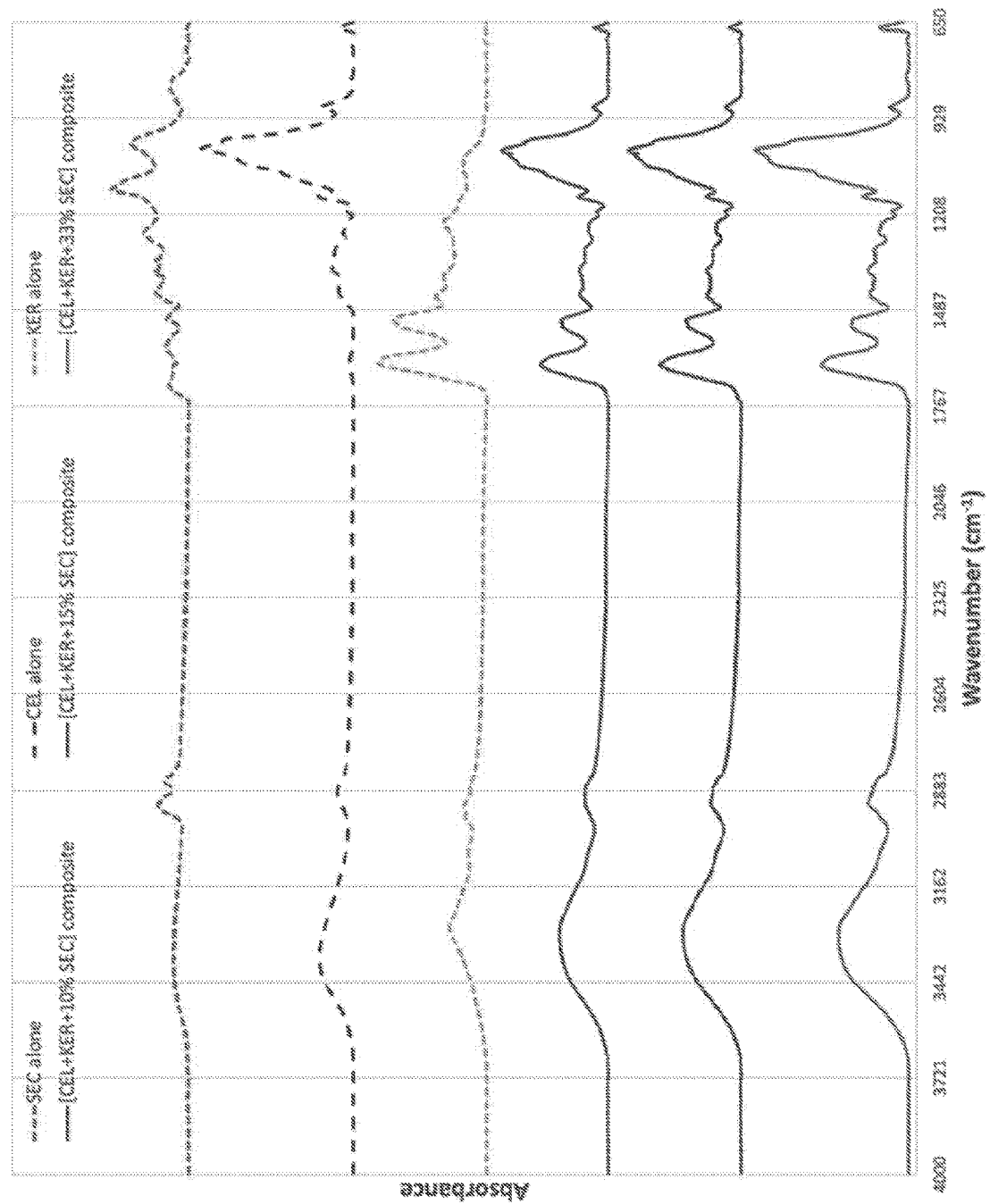
FIG. 18. FTIR spectra of SEC (dashed-line), CEL composite (dashed-line), wool (dashed-line), SEC (dashed-line, [CEL+KER+10% SEC] composite (solid line), [CEL+KER+15% SEC] composite (solid line), [CEL+KER+33% SEC] composite (solid line).

FIG. 18 also shows FTIR spectra of [CEL+KER+SEC] composites with different concentrations of SECs, i.e., [CEL+KER+10% SEC] composite (grey curve), [CEL+KER+15% SEC] composite and [CEL+KER+33% SEC] composite (brown curve). As expected, the spectra of the [CEL+KER+SEC] composites exhibit bands characteristic of their respective components, namely these bands tend to vary in relative intensity in tandem with the variation in the compositions of the composites. For example, all composites exhibit the band at around 1015 cm$^{-1}$ which is due to the sugar ring deformations of CEL together with the amide I and amide II bands of KER at 1643 cm$^{-1}$ and 1515 cm$^{-1}$, respectively. Additionally, the 1134 cm$^{-1}$ band which is due to C—O stretching of phenol groups of SEC increased in relative intensity as the relative amount of SEC increased in the [CEL+KER+SEC] composites from 10% SEC (gray curve) to 15% SEC and 33% SEC. Similarly, the relatively smaller band at 1703 cm$^{-1}$ in SEC due to its carbonyl stretching frequency can be seen as a shoulder on the spectrum of [CEL+KER+SEC] composite with highest concentration of SEC, i.e., 33% SEC (brown solid spectrum).

Tensile Strength. Since SECs are empty microcapsules, it is possible that adding SECs into [CEL+KER] composite may alter the mechanical properties of the composite. To test the effects of adding SECs to [CEL+KER] in relation to composite tensile strength, tensile strength measurements of [CEL+KER] composites with different concentration of SECs were made. Results obtained were presented in FIG. 21 where tensile strength was plotted as a function of SEC concentration in the [CEL+KER] composites. Within the margin of experimental error it was found that adding SECs to [CEL+KER] composites did not have any significant effect on tensile strength or on the mechanical properties of the composites.

Figure 22A:
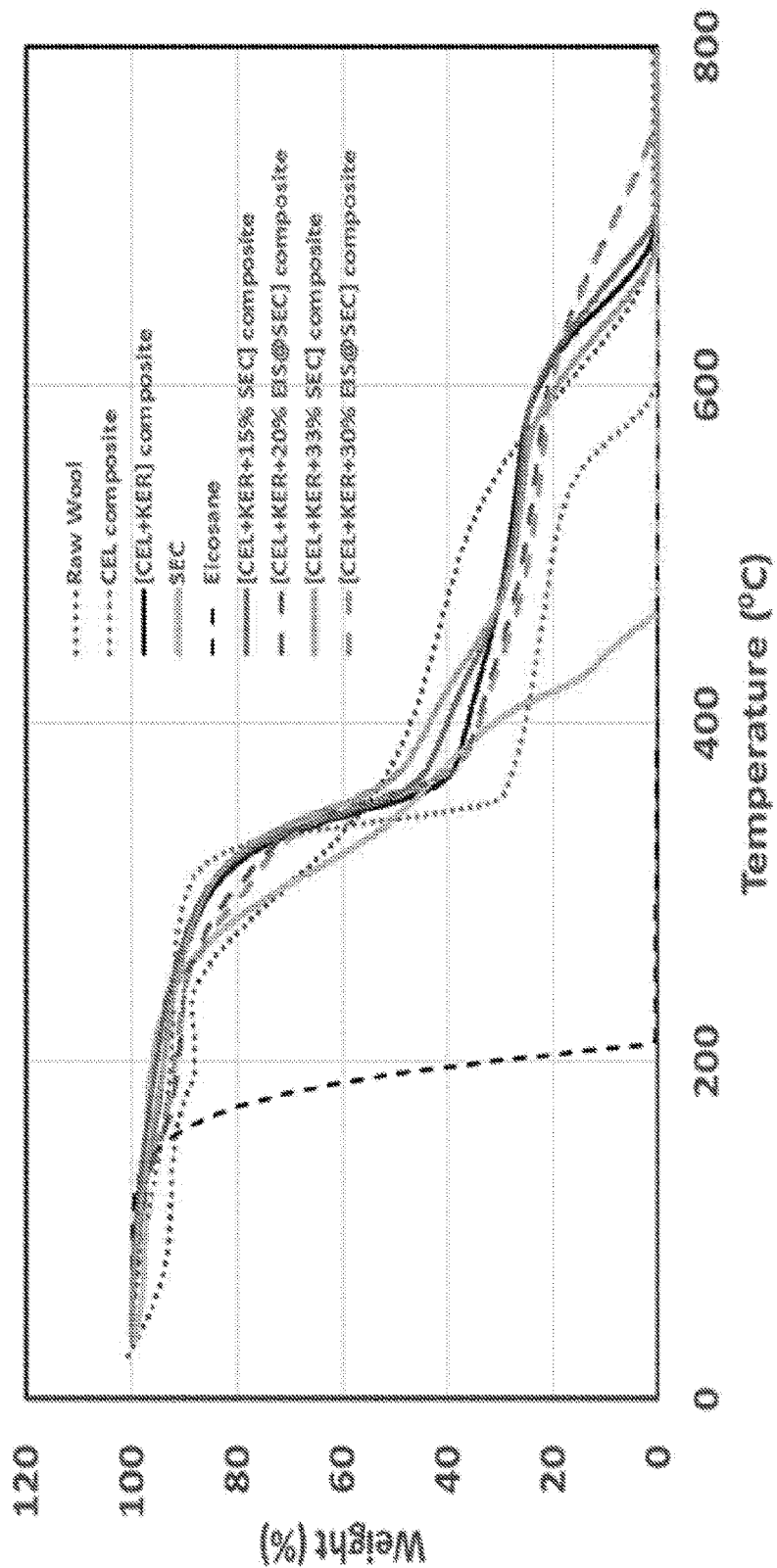
FIG. 22. Thermal gravimetric analysis curves plotted as (A) weight loss % and (B) derivatives of weight loss % of raw wool (dotted line), CEL composite (dotted line), SEC (solid line), EIS (dashed black line), [CEL+KER] composite (solid black line), [CEL+KER+15% SEC] composite (solid line), [CEL+KER+20% EIS@SEC] composite (dashed line), [CEL+KER+33% SEC] composite (solid line) and [CEL+KER+30% EIS@SEC] composite (dashed line).
Figure 22B:
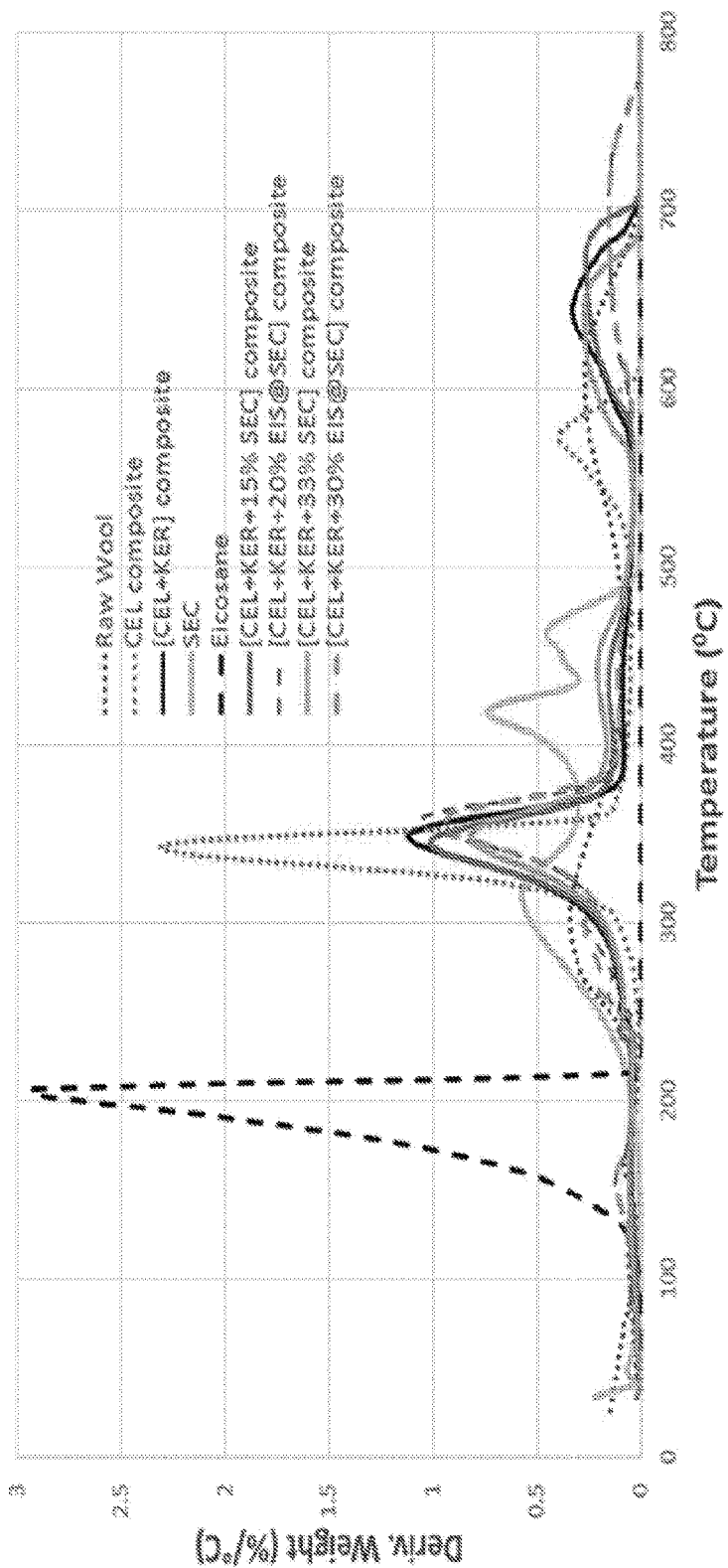

Thermal Gravimetric Analysis (TGA). It is possible that encapsulating SECs into [CEL+KER] composites may alter their thermal physical property. This possibility was investigated by thermal gravimetric analysis. Shown in FIG. 22 are the TGA plots as (A) weight loss % and (B) derivatives of weight loss % of SEC alone (solid curve), raw wool (dotted curve), CEL composite (dotted curve), [CEL+KER] composites (solid black curve), [CEL+KER+15% SEC] composite (solid curve), [CEL+KER+20% EIS@SEC] composite (dashed curve), [CEL+KER+33% SEC] composite (solid curve) and [CEL+KER+30% EIS@SEC] composite (dashed curve). SEC (solid curve) exhibited four phases of mass loss. The pattern matches up with what has been previously observed for SECs.[21, 22, 24, 28, 37] It can be credited to the loss of physically absorbed water in the first phase at temperatures ranging between ~50-150° C. The second mass loss occurs in the temperature range of ~220-350° C. and is likely due to the partial decomposition of SEC wall material combined with a loss of some gases such as oxygen.[29, 37] Decomposition in phase three, where the temperature range is ~362-434° C., continues and in phase four a decomposition of the solid residual is observed in the range of 434-490° C.[21, 22, 24, 28, 37] The TGA curve of raw wool (dotted curve) matches what was previously observed and seems to indicate that raw wool and SEC have relatively similar thermal stability, and, similar to that reported in our previous study, are comparatively less stable than CEL. TGA curves of CEL composite with only CEL (dotted curve) is similar to that observed previously.[5-11] Careful inspection reveals that the TGA curves of all three composites each with 50% CEL+50% KER and with different amounts of either SEC alone or [EIS@SEC], namely, [CEL+KER+15% SEC] (solid curve), [CEL+KER+20% EIS@SEC] (dashed curve), [CEL+KER+33% SEC] (solid curve), and [CEL+KER+30% EIS@SEC] (dashed curve) are similar more to that of CEL composite than to raw wool, namely, they all display three phases of mass loss. First, there is a small loss of weight observed in the temperature range of 80-140° C., which is due to the composite releasing moisture. Next, a two-step thermal degradation process with elevating temperatures was observed in all three composites. The first significant weight loss occurrence was found in the range 300-360° C. range owing to the onset of cellulose decomposition. The second weight loss peak caused by the oxidation and burning of cellulose was seen in the range of 400-550° C. Taken altogether, the results indicate that despite being less thermally stable thermally than CEL, when KER and SEC are added to CEL composites—even at a KER concentration of 50% and a SEC concentration as high as 33%—the TGA curves of the [50% CEL+50% KER+SEC] composites are comparable to composites that only have CEL. That is, adding KER and SECs to CEL composites does not seem to affect the thermal stability of the composite. It is of particular interest to observe that encapsulating EIS into SEC seems to improve the thermal stability of the [CEL+KER+SEC] composites, that is while [CEL+KER+SEC] composites fully degraded at ~700° C., [CEL+KER+30% EIS@SEC] composites fully degraded only at ~775° C. We are currently investigating thermal improvement effect of EIS.

Figure 19:
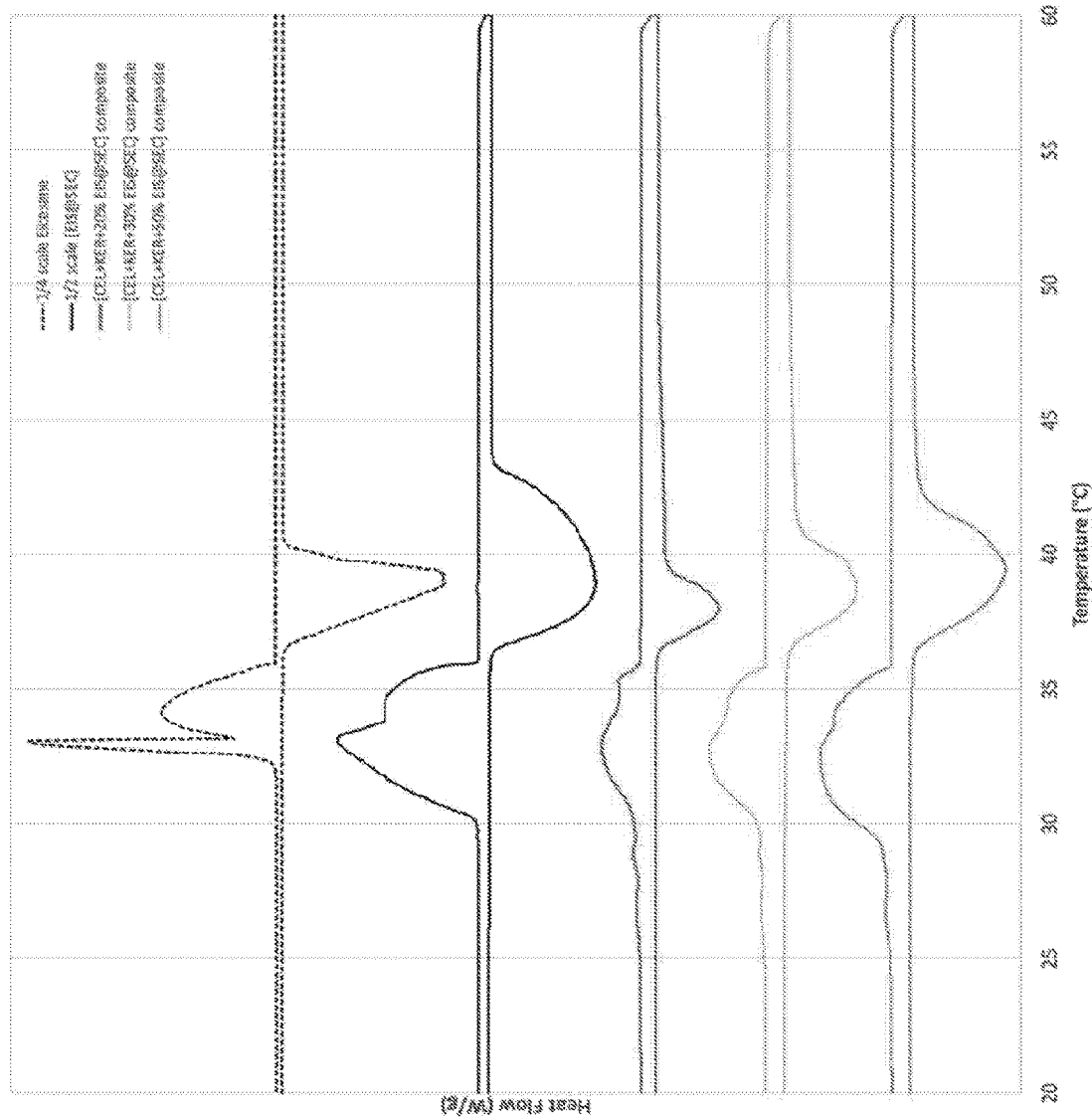
FIG. 19. Differential scanning calorimetry (DSC) curves of SEC curves of EIS (black dashed-line), [EIS@SEC] (black solid line), wool (dotted line), [CEL+KER+20% EIS@SEC] composite (solid line), [CEL+KER+30% EIS@SEC] composite (solid line), [CEL+KER+40% EIS@SEC] composite (solid line) and [CEL+KER+50% EIS@SEC] composite (solid line). The [CEL+KER+EIS@SEC] composites were prepared with [EIS@SEC] encapsulated with 3 g of EIS/1 g of SEC.
Figure 20:
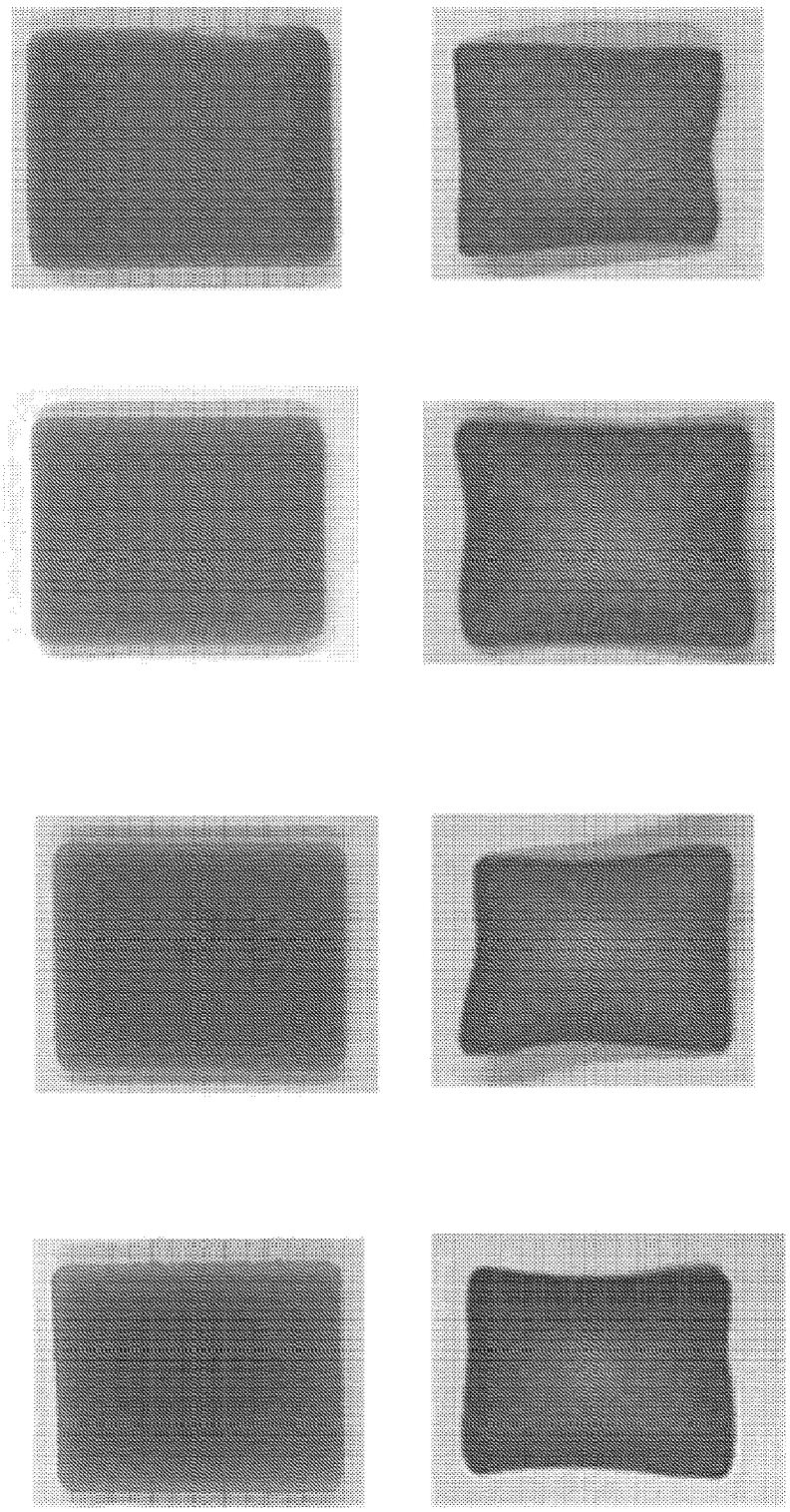
FIG. 20. Photographs of [CEL+KER+EIS@SEC] composites with different contents of [EIS@SEC]. The photos on the top row are of the Wet Composite Films while those on the bottom row are of the corresponding Dry Composite Films.

Differential Scanning calorimetry (DSC): The n-eicosane (EIS) used in this work was thoroughly recrystallized from methanol and its purity was verified by GC-MS as it was reported that its phase change transition is very sensitive to impurity.[38,39] Shown as black dashed-line in FIG. 19 is the DSC curve of EIS alone. As illustrated, EIS exhibited two exothermic bands during its crystallization process: a narrow band at 33.1° C. and a relatively broader band at 34.0° C. (see Table 2). n-alkanes including EIS are known to exhibit this type of bimodal transition during the crystallization process.[38-49] It has been suggested that it is due to the presence of the rotator phase above the bulk crystallization temperature. Consequently, EIS undertakes two phase transitions between the isotropic liquid and stable orthorhombic phases.

TABLE 2

Phase Change Properties of EIS, EIS encapsulated in SECs ([EIS @ SEC]) and [CEL + KER + EIS @ SEC] Composites with Different Contents of [EIS @ SEC] loading.

| Compound | | $T_c$ (° C.) | $\Delta H_c$ (J/g) | $T_m$ (° C.) | $\Delta H_m$ (J/g) |
|---|---|---|---|---|---|
| Eicosane | | 33.1, 34.0 | 252 | 38.9 | 255.8 |
| EIS @ SEC | Low EIS Loading | (32.5 ± 0.1), (34.3 ± 0.1) | 157.8 ± 0.9 | 38.6 ± 0.1 | 158 ± 1 |
| | High EIS Loading | (33.23 ± 0.03), (34.7 ± 0.1) | 193.0 ± 0.7 | 38.7 ± 0.2 | 193.7 ± 0.8 |
| [CEL + KER + 20% EIS @ SEC] composite | Low EIS Loading | 32.9 ± 0.2 | 32.2 ± 0.2 | 37.9 ± 0.1 | 32.4 ± 0.5 |
| | High EIS Loading | 32.5 ± 0.1 | 32.0 ± 0.2 | 38.21 ± 0.02 | 32.6 ± 0.4 |
| [CEL + KER + 30% EIS @ SEC] composite | Low EIS Loading | 32.8 ± 0.1 | 41.6 ± 0.2 | 38.4 ± 0.1 | 41.9 ± 0.4 |
| | High EIS Loading | 32.5 ± 0.4 | 45.9 ± 0.7 | 38.85 ± 0.07 | 47.5 ± 0.7 |
| [CEL + KER + 40% EIS @ SEC] composite | Low EIS Loading | 32.9 ± 0.1 | 50.4 ± 0.3 | 38.6 ± 0.1 | 50.9 ± 0.3 |
| | High EIS Loading | 32.4 ± 0.2 | 63.3 ± 0.2 | 39.48 ± 0.02 | 63.4 ± 0.2 |
| [CEL + KER + 50% EIS @ SEC] composite | Low EIS Loading | 32.4 ± 0.1 | 60.7 ± 0.2 | 39.0 ± 0.1 | 60.9 ± 0.2 |
| | High EIS Loading | 32.2 ± 0.2 | 69.2 ± 0.4 | 39.54 ± 0.04 | 68 ± 1 |

The first transition is from the homogeneously nucleated liquid to the rotator phase. The second transition is from the heterogeneously nucleated rotator phase to the crystalline phase.

There are two possible explanations for this unusual behavior. It could be a result of the methyl-end with low surface energy for the long chain geometry form of the n-alkanes, or it could be due to surface freezing that is entropically stabilized by fluctuations along the axis of the molecules.[38-49] Conversely, EIS exhibited only a single endothermic band at 38.9° C. during the melting process. This is as expected as it was also reported by other studies.[38-49] The enthalpies of fusion and crystallization transitions can be determined from the DSC curves, and the results are listed in Table 1. EIS released 252.0 J/g during the crystallization process and absorbed 255.8 J/g in the melting process. These results clearly indicate that EIS is well suited for use as phase change material for latent-heat storage-release.

We generated DSC curves for [EIS@SEC] when a ratio of 2 g of EIS/1 g of SEC (i.e., low EIS loading) was used in the encapsulation experiments (data not shown). Similar to EIS alone, when encapsulated in SEC, EIS exhibited two exothermic bands: a relatively sharper band at (32.5±0.1) ° C. and a broad band at around (34.3±0.1) ° C. in the crystallization process and a single band in the melting process. While the actual temperatures of [EIS@SEC] for crystallization and for heating are similar to those of EIS alone, the two crystallization bands and the melting band are relatively broader than the corresponding bands for EIS alone. Additionally, crystallization enthalpy ($\Delta H_c$) and melting enthalpy ($\Delta H_m$) values for [EIS@SEC] were observed to be (157.8±0.9) J/g and (158±1) J/g, which are comparatively lower than those for pure EIS. Given the enthalpy values for EIS and [EIS@SEC], roughly 62% of the EIS is estimated to be encapsulated the SEC cavity assuming that the SEC shell does not impede EIS heat absorption or release. This assumption may be invalid, though, as it has been reported that heat transfer to and from the core is reduced when a PCM is encapsulated into a microencapsulator.[38-49] This may be producing an effect in this case as well since [EIS@SEC] DSC bands are much more broad than when compared to the narrower bands of EIS alone. The actual amount of EIS being retained by the SEC could be greater than 62%.

To increase the amount of EIS encapsulated in SEC, a higher ratio of EIS/SEC was used as well as the mixing and heating under vacuum cycle being repeated several times. Specifically, it was found that by preparing an initial ratio of 3 g of EIS/1 g of SEC mixed and heated under vacuum, followed by adding an additional 1.5 g EIS/1 g of SEC, followed by adding an additional 1 g EIS/1 g of SEC, that a significantly higher amount of EIS was successfully encapsulated into the cavity of SEC. The results that were obtained are listed in Table 1 under the "High EIS Loading" label. They show that up to 77% of EIS was successfully encapsulated using this procedure. Further increase in the ratio of EIS/SEC used in the encapsulation did not lead to higher amounts of encapsulated EIS. The DSC curve for [EIS@SEC] with high EIS loading is shown in FIG. 19. As expected, similar to EIS alone and [EIS@SEC] with low loading, EIS again exhibits bimodal exothermic bands in the crystallization process, and a single endothermic band in the melting process. Furthermore, the fact that the $T_c$ and $T_m$ values for [EIS@SEC] with high EIS loading is the same, within experimental error, to those with low EIS loading clearly indicates that all EIS molecules were successfully encapsulated into the cavity of the SECs. The enthalpies of fusion and crystallization transition were expectedly found to have been increased to (193.0±0.7) J/g and (193.8±0.8) J/g which correspond to at least 77% in encapsulated EIS. It is pleasing to see that the enthalpies for fusion and crystallization for [EIS@SEC] with high EIS loading are about 1.2× higher than the corresponding values found for [EIS@SEC] with low EIS loading.

It is noteworthy to add that EIS is not the only phase change material that can be encapsulated into the cavity of SECs. It was selected for this study because it has a melting point of 38° C. which is the same as body temperature. Not only that other PCMs can also be encapsulated into SECs but a mixture of two different phase change compounds can be simultaneously encapsulated as well. In fact, as shown in Table 3, we found that either n-octadecane (C18) which has a melting point of (28° C.-30° C.) or n-decosane (C22, mp=42° C.-45° C.) can also be encapsulated into SEC cavity, and that both [C18@SEC] and [C22@SEC] compounds obtained fully retain phase change properties of C18 and C22, respectively. More significance is the fact that both C18 and C22 can be simultaneously encapsulated into the cavity of SECs, and that the $T_c$ and $T_m$ of the [(C18+C22)@SEC] obtained can be selected by judiciously adjusting relative concentrations of C18 and C22. For example, when a mixture of 6:4 w/w [C22:C18] was encapsulated into SECs, the [(C18+C22@SEC] compound not only fully retains phase change property of (6:4 C22:C18) but that its $T_c$ and $T_m$ values were expectedly found to be at (34.9±0.2) ° C. and (35.8±0.1) ° C., respectively.

TABLE 3

Phase Change Properties of n-Octadecane (C18), n-Docosane (C22), 6:4 (w/w) mixture of C22:C18 (C22:C18), and (C22:C18) @ SEC.

| Compound | $T_c$ (° C.) | $\Delta H_c$ (J/g) | $T_m$ (° C.) | $\Delta H_m$ (J/g) |
|---|---|---|---|---|
| n-Octadecane (C18) | 24.3 | 244.6 | 30.4 | 245.6 |
| n-Docosane (C22) | 40.5; 42.0 | 259.5 | 46.3 | 259.4 |
| 6:4 (w/w) mixture of C22:C18 | 34.9 ± 0.2 | 164 ± 2 | 35.8 ± 0.1 | 142 ± 1 |
| (C22:C18) @ SEC | 36.3 | 125.4 | 34.1 | 121.0 |

[CEL+KER] composites with different [EIS@SEC] concentrations of both low and high EIS loadings were prepared (data not shown and FIG. 19). As expected, the DSC bands of all composites with both low and high EIS loadings increased relative to the [EIS@SEC] concentration in the composites. Composites with low EIS loading, for example, had exothermic and endothermic bands of [CEL+KER+20% EIS@SEC] that increased when [EIS@SEC] concentration in the composite increased to 30%. In fact, it continued to increase as concentration levels reached 40% and 50%. The bimodal transition band in the crystallization phase coalesced into a single broad band for all composites. This was also observed previously by other groups for other encapsulators.[38-49] This effect may be due to the crystallization of EIS being hindered by the SEC microcapsule and the [CEL+KER] polymeric matrix which, in effect, coalesces the homogeneous nucleated liquid to the rotator phase and heterogeneous nucleated rotator phase into a single and broad exothermic crystallization band. Similar to EIS alone and [EIS@SEC], the [CEL+KER+EIS@SEC] composites also exhibit a single but relatively broader endothermic band for the melting transition. It is pleasing to observe that the $T_c$ and $T_m$ values of [CEL+KER+EIS@SEC] composites with different concentrations of both low and high EIS loading [EIS@SEC] are the same, within experimental error, to those of EIS alone and [EIS@SEC].

Taken together, the DSC results clearly show that the EIS fully retains its phase change property when it was encapsulated into SECs, and subsequently when [EIS@SEC] was incorporated into the [CEL+KER] composites. EIS releases energy when it undergoes crystallization upon cooling and absorbs energy to melt when heated, regardless of whether it is alone, encapsulated into SECs in either low loading or high loading, or when the resulting [EIS@SEC] is then incorporated into [CEL+KER] composites. In addition to the $T_c$ and $T_m$ values, enthalpies of fusion and crystallization transition ($\Delta H_m$ and $\Delta H_c$) values were obtained from the DSC curves and are listed in Table 1. For composites with low EIS loading, the $\Delta H_c$ value of [CEL+KER+20% EIS@SEC] composite was found to be (32.2±0.2) J/g. This value increased by 29% to (41.6±0.2) J/g when [EIS@SEC] concentration was increased to 30%. It continued its increase to 40% and then 50%, where 21% and 20% increases to (50.4±0.3) J/g and (60.7±0.2) J/g, respectively, were observed. The melting enthalpy, $\Delta H_m$, similarly correlated with [EIS@SEC] concentration in the composites. [CEL+KER] composites with [EIS@SEC] concentrations of 20%, 30%, 40% and 50% resulted in increased $\Delta H_m$ values, from (32.4±0.5) J/g to (41.9±0.4) J/g, (50.9±0.3) J/g, and (60.9±0.2) J/g, respectively.

As expected, $\Delta H_c$ and $\Delta H_m$ values of [CEL+KER+EIS@SEC] composites with higher loading of EIS also increase concomitantly with the higher loading of EIS in [EIS@SEC], and with the concentration of [EIS@SEC] in the composites. That is, $\Delta H_c$ values for composites with 20%, 30%, 40%, and 50% of [EIS@SEC] were found to be (32.0±0.2) J/g, (45.9±0.7) J/g, (63.3±0.2) J/g, and (69.2±0.4) J/g, respectively. Corresponding $\Delta H_m$ values also increased from (32.6±0.4) J/g to (47.5±0.7) J/g, (63.4±0.2) J/g, and (68±1) J/g, respectively.

From $\Delta H_c$ and $\Delta H_m$ values of [EIS@SEC] and [CEL+KER+EIS@SEC] composites with high EIS loading, actual amount of [EIS@SEC] incorporated into the composites can be calculated. It was found that up to 84% of [EIS@SEC] was successfully incorporated into the [CEL+KER] composite when 20% (w/w) of [EIS@SEC] per [CEL+KER] was used in the synthesis. When 30%, 40%, and 50% w/w of [EIS@SEC] were used, the quantity of successful incorporation of [EIS@SEC] decreases to 79%, 82% and 72%, respectively. While the incorporating efficiency for [CEL+KER+50% EIS@SEC] composite is relatively lower than that for the [CEL+KER+20% EIS@SEC] composite, it is noteworthy to add that the incorporation efficiency decreased by only 8% when the amount of [EIS@SEC] used for the incorporation experiment into the [CEL+KER] composite was increased by 2.5 fold. The efficiency of latent heat storage and release of the [CEL+KER+EIS@SEC] composites was estimated to be around 80%. It is significant that the DSC curves of the [CEL+KER+EIS@SEC] composites stayed the same, even after 200 heating-melting cycles. This makes it clear the SEC successfully retained the EIS in its cavity and prevented it from leaking out. The [CEL+KER+EIS@SEC] composites have proven to be very stable and reliable even through phase changes, which makes them excellent candidates for phase change material applications.

Based on the latent heat release and storage of the amount of EIS successfully encapsulated in the composite and that for EIS alone, the efficiency of latent heat release and storage for the [CEL+KER+EIS@SEC] composites with low EIS loading and high EIS loading were estimated to be about 80% and 50%, respectively.

As also reported by other groups for PCM encapsulated in other microencapsulators, the relatively lower efficiencies of the composites compared to that of pure EIS may be due to the fact that the encapsulation into the cavity of the SEC leads to increasing the interaction among encapsulated EIS molecules as well as between EIS molecules and the supporting materials, i.e., CEL, KER, and SEC. This, in effect, hinders EIS from crystallizing and melting. Furthermore, as evident from the DSC curves, the CEL, KER, and SEC do not perform any phase changes. Only the EIS in the SEC cavity stores and releases latent heat through phase changes. The combination of these factors leads to relatively lower efficiency for the composites compared to that of pure EIS. The fact that the efficiency of latent heat release and storage for [CEL+KER+EIS@SEC] composites with high EIS is relatively lower compared to those with low EIS loading also lends credence to this explanation. Specifically, higher concentration of encapsulated EIS leads to higher interactions among EIS molecules as well as between EIS molecules and the supporting materials, i.e., CEL, KER, and SEC. This in effect hinders EIS from crystallizing, which reduces the enthalpy of the [CEL+KER+EIS@SEC] composites with high EIS loading. We are currently carrying out additional experiments to gain insight into role of SEC on phase change property of encapsulated EIS.

Effectiveness of SEC as a Microencapsulator, and Stability and Reliability of [CEL+KER+EIS@SEC] composites as Phase Change Materials. To investigate if SEC fully retain EIS in their cavities after being used repeatedly as well as to assess [CEL+KER+EIS@SEC] stability and reliability as composites for use as a phase change materials, we put the

[CEL+KER+50% EIS@SEC] composites through 200 heating-cooling cycles (data not shown). After 200 cycles over the span of three days, the melting and crystallization temperatures as well as the enthalpy values for heat absorption and release remained the same. Moreover, the difference between the first and last DSC scans, (cycle 1) and (cycle 200), respectively, was essentially the same as their corresponding enthalpies for crystallization and melting differences ($\Delta\Delta H_c$ and $\Delta\Delta H_m$), which are just 0.40% and 0.17%, respectively. This demonstrates that SEC fully and effectively retain EIS in its cavity and protects it during phase change transitions. We can conclude that [CEL+KER+EIS@SEC] composites are reliable, very stable, and possess highly reproducible phase change properties.

Conclusion

Sporopollenin exine capsules (SECs) are empty microcapsules derived from natural pollen grains that have had all external and internal cytoplastic materials chemically removed. We have shown that a variety of phase change materials (PCMs) can be encapsulated into the hollow microcavities of SECs either individually or simultaneously. For examples, natural PCMs based on natural paraffin wax such as n-octadecane (C18, mp=28-30° C.), n-eicosane (C20, EIS, mp=34-37° C.) or n-docoane (C22, mp=42-45° C.) was successfully encapsulated into SEC cavity either individually or as a mixture with an encapsulation efficiency of at least 80% w/w. The [C18@SEC], [EIS@SEC], [C22@SEC] and [6:4 w/w (C18:C22)@SEC] compounds obtained fully retain phase change properties of the corresponding individual or their mixture. For example, $T_c$ and $T_m$ values of [EIS@SEC] compound and were found to be (32.5±0.1) ° C. and (38.6±0.1) ° C., whereas for [(6:4 C18:C22)@SEC] compound they were (34.9±0.2) ° C. and (35.8±0.1) ° C. The stable and robust nature of SECs are what keeps PCM in their cavities and protects them from high temperatures and caustic environments. Consequently, [EIS@SEC] composites can be successfully integrated into [CEL+KER] composites by way of a synthetic process where CEL and KER are dissolved in a heated ionic liquid solution of [BMIM$^+$Cl$^-$] at 120° C. to produce [CEL+KER+EIS@SEC] composites. Of note is how SECs protect EIS and keep it from leaking out of the microcavities during phase change transition, which allows EIS to fully retain their phase change properties. Similar to EIS on its own, EIS in [CEL+KER+EIS@SEC] crystallizes when cooled and melts when heated. The energies associated with these phase changes allow the [CEL+KER+EIS@SEC] composites to act in the manner expected of phase change materials: they release heat to the environment when cooled and absorb energy when warmed. Latent heat storage and release efficiency of the [CEL+KER+EIS@SEC] composites was assessed as roughly 80%. More significantly, after 200 melting-heating cycles, the DSC curves of the [CEL+KER+EIS@SEC] composites was the same. That is, the difference between the first and last DSC scans were virtually identical as their corresponding enthalpies for crystallization and melting differences ($\Delta\Delta H_c$ and $\Delta\Delta H_m$), which were 0.40% and 0.17%, respectively. This strongly indicates that EIS was effectively retained in the SEC cavity and protected from loss by leaking. The [CEL+KER+EIS@SEC] composites have thus proven to highly stable and reliable as phase change materials.

The composites we developed are superior than others that are currently available because they are more robust, have strong mechanical properties, are biocompatible and possess antibacterial activity.[5-11] The composites are also sustainable because we can synthesize them using a green, recyclable process and all-natural materials, such as CEL, wool, natural pollen grains and wax, which are found abundantly in nature. More importantly, individual PCMs such as EIS and mixtures of different PCMs such as 6:4 (C22:C18) can be encapsulated into SECs. We have established that the performance characteristics of these composites are reproducible and better than other available PCMs, which tend to work in limited temperature ranges and may have complications associated with decomposition and/or leakage during phase change transitions. The ability to overcome these shortfalls makes the [CEL+KER+PCM@SEC] composites uniquely suited for use smart textiles, smart building materials and energy storage. Delving further into these possibilities are the focus of our intense investigation.

REFERENCES

References for Example 1

1. McLoughlin, J.; Sabir, T. Ed., High-performance Apparel: Materials, Development, and Applications, Elsevier and Woodhead Publishing, Duxford, UK 2018
2. Hou, X. Ed., Design, Fabrication, Properties, and Applications of Smart and Advanced Materials, CRC Press, Taylor & Francis Group, Boca Raton, 2016
3. Haghi, A. K.; Zaikov, G. E., Ed., Handbook of Research on Nanomaterials, Nanochemistry and Smart Materials, Nova Biomedical Publishers, New York, 2013.
4. Dias, T., Ed., Electronic textiles: Smart Fabrics and Wearable Technology, Woodhead Publishing, Cambridge, UK, 2015
5. Tran, C. D.; Duni, S.; Harkins, A. L, Recyclable Synthesis, Characterization and Antimicrobial Activity of Chitosan-based Polysaccharide Composite Materials, *J. Biomed. Mat. Res. A*, 2013, 101, 2248-2257.
6. Tran, C. D.; Duni, S.; Delneri, A.; Franko, M., Chitosan-Cellulose Composite Materials Preparation, Characterization and Application for Removal of Microcystin, *J. Hazard. Mater.* 2013, 252-253, 355-366
7. Mututuvari, T. M.; Tran, C. D., Synergistic Adsorption of Heavy Metal Ions and Organic Pollutants by Polysaccharide Supramolecular Composite Materials from Cellulose, Chitosan and Crown Ether, *J. Hazard. Mater.*, 2014, 264, 449-459.
8. Harkins, A. L.; Duni, S.; Kloth, L. C.; Tran, C. D., Chitosan-Cellulose Composite for Wound Dressing Material. Part 2. Antimicrobial Activity, Blood Absorption Ability and Biocompatibility, *J. Biomed. Mat. Res. B*, 2014, 102, 1199-1206.
9. Tran, C. D.; Mututuvari, T., Cellulose, Chitosan and Keratin Composite Materials. Controlled Drug Release, *Langmuir*, 2015, 31, 1516-1526.
10. Tran, C. D.; Mututuvari, T., Cellulose, Chitosan and Keratin Composite Materials. Facile and Recyclable Synthesis, Conformation and Properties, *ACS Sus. Chem. Eng.*, 2016, 4, 1850-1861.
11. Tran, C. D.; Prosenc, F.; Franko, M.; Benzi, G., Green Composites from Cellulose, Wool, Hair and Chicken Feather. Synthesis, Structure and Antimicrobial Property, *Carb. Pol.*, 2016, 151, 1260-1276.
12. Peng, H.; Zhang, D.; Ling, X.; Li, Y.; Wang, Y; Yu, Q.; She, X.; Li, Y.; Ding, Y, n-Alkanes Phase Change Materials and Their Microencapsulation for Thermal Energy Storage: A Critical Review, *Energy Fuels,* 2018, 32, 7262-7293.
13. Zhao, C. Y; Zhang, G. H., Review on microencapsulated Phase Change Materials: Fabrication, Characterization and Applications, *Renewable Sus. Energ. Rev.,* 2011, 15, 3813-3832.
14. Raoux, S.; Wuttig, M., Phase Change Materials. Science and Applications, Springer, 2009.
15. Cabeza, L. F.; Nguan H. S. T, High-temperature Thermal Storage Systems Using Phase Change Materials, Academic Press, 2018.
16. Barrier, S.; Diego-Taboada, A.; Thomasson, M. J.; Madden, L.; Pointon, J. C.; Wadhawan, J. D.; Mackenzie, G., Viability of Plant Spore Exine Capsules for Microencapsulation, *J. Mater. Chem.,* 2011, 21, 975-981.
17. Mundargi, R. C.; Potroz, M. G.; Park, S.; Lee, J. H.; Seo, J.; Cho, N. J., Lycopodium Spores: A Naturally Manufactured, Superrobust Biomaterial for Drug Delivery, *Adv. Funct. Mater,* 2016, 26, 487-497.
18. Li, F. S.; Phyo, P.; Jocobowitz, J.; Hong, M.; Weng, J. K., The Molecular Structure of Plant Sporopollenin, *Nature Plants,* 2019, 5, 41-46.
19. Soni, M. L.; Gupta, M.; Namdeo, K. P., Isolation of Sporopollenin-like Polymer from *Aspergillus Niger* and its Characterization, *Chemical Papers,* 2016, 70, 1556-1567.
20. Gonzalez-Cruz, P.; Uddin, J. J.; Tawe, S. U.; Abidi, N.; Gill, H. S., Chemical Treatment Method for Obtaining Clean and Intact Pllen Shells of Different Species, *ACS Biomat. Sci. Eng.,* 2018, 4, 2319-2329.
21. Udin, J. J.; Liyanage, S.; Abidi, N.; Gill, H. S., Physical and Biochemical Characterization of Chemically Treated Pollen Shells for Potential Use in Oral Delivery of Therapeutics, *J. Pharmaceu. Sci.,* 2018, 107, 1-13.
22. Chiappe, C.; Mezzetta, A.; Pomelli, C. S.; Puccini, M.; Seggiani, M., Product as Reaction Aolvent: An Unconventional Approach for Ionic Liquid Synthesis. *Org. Proc. Res. Dev.,* 2016, 20, 2080-2084.
23. Barrier, S.; Diego-Taboada, A.; Thomasson, M. J.; Madden, L.; Pointon, J. C.; Wadhawan, J. D.; Mackenzie, G., Viability of Plant Spore Exine Capsules for Microencapsulation. *J. Mater. Chem.,* 2011, 21(4), 975-981.
24. Diego-Taboada, A.; Maillet, L.; Banoub, J. H.; Lorch, M.; Rigby, A. S.; Boa, A. N.; Mackenzie, G., Protein Free Microcapsules Obtained from Plant Spores as a Model for Drug Delivery: Ibuprofen Encapsulation, Release and Taste Masking. *J. Mater. Chem. B,* 2013, 1(5), 707-713.
25. Mackenzie, G.; Beckett, S.; Atkin, S.; Diego-Taboada, A. 2014. Pollen and Spore Shells—Nature's Microcapsules. In Microencapsulation in the Food Industry (pp. 283-297). Academic Press.
26. Yilmaz, E.; Sezgin, M.; Yilmaz, M., Enantioselective Hydrolysis of Racemic Naproxen Methyl Ester with Sol-gel Encapsulated Lipase in the Presence of Sporopollenin, *J. Mol. Cat. B: Enzymatic,* 2010, 62, 162-168.
27. Jiang, F.; Wang, X.; Wu, D.; Design and Synthesis of Magnetic Microcapsules based on n-Eicosanecore and Fe3O4/SiO2 Hybrid Shell for Dual-Functional Phase Change Materials, *Appl. Ener.* 2014, 134, 456-468.
28. Li, F.; Wang, X.; Wu, D., Fabrication of Multifunctional Microcapsules containing n-Eicosane Core and Zinc Oxide Shell for Low-Temperature Energy Storage, Photocatalysis, and Antibiosis *Ener. Conversion Man.* 2015, 106, 873-88
29. Chiappe, C.; Demontis, G. C.; Bussolo, V. D.; Douton, M. J. R.; Rossella, F.; Pomelli, C. S.; Sartini, S.; Caporali, S., From Pollen Grains to Functionalized Microcapsultes: a Facile Chemical Route using Chiral Ionic Liquids, *Green Chem.* 2017, 19, 1028-1033.
30. Dyab, A. K. F.; Mohamed, M. A.; Meligi, N. M.; Mohamed, S. K., Encapsulation of Erythromycin and Bacitracin Antibiotics into Natural Aporopollenin Microcapsules: Antibacterial, Cytotoxicity, In Vitro and In Vivo Release Studies for Enhanced Bioavailability, *RSC Adv.* 2018, 8, 33432-3344.
31. Wang, S.; Yang, Y; Lu, A.; Zhang, L., Construction of Cellulose/ZnO Composite Microspheres in NaOH/zinc Nitrate Aqueous Solution Via One-Step Method, *Cellulose,* 2019, 26:557-568.
32. Jia, B.; Mei, Y; Cheng, L.; Zhou, J.; Zhang, L., Preparation of Copper Nanoparticles Coated Cellulose Films with Antibacterial Properties through One-Step Reduction, *ACS Appl. Mater. Interfaces* 2012, 4, 2897-2902.
33. Hideno, A., Comparison of the Thermal Degradation Properties of Crystalline and Amorphous Cellulose, as well as Treated Lignocellulosic Biomass, *Bioresources* 2016, 11, 6309-6319.
34. Zhang, X. X.; Fan, Y F.; Tao, X. M., Yick, K. L. Crystallization and Prevention of Supercooling of Microencapsulated n-Alkanes, *J. Col. Interf. Sci.* 2005, 281, 299-306.
35. Oliver, M. J.; Calvert, P. D. Homogeneous Nucleation of n-Alkanes measured by Differential Scanning calorimetry, *J. Crystal. Growth* 1975, 30, 343-351.
36. Su, Y; Liu, G.; Xie, B.; Fu, D.; Wang, D, Crystallization Features of Normal Alkanes in Confined Geometry, *Acct. Chem. Res.* 2014, 47, 192-201.
37. He, F.; Wang, X. D.; Wu, D. Z., Phase-Change Characteristics and Thermal Performance of Form-Stable n-alkanes/silica Composite Phase Change Materials Fabricated by Sodium Silicate Precursor. *Renew Energy* 2015, 74, 689-698.
38. Sirota, E. B.; King, H. E.; Singer, D. M.; Shao, H. H. Rotator Phases of the Normal Alkanes: An X-ray Scattering Study. *J. Phys. Chem.* 1993, 98, 5809-5824.
39. Zhang, X.; Wang, X.; Wu, D. Design and Synthesis of Multifunctional Microencapsulated Phase Change Materials with Silver/Silica Double-Layered Shell for Thermal Energy Storage, Electrical Conduction and Antimicrobial Effectiveness, *Energy* 2016, 111, 498-512.
40. Sirota, E. B.; King Jr. H. E.; Singer, D. M.; Shao, H. H. Rotator Phases of the Normal Alkanes: An X-ray Scattering Study, *J. Chem. Phys.* 1993, 98, 5809-5814.
41. Sirota, E. B.; Singer, D. M. Phase Transitions Among Rotator Phases of the Normal Alkanes, *J. Chem. Phys.* 1993, 101, 10873-10882.
42. Li, F.; Wang, X.; Wu, D. Fabrication of Multifunctional Microcapsules Containing n-Eicosane Core and Zinc Oxide Shell for Low Temperature Energy Storage, Photocatalysis and Antibiosis, *Energ. Conv. Management* 2015, 106, 873-885.
43. Do, C. V; Nguyen, T. T. T.; Park, J. S. Phase Change Core/Shell Structured Nanofibers Based on Eicosane/Poly (vinylidene fluoride) for Thermal Storage Applications, *Korean J. Chem. Eng.* 2013, 30, 1403-1409.

REFERENCES FOR EXAMPLE 2

1. Raoux, S.; Wuttig, M., Phase Change Materials. Science and Applications, Springer, 2009.
2. Peng, H.; Zhang, D.; Ling, X.; Li, Y; Wang, Y.; Yu, Q.; She, X.; Li, Y; Ding, Y, n-Alkanes Phase Change Materials and Their Microencapsulation for Thermal Energy Storage: A Critical Review, *Energy Fuels,* 2018, 32, 7262-7293.
3. Zhao, C. Y; Zhang, G. H., Review on microencapsulated Phase Change Materials: Fabrication, Characterization and Applications, *Renewable Sus. Energ. Rev.,* 2011, 15, 3813-3832.
4. Cabeza, L. F.; Nguan H. S. T, High-temperature Thermal Storage Systems Using Phase Change Materials, Academic Press, 2018; pp 5-36 and 231-274.
5. Tran, C. D.; Mututuvari, T. Cellulose, Chitosan and Keratin Composite Materials. Facile and Recyclable Synthesis, Conformation and Properties. *ACS Sustainable Chem. Eng.,* 2016, 4, 1850-1861.
6. Iran, C. Mututuvari, T. Cellulose, Chitosan and Keratin Composite Materials. Controlled Drug Release. *Langmuir,* 2015, 31, 1516-1526.
7. Tran, C. D.; Prosenc, F.; Franko, M. Benzi, G. Green Composites from Cellulose, Wool, Hair and Chicken Feather. Synthesis, Structure and Antimicrobial Property. *Carb. Pol.,* 2016, 151, 1260-1276.
8. Tran, C. D.; Prosenc, F.; Franko, M. Facile Synthesis, Structure, Biocompatibility and Antimicrobial Property of Gold Nanoparticle Composites from Cellulose and Keratin. *J. Coll. Interf. Sci.* 2018, 510, 237-246.
9. Rosewald, M.; Hou, Mututuvari, T.; Harkins, A.; Tran, C. D. Cellulose-Chitosan-Keratin Composite Materials: Synthesis and Immunological and Antibacterial Properties *ECS Transactions,* 2014, 64, 499-505.
10. Tran, C. D.; Prosenc, F.; Franko, M.; Benzi, G. One-pot synthesis of biocompatible silver nanoparticle composites from cellulose and keratin: Characterization and antimicrobial activity. *ACS Appl. Mater. Interf.* 2016, 8, 34791-34801.
11. Tran, C. D; Makuvaza, J.; Munson, E.; Bennett, B. Biocompatible Copper Oxide Nanoparticle Composites from Cellulose and Chitosan: Facile Synthesis, Unique Structure and Antimicrobial Activity *ACS Appl. Mater. Interfaces* 2017, 9, 42503-42515.
12. Peng, H.; Zhang, D.; Ling, X.; Li, Y; Wang, Y; Yu, Q.; She, X.; Li, Y.; Ding, Y. n-Alkanes Phase Change Materials and Their Microencapsulation for Thermal Energy Storage: A Critical Review. *Energy Fuels* 2018, 32, 7262-7293.
13. Zhao, C. Y; Zhang, G. H. Review on microencapsulated phase change materials (MEPCMs): Fabrication, characterization and applications. *Renewable Sustainable Energy Rev.* 2011, 15, 3813-3832.
14. S. Raoux; M. Wuttig, *Phase Change Materials. Science and Applications,* Springer, New York, 2009; pp 17-36.
15. Han, L.; Jia, X.; Li, Z.; Yang, Z.; Wang, G.; Ning, G. Effective Encapsulation of Paraffin Wax in Carbon Nanotube Agglomerates for New Shape-Stabilized Phase Change Material with Enhanced Thermal Storage Capacity and Stability. *Ind. Eng. Chem. Res.* 2018, 57, 13026-13035
16. Konuklu, Y.; Paksoy, H. O.; Unal, M. Nanoencapsulation of n-alkanes with polystyrene-co-ethylacrylate) shells for thermal energy storage. *Appl. Energy* 2015, 150, 335-340.
17. Zhang, H.; Wang, X. Fabrication and performances of microencapsulated phase change materials based on n-octadecane core and resorcinol-modified melamine-formaldehyde shell. *Colloids Surf.,* A 2009, 332, 129-138.
18. Zhang, H.; Wang, X. Synthesis and properties of microencapsulated n-octadecane with polyurea shells containing different soft segments for heat energy storage and thermal regulation. *Sol. Energy Mater. Sol. Cells* 2009, 93, 1366-1376.
19. Sari, A.; Alkan, C.; Karaipekli, A. Preparation, characterization and thermal properties of PMMA/n-heptadecane microcapsules as novel solid-liquid microPCM for thermal energy storage. *Appl. Energy* 2010, 87, 1529-1534.
20. Fang, Y.; Liu, X.; Liang, X.; Liu, H.; Gao, X.; Zhang, Z. Ultrasonic synthesis and characterization of poly styrene/n-dotriacontane composite nanoencapsulated phase change material for thermal energy storage. *Appl. Energy* 2014, 132, 551-556.
21. Gonzalez-Cruz, P.; Uddin, J. J.; Tawe, S. U.; Abidi, N.; Gill, H. S., Chemical Treatment Method for Obtaining Clean and Intact Pllen Shells of Different Species, *ACS Biomat. Sci. Eng.,* 2018, 4, 2319-2329.
22. Udin, J. J.; Liyanage, S.; Abidi, N.; Gill, H. S., Physical and Biochemical Characterization of Chemically Treated Pollen Shells for Potential Use in Oral Delivery of Therapeutics, *J. Pharmaceu. Sci.,* 2018, 107, 1-13.
23. Barrier, S.; Diego-Taboada, A.; Thomasson, M. J.; Madden, L.; Pointon, J. C.; Wadhawan, J. D.; Mackenzie, G., Viability of Plant Spore Exine Capsules for Microencapsulation, *J. Mater. Chem.,* 2011, 21, 975-981.
24. Soni, M. L.; Gupta, M.; Namdeo, K. P., Isolation of Sporopollenin-like Polymer from *Aspergillus Niger* and its Characterization, *Chemical Papers,* 2016, 70, 1556-1567.
25. Mundargi, R. C.; Potroz, M. G.; Park, J. H.; Seo, J.; Tan, E. L; Lee, J. H.; Cho, N. J. Eco-friendly Streamlined Process for Sporopollenin Exine Capsule Extraction, *Sci. Rep.* 2016, 6, 19960-19973.
26. Corliss, M.; Bok, C. K; Gillissen, J; Potroz, M. G.'Jung, H.; Tan, E. L.; Mundargi, R, C; Cho, N. J. Preserving the Inflated Structure of Lyophilized Spooropollenin EWxine Capsules with Polyethylene Glycole Osmolyte, *J. Ind. Eng. Chem,* 2018, 61, 266-264.
27. Mundargi, R. C.; Potroz, M. G.; Park, S.; Lee, J. H.; Seo, J.; Cho, N. J., Lycopodium Spores: A Naturally Manufactured, Superrobust Biomaterial for Drug Delivery, *Adv. Funct. Mater.,* 2016, 26, 487-497.
28. Li, F. S.; Phyo, P.; Jocobowitz, J.; Hong, M.; Weng, J. K., The Molecular Structure of Plant Sporopollenin, *Nature Plants,* 2019, 5, 41-46.
29. Barrier, S.; Diego-Taboada, A.; Thomasson, M.; Madden, L.; Pointon, J.; Wadhawan, J.; Mackenzie, G. Viability of Plant Spore Exine Capsules for Microencapsulation. *J. Mater. Chem.,* 2011, 21, 975-981.
30. Diego-Taboada, A.; Maillet, L.; Banoub, J. H.; Lorch, M.; Rigby, A. S.; Boa, A. N.; Mackenzie, G., Protein Free Microcapsules Obtained from Plant Spores as a Model for Drug Delivery: Ibuprofen Encapsulation, Release and Taste Masking. *J. Mater. Chem. B,* 2013, 1(5), 707-713.
31. Mackenzie, G.; Beckett, S.; Atkin, S.; Diego-Taboada, A. 2014. Pollen and Spore Shells—Nature's Microcapsules. In Microencapsulation in the Food Industry; Academic Press: New York, 2014; pp 283-297.
32. Palazzo, 1.; Mezzetta, A.; Guazzelli, L.; Sartini, S.; Stefania, P.; Silvio; P.; Parker, W.; Chiappe, C. Chiral Ionic Liquids Supported on Natural Sporopollenin Microcapsules. *RSC Adv,* 2018, 8, 21174-21183,
33. Chiappe, C.; Demontis, G. C.; Bussolo, V. D.; Douton, M. J. R.; Rossella, F.; Pomelli, C. S.; Sartini, S.; Caporali, S., From Pollen Grains to Functionalized Microcapsultes: a Facile Chemical Route using Chiral Ionic Liquids, *Green Chem.* 2017, 19, 1028-1033.

34. Fan, T. F.; Park, S.; Shi, Q.; Zhang, X.; Liu, Q.; Song, Y.; Chin, H.; Ibrahim, M. S. B.; Mokrzecka, N.; Yang, Y; LI, H, Song, J.; Suresh, S; Cho, N. J. Transformation of Hard Pollen into Soft Matter, *Nature Com.* 2020, 11, 1449-1459.
35. Becherini, S.; Mitmoen, M; Tran, C. D., Natural Sporopollenin Microcapsules Facilitated Encapsulation of Phase Change Material into Cellulose Composites for Smart and Biocompatible Materials. *ACS Appl. Mater. Interfaces* 2019, 47, 44708-44721.
36. Tran, C. D.; Duni, S.; Delneri, A.; Franko, M. Chitosan-Cellulose Composite Materials Preparation, Characterization and Application for Removal of Microcystin. *J. Hazard. Mater.* 2013, 252-253, 355-366.
37. Yilmaz, E.; Sezgin, M.; Yi M. Enantioselective hydrolysis of rasemic naproxen methyl ester with sol-gel encapsulated lipase in the presence of sporopollenin. *J. Mol. Catal. B: Enzym.* 2010, 62, 162-168.
38. Zhang, X. X.; Fan, Y. F.; Tao, X. M., Yick, K. L. Crystallization and Prevention of Supercooling of Microencapsulated n-Alkanes, *J. Col. Interf. Sci.* 2005, 281, 299-306.
39. Oliver, M. J.; Calvert, P. D. Homogeneous Nucleation of n-Alkanes measured by Differential Scanning calorimetry, *J. Crystal. Growth* 1975, 30, 343-351.
40. Su, Y; Liu, G.; Xie, B.; Fu, D.; Wang, D, Crystallization Features of Normal Alkanes in Confined Geometry, *Acct. Chem. Res.* 2014, 47, 192-201.
41. He, F.; Wang, X. D.; Wu, D. Z., Phase-Change Characteristics and Thermal Performance of Form-Stable n-alkanes/silica Composite Phase Change Materials Fabricated by Sodium Silicate Precursor. *Renew Energy* 2015, 74, 689-698.
42. Sirota, E. B.; King, H. E.; Singer, D. M.; Shao, H. H. Rotator Phases of the Normal Alkanes: An X-ray Scattering Study. *J. Phys. Chem.* 1993, 98, 5809-5824.
43. Zhang, X.; Wang, X.; Wu, D. Design and Synthesis of Multifunctional Microencapsulated Phase Change Materials with Silver/Silica Double-Layered Shell for Thermal Energy Storage, Electrical Conduction and Antimicrobial Effectiveness, *Energy* 2016, 111, 498-512
44. Sirota, E. B.; King Jr. H. E.; Singer, D. M.; Shao, H. H. Rotator Phases of the Normal Alkanes: An X-ray Scattering Study, *J. Chem. Phys.* 1993, 98, 5809-5814.
45. Sirota, E. B.; Singer, D. M. Phase Transitions Among Rotator Phases of the Normal Alkanes, *J. Chem. Phys.* 1993, 101, 10873-10882.
46. Li, F.; Wang, X.; Wu, D. Fabrication of Multifunctional Microcapsules Containing n-Eicosane Core and Zinc Oxide Shell for Low Temperature Energy Storage, Photocatalysis and Antibiosis, *Energ. Conv. Management* 2015, 106, 873-885.
47. Do, C. V; Nguyen, T. T. T.; Park, J. S. Phase Change Core/Shell Structured Nanofibers Based on Eicosane/Poly (vinylidene fluoride) for Thermal Storage Applications, *Korean J. Chem. Eng.* 2013, 30, 1403-1409.
48. Sullivan, P. K. Solid-Phase Behavior of Several Long-Chain n-Paraffins, Esters, and a Ketone. *J. Res. Natl. Bur. Stand. (U.S.)* 1974, 78A, 129-141.
49. Chang, H.; Li, Q.; Xu, C.; Li, R.; Wang, H.; Bu, Z.; Lin, T. Wool powder: An efficient additive to improve mechanical and thermal properties of poly(propylene carbonate). *Compos. Sci. Technol.* 2017, 153, 119-127.

In the foregoing description, it will be readily apparent to one skilled in the art that varying substitutions and modifications may be made to the invention disclosed herein without departing from the scope and spirit of the invention.

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

I claim:

1. An ionic liquid composition comprising: (a) at least one structural polysaccharide and/or at least one structural protein dissolved in an ionic liquid; and (b) undissolved sporopollenin exine capsules (SEC), wherein the ionic liquid comprises 1-butyl-3-methylimidazolium chloride.

2. The composition of claim 1, wherein the structural polysaccharide is a polymer comprising 6-carbon monosaccharides linked via beta-1, 4 linkages.

3. The composition of claim 1, wherein the structural polysaccharide comprises cellulose.

4. The composition of claim 1, wherein the structural polysaccharide comprises chitin.

5. The composition of claim 1, wherein the structural polysaccharide comprises chitosan.

6. The composition of claim 1, wherein the structural protein comprises keratin.

7. The composition of claim 1, wherein the at least one structural polysaccharide and/or at least one structural protein is a mixture of at least two selected from cellulose, chitin, chitosan, and keratin.

8. The composition of claim 1, wherein the SECs contain an encapsulated material.

9. The composition of claim 8, wherein the encapsulated material comprises at least one of probiotics, prebiotics, fire retardant materials, and phase change materials.

10. The composition of claim 1, wherein the ionic liquid composition comprises at least 4% w/w of the dissolved structural polysaccharide and/or structural protein.

11. The composition of claim 1, wherein the ionic liquid composition comprises at least 10% w/w of the dissolved structural polysaccharide and/or structural protein.

12. A method for preparing a composite material comprising at least one structural polysaccharide and/or at least one structural polypeptide and undissolved sporopollenin exine capsules (SEC)s, the method comprising: (a) preparing the ionic liquid composition of claim 1 by dissolving the at least one structural polysaccharide and/or the at least one structural polypeptide in the ionic liquid and adding the undissolved SECs, and (b) removing the ionic liquid to obtain a composite material.

13. The method of claim 12, wherein the SECs contain an encapsulated material.

14. The method of claim 12, wherein the ionic liquid is removed by steps that include washing the ionic liquid composition with an aqueous solution to obtain the composite material and drying the composite material.

15. The method of claim 12, wherein the SECs are produced by a method comprising: (a) washing natural pollen grains with acetone for about 24 hours, (b) followed by washing with phosphoric acid for about 7 days, and (c) then washing with a strong alkaline for about 12 hours.

16. The method of claim 15, wherein the natural pollen grain is *Lycpodium clavatum*.

17. The method of claim 15, wherein the strong alkaline is potassium hydroxide.

18. The method of claim 13, wherein the material is encapsulated into the SECs by a method comprising: (a) mixing the encapsulated material with SECs produced by the method of claim 15, (b) heating the mixture under vacuum, (c) washing the mixture with ethanol, (d) filtering the mixture, and (e) drying the mixture.

19. The method of claim 18, wherein the encapsulated material comprises a material selected from the group consisting of phase change materials, fire retardant materials, probiotics, and prebiotics.

20. A method for delivering a material, the method comprising performing the method of claim 14, wherein the SECs contain an encapsulated material, and allowing the encapsulated material to diffuse from the composite material.

21. A method for producing a textile, the method comprising performing the method of claim 14, wherein the SECs encapsulate a phase change material, and adding the composite material to a fabric used in the production of a textile.

22. A method for producing a building material, the method comprising performing the method of claim 14, wherein the SECs encapsulate a phase change material, and adding the composite material to a mixture used in the production of a building material.

23. A method for producing a building material, the method comprising performing the method of claim 14, wherein the SECs encapsulate a fire retardant material, and adding the composite material to a mixture used in the production of a building material.

24. A method for producing a textile, the method comprising performing the method of claim 14, wherein the SECs encapsulate a fire retardant material, and adding the composite material to a fabric used in the production of a textile.

* * * * *